US012790365B2

(12) United States Patent
Miller et al.

(10) Patent No.: US 12,790,365 B2
(45) Date of Patent: Nov. 10, 2026

(54) SALTS AND CRYSTALLINE FORMS OF (3E) 3-[O-[(PHOSPHONOOXY)METHYL]OXIME]-PREGN-4-ENE-3,20-DIONE AND RELATED USES

(71) Applicant: Neuro Trauma Sciences LLC, Alpharetta, GA (US)

(72) Inventors: Raymond Brent Miller, St. Augustine, FL (US); Natalie Kelk, Edinburgh (GB); David Pearson, Meadowburn (GB); Gideon Shapiro, Gainesville, FL (US)

(73) Assignee: NeuroTrauma Sciences LLC, Alpharetta, GA (US)

( * ) Notice: Subject to any disclaimer, the term of this patent is extended or adjusted under 35 U.S.C. 154(b) by 444 days.

(21) Appl. No.: 18/555,707

(22) PCT Filed: Apr. 19, 2022

(86) PCT No.: PCT/US2022/025339
§ 371 (c)(1),
(2) Date: Oct. 16, 2023

(87) PCT Pub. No.: WO2022/225920
PCT Pub. Date: Oct. 27, 2022

(65) Prior Publication Data

US 2024/0247026 A1 Jul. 25, 2024

Related U.S. Application Data

(60) Provisional application No. 63/176,489, filed on Apr. 19, 2021.

(51) Int. Cl.
*C07J 51/00* (2006.01)
*A61K 31/661* (2006.01)

(52) U.S. Cl.
CPC ............ *C07J 51/00* (2013.01); *A61K 31/661* (2013.01)

(58) Field of Classification Search
CPC ............................... C07J 51/00; A61K 31/661
See application file for complete search history.

(56) References Cited

U.S. PATENT DOCUMENTS

| | | | |
|---|---|---|---|
| 5,245,757 | A | 9/1993 | Weissert et al. |
| 6,245,757 | B1 | 6/2001 | Chopp et al. |
| 6,331,534 | B1 | 12/2001 | Berliner et al. |
| 6,673,908 | B1 | 1/2004 | Stanton, Jr. |
| 8,614,203 | B2 | 12/2013 | Stein et al. |
| 8,778,915 | B2 | 7/2014 | Stein et al. |
| 9,527,881 | B2 | 12/2016 | Macnevin et al. |
| 9,802,978 | B2 | 10/2017 | Guthrie et al. |
| 10,336,787 | B2 | 7/2019 | Guthrie et al. |
| 10,487,109 | B2 | 11/2019 | Guthrie et al. |
| 11,053,276 | B2 | 7/2021 | Guthrie et al. |
| 11,274,118 | B2 | 3/2022 | Guthrie et al. |
| 11,725,025 | B2 | 8/2023 | Guthrie et al. |
| 2006/0217358 | A1 | 9/2006 | Bordet et al. |
| 2008/0318914 | A1 | 12/2008 | Hoffman et al. |
| 2009/0221544 | A1 | 9/2009 | Stein et al. |
| 2009/0325920 | A1 | 12/2009 | Hoffman et al. |
| 2011/0263553 | A1 | 10/2011 | Macnevin et al. |
| 2011/0306579 | A1 | 12/2011 | Stein |
| 2012/0245133 | A1 | 9/2012 | Hoffman et al. |
| 2012/0289491 | A1 | 11/2012 | Stein et al. |
| 2013/0210785 | A1 | 8/2013 | Guthrie et al. |
| 2013/0310350 | A1 | 11/2013 | Stein et al. |
| 2014/0349984 | A1 | 11/2014 | Hoffman et al. |
| 2016/0052957 | A1 | 2/2016 | Guthrie et al. |
| 2016/0194351 | A1 | 7/2016 | Guthrie et al. |
| 2018/0094018 | A1 | 4/2018 | Guthrie et al. |
| 2019/0276489 | A1 | 9/2019 | Guthrie et al. |
| 2020/0255470 | A1 | 8/2020 | Guthrie et al. |
| 2021/0395294 | A1 | 12/2021 | Guthrie et al. |
| 2022/0235092 | A1 | 7/2022 | Guthrie et al. |
| 2023/0357309 | A1 | 11/2023 | Guthrie et al. |

FOREIGN PATENT DOCUMENTS

| | | | |
|---|---|---|---|
| CA | 3068800 | A1 | 1/2019 |
| EP | 3033350 | B1 | 7/2021 |
| EP | 3978507 | A1 | 4/2022 |
| FR | 2238476 | A1 | 2/1975 |
| JP | H5-97678 | A | 4/1993 |
| JP | H5-507912 | A | 11/1993 |
| JP | 2007506675 | A | 3/2007 |
| JP | 2016539131 | A | 12/2016 |
| WO | WO 9119731 | A1 | 12/1991 |
| WO | WO-0230409 | A2 | 4/2002 |
| WO | WO-2006102596 | A2 | 9/2006 |
| WO | WO-2006102644 | A2 | 9/2006 |
| WO | WO-2008142720 | A2 | 11/2008 |
| WO | WO-2009097578 | A1 | 8/2009 |
| WO | WO-2009108804 | A2 | 9/2009 |
| WO | WO-2015023593 | A1 | 2/2015 |
| WO | WO-2022225920 | A1 | 10/2022 |

OTHER PUBLICATIONS

Alexis et al., "Nonocclusive Common Carotid Artery Thrombosis in the Rat Results in Reversible Sensorimotor and Cognitive Behavioral Deficits," Stroke, vol. 26, 1995, pp. 2336-2346, 16 pages.
Arvin et al., "The Role of Inflammation and Cytokines in Brain Injury," Neuroscience & Biobehavioral Reviews Autumn, vol. 20, No. 3, 1996, pp. 445-452.
Atif et al., "Progesterone in the Treatment of Neonatal Arterial Ischemic Stroke and Acute Seizures: Role of Bdnf/trkb Signaling," Neuropharmacology, vol. 107, 2016, pp. 317-328.

(Continued)

*Primary Examiner* — Kamal A Saeed
(74) *Attorney, Agent, or Firm* — Fenwick & West LLP

(57) ABSTRACT

The present disclosure relates to a crystalline form of (((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy) methyl dihydrogen phosphate), and pharmaceutically acceptable salts thereof, which may be useful in methods of treatment of the human or animal body. The present disclosure also relates to processes for the preparation of these compounds, to pharmaceutical compositions comprising them and to their use in the treatment of disorders, such as managing inflammation (e.g., inflammation resulting from traumatic brain injury or stroke).

18 Claims, 21 Drawing Sheets

(56) References Cited

OTHER PUBLICATIONS

Barbakadze et al., "Chemical Modification of Oximes With N-protected Amino Acids," Tetrahedron, vol. 70, 2014, pp. 7181-7184.
Barone et al., "Inflammatory Mediators and Stroke: New Opportunities for Novel Therapeutics," Journal of Cerebral Blood Flow and Metabolism, vol. 19, Aug. 1999, pp. 819-834.
Baulieu, "Neurosteroids: an overview," Adv Biochem Psychopharmacol, vol. 47, 1992, pp. 1-16.
Baulieu, "Neurosteroids: Of the Nervous System, by the Nervous System, for the Nervous System," Recent Progress in Hormone Research, vol. 52, 1997, pp. 1-32.
Beaumont et al., "The Impact-Acceleration Model of Head Injury: Injury Severity Predicts Motor and Cognitive Performance after Trauma," Neurological Research, vol. 21, 1999, pp. 742-754.
Becker et al., "Neuroanatomical Bases of Spatial Memory," Brain Research, vol. 200, Nov. 1980, pp. 307-320.
Bederson et al., "Rat Middle Cerebral Artery Occlusion: Evaluation of the Model and Development of a Neurologic Examination," Stroke, vol. 17, No. 3, May-Jun. 1986, pp. 472-476.
Betz et al., "Effect of Steroids on Edema and Sodium Uptake of the Brain During Focal Ischemia in Rats," Stroke, vol. 21, No. 8, Aug. 1990, pp. 1199-1204.
Brooks et al., "Gas Chromatographic and Mass Spectrometric Studies of Oximes Derived From 20-0xosteroids," Steroids, vol. 15, No. 2, 1970, pp. 283-301.
Chao et al., "Steroid Sex Hormones and Macrophage Function: Modulation of Reactive Oxygen Intermediates and Nitrite Release," American Journal of Reproductive Immunology, vol. 32, Aug. 1994, pp. 43-52.
Check et al., "Lymphocyte Immunotherapy (LI) Increases Serum Levels of Progesterone Induced Blocking Factor (PIBF)," American Journal of Reproductive Immunology, vol. 37, Issue 1, 1997, pp. 17-20.
Choudhary et al., "Pregnenolone Derivatives as Potential Anticancer Agents," Steroids, vol. 76, 2011, pp. 1554-1559.
Corey et al., "Reaction of oxime O-acetates with chromous acetate. Method for the conversion of ketoximes to ketones under mild conditions," Journal of the American Chemical Society, vol. 92, No. 17, May 11, 1970, pp. 5276-5277.
De Ryck et al., "Neocortical localization of tactile/proprioceptive limb placing reactions in the rat," Brain Research (1992) 573(1), pp. 44-60.
Del Zoppo et al., "Advances in the Vascular Pathophysiology of Ischemic Stroke, Thrombosis Research," vol. 98, Issue 3, May 1, 2000, pp. 73-81.
Djebaili et al., "Allopregnanolone and progesterone decrease cell death and cognitive deficits after a contusion of the rat pre-frontal cortex," Neuroscience, vol. 123, Issue 2, Feb. 2004, pp. 349-359.
Djebaili et al., "The Neurosteroids Progesterone and Allopregnanolone Reduce Cell Death, Gliosis, and Functional Deficits after Traumatic Brain Injury in Rats," Journal of Neurotrauma, vol. 22, No. 1, Jan. 21, 2005, pp. 106-118.
Ganter et al., "Growth Control of Cultured Microglia, Journal of Neuroscience Research," vol. 33, Issue 2, Oct. 1992, pp. 218-230.
Garcia-Estrada et al., "Dehydroepiandrosterone, Pregnenolone and Sexsteroids Down-Regulate Reactive Astroglia in the Male Ratbrain after a Penetrating Brain Injury," International Journal of Developmental Neuroscience, vol. 17, Issue 2, Apr. 1999, pp. 145-151.
Garcia-Estrada et al., "Gonadal Hormones Down-Regulate Reactive Gliosis and Astrocyte Proliferation after a Penetrating Brain Injury," Brain Research, vol. 628, Issues 1-2, Nov. 19, 1993, pp. 271-278.
Goodman et al., "Estrogens attenuate and corticosterone exacerbates excitotoxicity, oxidative injury, and amyloid beta-peptide toxicity in hippocampal neurons," Journal of Neurochemistry, vol. 66, May 1996, pp. 1836-1844.
Grossman et al., "Effects of Progesterone on the Inflammatory Response to Brain Injury in the Rat," Brain Research, vol. 1008, Issue 1, May 15, 2004, pp. 29-39.
Guthrie, D.B., et al.; "Water-soluble progesterone analogues are effective, injectable treatments in animal models of traumatic brain injury," ACS Med Chem. Lett, (2012); 3(5):362-366.
Hannay et al., "Outcome Measures for Patients with Head Injuries: Report of the Outcome Measures Subcommittee," Journal of Head Trauma Rehabilitation, vol. 11, No. 6, Dec. 1996, pp. 41-50.
Hartmann et al., "Synthesis and evaluation of novel steroidal oxime inhibitors of P450 17 (17 alpha-hydroxylase/C17-20-lyase) and 5 alpha-reductase types 1 and 2," Journal of Medicinal Chemistry, vol. 43, 2000, pp. 4266-4277.
Hayashi et al., "Novel non-peptide nociceptin/orphanin FQ receptor agonist, 1-[1-(1-Methylcyclooctyl)-4-piperidinyl]-2-[(3R)-3-piperidinyl]-1H-benzimidazole: design, synthesis, and structure-activity relationship of oral receptor occupancy in the brain for orally potent antianxiety drug," Journal of Medicinal Chemistry, vol. 52, No. 3, Feb. 12, 2009, pp. 610-625.
Hayes et al., "Neurotransmitter-mediated mechanisms of traumatic brain injury: acetylcholine and excitatory amino acids," Journal of Neurotrauma, vol. 9, Supplement 1, Apr. 1992, pp. S173-S187.
He et al., "Allopregnanolone, a Progesterone Metabolite, Enhances Behavioral Recovery and Decreases Neuronal Loss after Traumatic Brain Injury," Restorative Neurology and Neuroscience, vol. 22, No. 1, Jan. 1, 2004, pp. 19-31.
He et al., "Progesterone and Allopregnanolone Reduce Inflammatory Cytokines after Traumatic Brain Injury," Experimental Neurology, vol. 189, No. 2, Jun. 7, 2004, pp. 404-412.
Hoffman et al., "Allopregnanolone Promotes Functional Recovery from TBI by Reducing Cerebral Edema and Neuronal Death," Academy of Emergency Medicine, vol. 8, 2001, pp. 496-497.
Hoffman et al., "Bilateral Frontal Cortical Contusion in Rats: Behavioral and Anatomie Consequences," Journal of Neurotrauma, vol. 11, No. 4, Aug. 1994, pp. 417-431.
Holmin et al., "Intracerebral Inflammatory Response to Experimental Brain Contusion, Acta Neurochirurgica," vol. 132, Mar. 1995, pp. 110-119.
Huttunen, et al., "Prodrugs—from Serendipity to Rational Design", Pharmacological Reviews, vol. 63, No. 3, Sep. 2011, pp. 750-771.
Jiang et al., "Progesterone is Neuroprotective after Transient Middle Cerebral Artery Occlusion in Male Rats," Brain Research, vol. 735, Issue 1, Sep. 30, 1996, pp. 101-107.
Kelly et al., "The inhibition of synthesis of a beta-chemokine, monocyte chemotactic protein-1 (MCP-1) by progesterone," Biochemical and Biophysical Research Communications, vol. 239, Issue 2, Oct. 20, 1997, pp. 557-561.
Kim et al., "Synthesis of Pregnane Derivatives, Their Cytotoxicity on LNCap and PC-3 Cells, and Screening on 5a-Reductase Inhibitory Activity," Molecules, vol. 14, 2009, pp. 4655-4668.
Kline et al., "Methylphenidate treatment following ablation-induced hemiplegia in rat: experience during drug action alters effects on recovery of function," Pharmacology Biochemistry and Behavior, vol. 48, Jul. 1994, pp. 773-779.
Lambert et al., "Neurosteroids and GABAA receptor function," Trends in Pharmacological Sciences, vol. 16, Issue 9, Sep. 1995, pp. 295-303.
Lindner et al., "Dissociable long-term cognitive deficits after frontal versus sensorimotor cortical contusions," Journal of Neurotrauma, vol. 15, No. 3, Mar. 1998, pp. 199-216.
Lyeth et al., "Cholinergic and opioid mediation of traumatic brain injury," Journal of Neurotrauma, vol. 9, No. 2, 1992, pp. S463-S474.
MacNevin et al., "Development and screening of water-soluble analogues of progesterone and allopregnanolone in models of brain injury," Journal of Medicinal Chemistry, vol. 52, No. 19, Oct. 8, 2009, pp. 6012-6023.
Mantyla, A., et al.; "Design, synthesis and in vitro evaluation of novel water-soluble prodrugs of buparvaquone," Eur J Pharm Sci. (2004); 23(2):151-158.
Markgraf et al., "Sensorimotor and Cognitive Consequences of Middle Cerebral Artery Occlusion in Rats," Brain Research, vol. 575, No. 2, Mar. 1992, pp. 238-246.
Mattson et al., "Cellular Signaling Roles of TGF , TNFa and APP in Brain Injury Responses and Alzheime s Disease," Brain Research Reviews, vol. 23, Issues 1-2, Feb. 1997, pp. 47-61.

(56) References Cited

OTHER PUBLICATIONS

Maurice et al., "Sigma1 (sigma 1) receptor agonists and neurosteroids attenuate B25-35-amyloid peptide-induced amnesia in mice through a common mechanism," Neuroscience, vol. 83, Issue 2, Dec. 31, 1998, pp. 413-428.
Maurice et al., "Modulation by neurosteroids of the in vivo (+)-[3H]SKF-10,047 binding to sigma 1 receptors in the mouse forebrain," Journal of Neuroscience Research, 1996; 46(6):734-743.
Miller et al., "Progesterone Inhibits Inducible Nitric Oxide Synthase Gene Expression and Nitric Oxide Production in Murine Macrophages," Journal of Leukocyte Biology, vol. 59, Issue 3, Mar. 1996, pp. 442-450.
Morris, "Developments of a Water-Maze Procedure for Studying Spatial Learning in the Rat," Journal of Neuroscience Methods, vol. 11, May 1984, pp. 47-60.
Murphy et al., "Progesterone administration during reperfusion, but not preischemia alone, reduces injury in ovariectomized rats," Journal of Cerebral Blood Flow & Metabolism, vol. 22, No. 10, Oct. 2002, pp. 1181-1188.
Murphy et al., "Progesterone Exacerbates Striatal Stroke Injury in Progesterone-Deficient Female Animals," Stroke, vol. 31, No. 5, May 2000, pp. 1173-1178.
Perera et al., "Inflammation Following Stroke," Journal of Clinical Neuroscience, vol. 13, No. 1, Jan. 2006, pp. 1-8.
Pettus et al., "Progesterone Treatment Inhibits the Inflammatory Agents that Accompany Traumatic Brain Injury," Brain Research, vol. 1049, No. 1, Jul. 5, 2005, pp. 112-119.
Raivich et al., "Signaling Molecules and Neuroglial Activation in the Injured Central Nervous System," The Keio Journal of Medicine, vol. 45, Issue 3, Sep. 1996, pp. 239-247.
Reddy et al., "Sigma (sigma1) receptor mediated anti-depressant-like effects of neurosteroids in the Porsolt forced swim test," NeuroReport, vol. 9, Issue 13, Sep. 14, 1998, pp. 3069-3073.
Reddy et al., "Role of GABA-A and mitochondrial diazepam binding inhibitor receptors in the anti-stress activity of neurosteroids in mice," Psychopharmacology, vol. 128, Dec. 1, 1996, pp. 280-292.
Robel et al., "Neurosteroids: Biosynthesis and Function," Critical Reviews in Neurobiology, vol. 9, No. 4, Jan. 1, 1995, pp. 383-394.
Robert et al., "Effects of female hormones (17beta-estradiol and progesterone) on nitric oxide production by alveolar macrophages in rats," Nitric Oxide, vol. 1, Issue 6, Dec. 1997, pp. 453-462.
Roof et al., "Progesterone Facilitates Cognitive Recovery and Reduces Secondary Neuronal Loss Caused by Cortical Contusion Injury in Male Rats," Experimental Neurology, vol. 129, Issue 1, Sep. 1994, pp. 64-69.
Roof et al., "Progesterone Protects Against Lipid Peroxidation Following Traumatic Brain Injury in Rats," Molecular and Chemical Neuropathology, vol. 31, May 1997, pp. 1-11.
Schallert et al., "Posture-Independent Sensorimotor Analysis of Inter-Hemispheric Receptor Asymmetries in Neostriatum," Pharmacology Biochemistry and Behavior, vol. 18, No. 5, May 1983, pp. 753-759.
Soares et al., "Inflammatory Leukocytic Recruitment and Diffuse Neuronal Degeneration are Separate Pathological Processes Resulting from Traumatic Brain Injury," The Journal of Neuroscience, vol. 15, No. 12, Dec. 1995, pp. 8223-8233.
Stein, "Embracing Failure: What the Phase III Progesterone Studies Can Teach about TBI Clinical Trials," Brain Injury, vol. 29, No. 11, Sep. 19, 2015, pp. 1259-1272.
Stein et al., "Goldstein et al.'s Secondary Analysis of Progesterone Clinical Trial for Traumatic Brain Injury Can Only Reflect the Same Trial Design Flaws: A Response to "Very Early Administration of Progesterone Does Not Improve Neuropsychological Outcomes in Subjects with Moderate to Severe Traumatic Brain Injury"," J Neurotrauma. (2017); 34(13):2192-2193.
Stein, "The Case for Progesterone," Annals of the New York Academy of Sciences, vol. 1052, No. 1, Jun. 2005, pp. 152-169.
Stroemer et al., "Neocortical neural sprouting, synaptogenesis, and behavioral recovery after neocortical infarction in rats," Stroke, vol. 26, Issue 11, Nov. 1995, pp. 2135-2144, 20 pages.
Subramanian et al., Gestation Confers Temporary Resistance to Peroxidation in the Maternal Rat Brain, Neuroscience Letters, vol. 155, Issue 2, Jun. 11, 1993, pp. 151-154.
Szekeres-Bartho et al., "The antiabortive effect of progesterone-induced blocking factor in mice is manifested by modulating NK activity," Cellular Immunology, vol. 177, Issue 2, May 1, 1997, pp. 194-199.
Szekeres-Bartho et al., "The Immunological Pregnancy Protective Effect of Progesterone is Manifested via Controlling Cytokine Production," American Journal of Reproductive Immunology, vol. 35, No. 4, Apr. 1996, pp. 348-351.
Vasil'Tsov et al., "First Example of Construction of a Pyrrole Ring Bonded to a Steroid System by the Trofimov Reaction," Chemistry of Heterocyclic Compounds, vol. 37, No. 12, Dec. 2001, pp. 1488-1492.
Vaudano et al., "The effects of a lesion or a peripheral nerve graft on GAP-43 upregulation in the adult rat brain: an in situ hybridization and immunocytochemical study," The Journal of Neuroscience, vol. 15, No. 5 Part 1, May 1995, pp. 3594-3611.
Vedder et al., "Estrogen hormones reduce lipid peroxidation in cells and tissues of the central nervous system," Journal of Neurochemistry, vol. 72, Issue 6, Jun. 1999, pp. 2531-2538.
Wali et al., "Evaluating the neurotherapeutic potential of a water-soluble progesterone analog after traumatic brain injury in rats," Neuropharmacology (Oct. 2016); 109:148-158.
Wali et. al. "Synthesis of Progesterone Analog, EIDD-1723", Supplementary Information to: Neuropharmacology (2016), 109, 148-158, DOI: 10.1016/j.neuropharm.2016.05.017,Jun. 4, 2016, pp. 1-5.
Webster et al., "Progesterone treatment reduces neuroinflammation, oxidative stress and brain damage and improves long-term outcomes in a rat model of repeated mild traumatic brain injury," Journal of Neuroinflammation, vol. 12, Issue 238, 2015, 13 pages.
Wright et al., "Serum Progesterone Levels Correlate with Decreased Cerebral Edema after Traumatic Brain Injury in Male Rats," Journal of Neurotrauma, vol. 18, No. 9, Sep. 2001, pp. 901-909.
Wright et al., "ProTECT: a randomized clinical trial of progesterone for acute traumatic brain injury," Annals of Emergency Medicine, vol. 49, Issue 4, Apr. 1, 2007, pp. 391-402, 402.e1-2, 8 pages.
Wright et al., "Very Early Administration of Progesterone for Acute Traumatic Brain Injury," The New England Journal of Medicine, (2014); 371(26):2457-66.
Yousuf et al., "Neuroprotection by Progesterone After Transient Cerebral Ischemia in Stroke-prone Spontaneously Hypertensive Rats," Hormones and Behavior, vol. 84, 2016, pp. 29-40.

Under cross polarised lenses

Under plane polarised lenses

Under cross polarised lenses

Under plane polarised lenses

SALTS AND CRYSTALLINE FORMS OF (3E) 3-[O-[(PHOSPHONOOXY)METHYL]OXIME]-PREGN-4-ENE-3,20-DIONE AND RELATED USES

RELATED APPLICATIONS

The application is a U.S. National Phase application, filed under U.S.C. § 371, of International Application No. PCT/US2022/025339, filed Apr. 19, 2022, which claims priority to, and the benefit of, U.S. Provisional Application No. 63/176,489, filed Apr. 19, 2021, the entire content of each of which are incorporated herein by reference in their entireties.

FIELD OF DISCLOSURE

The present disclosure relates to a crystalline form of (((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy) methyl dihydrogen phosphate), and pharmaceutically acceptable salts thereof, which may be useful in methods of treatment of the human or animal body. The present disclosure also relates to processes for the preparation of these compounds, to pharmaceutical compositions comprising them and to their use in the treatment of disorders, such as managing inflammation (e.g., inflammation resulting from traumatic brain injury or stroke).

BACKGROUND

Brain injuries, including traumatic brain injury (TBI) and stroke, affect over 2 million Americans each year and are a significant health concern worldwide. Traumatic brain injuries result from a blow or jolt to the head or a penetrating head injury that disrupts the function of the brain, with severity ranging from "mild," i.e., a brief change in mental status or consciousness to "severe," i.e., an extended period of unconsciousness or amnesia after the injury. Strokes are a result of diseases that affect the blood vessels that supply blood to the brain. A stroke occurs when a blood vessel that brings oxygen and nutrients to the brain either bursts (hemorrhagic stroke) or is clogged by a blood clot or some other mass (ischemic stroke). The majority of strokes are ischemic, however hemorrhagic strokes typically result in more severe injuries. Despite several decades of effort, scientists have not yet found a pharmacological agent that consistently improves outcomes after stroke or a TBI.

After a TBI or stroke, inflammation is a principle cause of secondary damage and long-term damage. Following insults to the central nervous system, a cascade of physiological events leads to neuronal loss including, for example, an inflammatory immune response and excitotoxicity resulting from disrupting the glutamate, acetylcholine, cholinergic, GABAA, and NMDA receptor systems. In these cases, a complex cascade of events leads to the delivery of blood-borne leucocytes to sites of injury to kill potential pathogens and promote tissue repair. However, the powerful inflammatory response has the capacity to cause damage to normal tissue, and dysregulation of the innate, or acquired immune response is involved in different pathologies.

The disclosure arises from a need to provide further compounds for the treatment of disorders, including a TBI or stroke. In particular, compounds with improved physicochemical, pharmacological and pharmaceutical properties to existing compounds are desirable.

SUMMARY

In some aspects, the present disclosure provides a crystalline form of Compound 1, Compound 1

(i.e.,

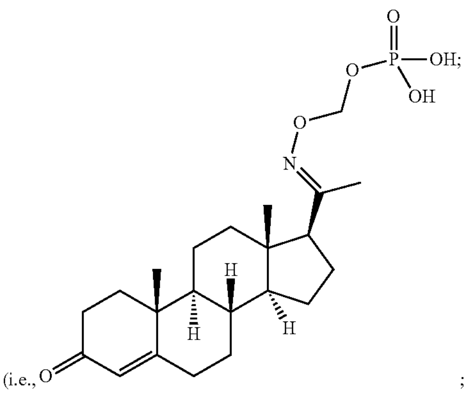

;

(((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy) methyl dihydrogen phosphate)) or a pharmaceutically acceptable salt thereof.

In some aspects, the present disclosure provides a Form I crystalline form of the bis-tris monohydrate salt of Compound 1.

In some aspects, the present disclosure provides a Form II crystalline form of the bis-tris of Compound 1.

In some aspects, the present disclosure provides a Form III crystalline form of the mono-tris salt of Compound 1.

In some aspects, the present disclosure provides a Form IV crystalline form of the mono-tris anhydrous salt of Compound 1.

In some aspects, the present disclosure provides a Form V crystalline form of the bis-N-(hydroxyethyl) pyrrolidine salt of Compound 1.

In some embodiments, the present application provides an amorphous form of Compound 1.

In some aspects, the present disclosure provides a method of preparing a crystalline form of Compound 1 or a pharmaceutically acceptable salt thereof described herein (e.g., a method comprising one or more steps described in Scheme 1).

The present application also provides a pharmaceutical composition comprising any one of the solid forms of Compound 1 as described herein (e.g., any of Forms I, II, III, IV, V, and the amorphous form), and one or more pharmaceutically acceptable carrier or excipient.

In some aspects, the present disclosure provides pharmaceutical compositions comprising a crystalline form of Compound 1 or a pharmaceutically acceptable salt thereof described herein, and one or more pharmaceutically acceptable carrier or excipient.

In some aspects, the present disclosure provides a method of managing inflammation (e.g., in vitro or in vivo), comprising contacting a cell with an effective amount of a crystalline form of Compound 1 or a pharmaceutically acceptable salt thereof.

In some aspects, the present disclosure provides a method of treating or preventing a disease or disorder disclosed herein in a subject in need thereof, comprising administering to the subject an effective amount of a crystalline form of Compound 1 or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a crystalline form of Compound 1 or a pharmaceutically acceptable salt thereof, or a pharmaceutical composition of the present disclosure.

In some aspects, the present disclosure provides a crystalline form of Compound 1 or a pharmaceutically acceptable salt thereof for use in managing inflammation (e.g., in vitro or in vivo).

In some aspects, the present disclosure provides crystalline form of Compound 1 or a pharmaceutically acceptable salt thereof for use in treating or preventing a disease or disorder disclosed herein.

In some aspects, the present disclosure provides a crystalline form of Compound 1 or a pharmaceutically acceptable salt thereof for use in treating a disease or disorder disclosed herein.

In some aspects, the present disclosure provides use of a crystalline form of Compound 1 or a pharmaceutically acceptable salt thereof in the manufacture of a medicament for managing inflammation (e.g., in vitro or in vivo).

In some aspects, the present disclosure provides use of a crystalline form of Compound 1 or a pharmaceutically acceptable salt thereof in the manufacture of a medicament for treating or preventing a disease or disorder disclosed herein.

In some aspects, the present disclosure provides use of a crystalline form of Compound 1 or a pharmaceutically acceptable salt thereof in the manufacture of a medicament for treating a disease or disorder disclosed herein.

In some aspects, the present disclosure provides a composition comprising ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl) ethylidene)amino)oxy)methyl dihydrogen phosphate tris salt, (Compound 1A)

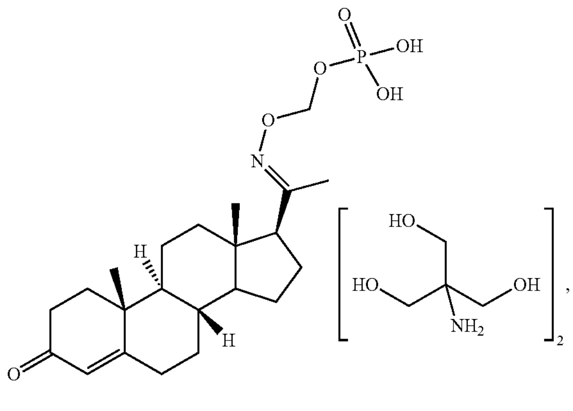

having a purity greater than or equal to about 98.0% as determined by HPLC.

In some embodiments, the composition comprises less than 2% of an impurity selected from (Compound A)

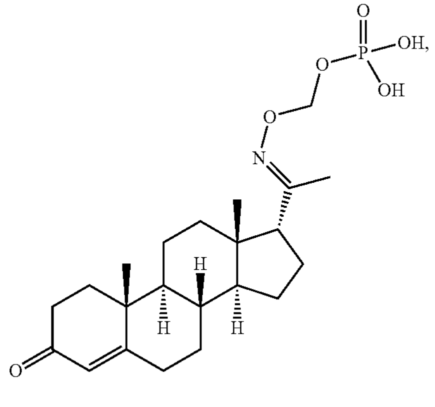

or pharmaceutically acceptable salt thereof;

(Compound B)

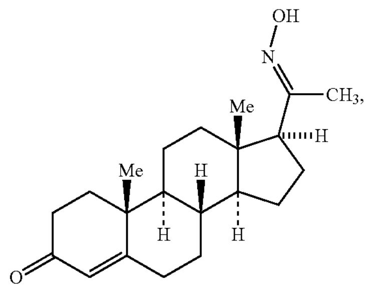

or pharmaceutically acceptable salt thereof; and (Compound C)

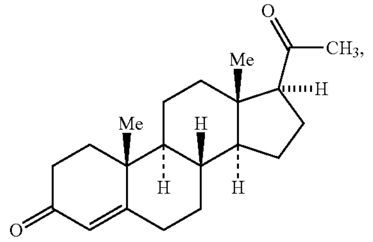

or a pharmaceutically acceptable salt thereof, and combinations thereof.

In some embodiments, Compound A is present by weight from about 0.01% to about 0.5%.

In some embodiments, Compound A is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some embodiments, Compound B is present by weight from about 0.01% to about 0.5%.

In some embodiments, Compound B is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some embodiments, Compound C is present by weight from about 0.01% to about 0.5%.

In some embodiments, Compound C is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some aspects, the present disclosure provides a pharmaceutical composition comprising:

a) about 98% ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl) ethylidene)amino)oxy)methyl dihydrogen phosphate tris salt, (Compound 1A)

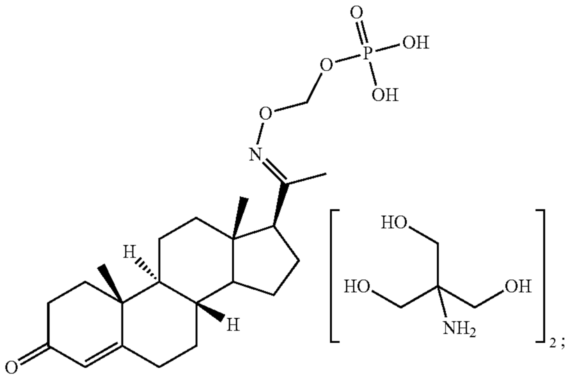

b) up to about 0.1%

(Compound A)

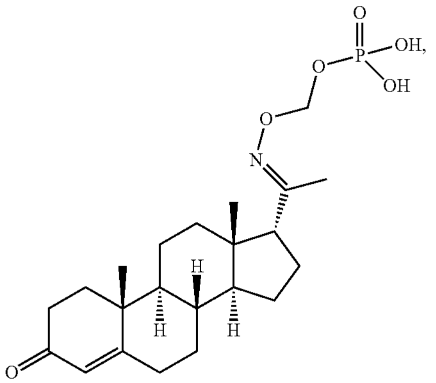

or pharmaceutically acceptable salt thereof;

c) up to about 0.5%

(Compound B)

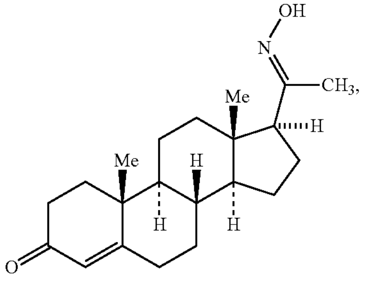

or a pharmaceutically acceptable salt thereof;

d) up to about 0.1%

(Compound C)

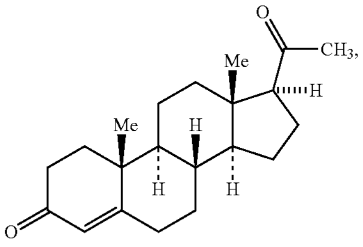

or a pharmaceutically acceptable salt thereof.

In some aspects, the present disclosure provides a method of treating or preventing a disease or disorder in a subject in need thereof, wherein the subject is administered a therapeutically effect amount of the composition or the pharmaceutical composition of the present disclosure.

In some aspects, the present disclosure provides a composition or a pharmaceutical composition of the present disclosure for use in treating or preventing a disease or disorder in a subject in need thereof.

In some aspects, the present disclosure provides the use of a composition or a pharmaceutical composition of the present disclosure, for use in the manufacture of a medicament for the treatment or prevention of a disease or disorder in a subject in need thereof.

In some aspects, the present disclosure provides the use of a composition or a pharmaceutical composition of the present disclosure, for the treatment or prevention of a disease or disorder in a subject in need thereof.

In some embodiments, the disease or disorder is a stroke or a traumatic brain injury.

In some embodiments, the disease or disorder is a symptom of stroke or traumatic brain injury.

In some embodiments, the disease or disorder is the progression of a stroke or traumatic brain injury.

In some embodiments, the disease or disorder is an edema following stroke or traumatic brain injury.

In some embodiments, the disease or disorder is a neurodegenerative disease.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTIONS OF FIGURES

DETAILED DESCRIPTION

Figure 1:
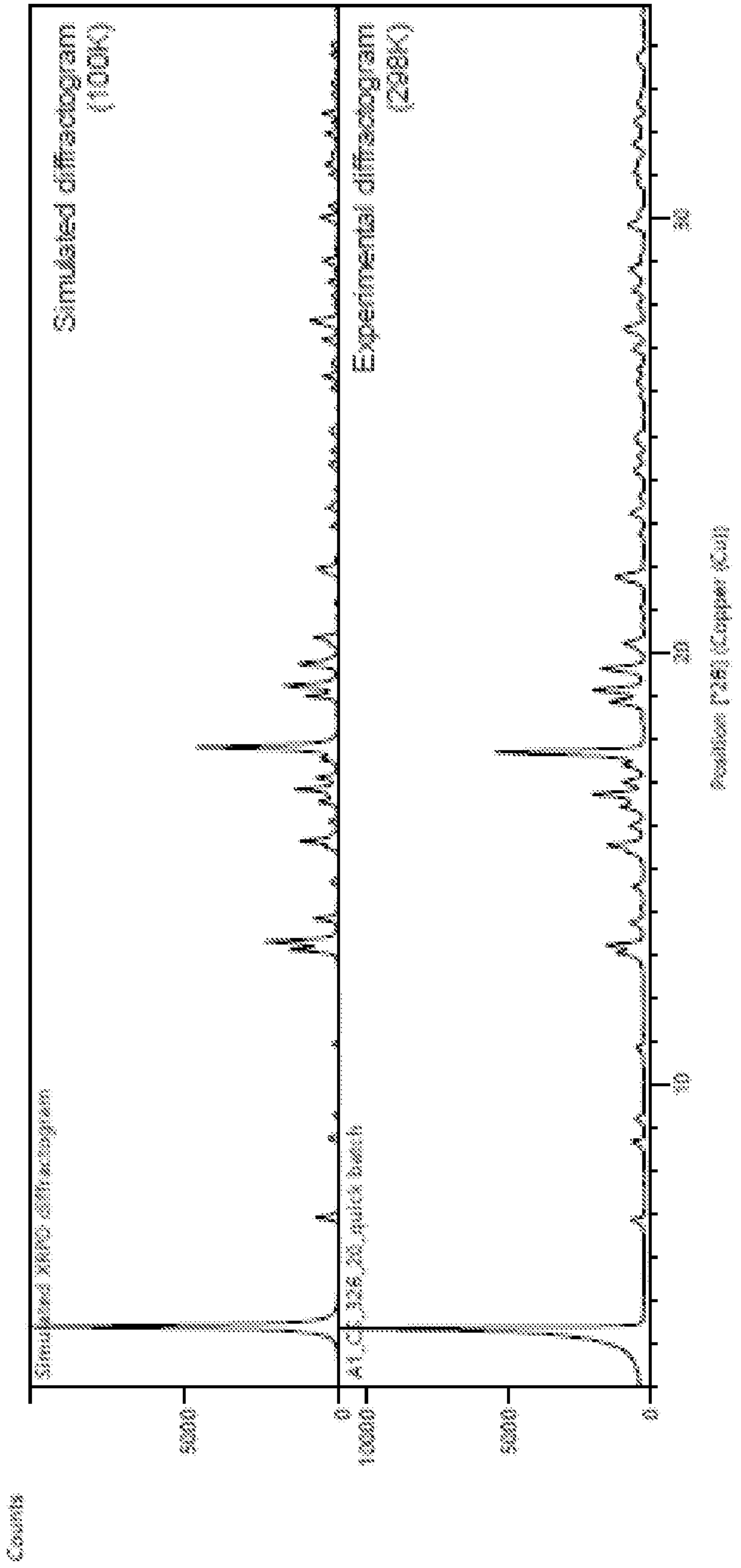
FIG. 1 depicts the XRPD spectrum for Form I.

The disclosure relates to crystalline forms useful for the managing inflammation. In some embodiments, compounds with improved physicochemical, pharmacological and pharmaceutical properties to existing steroid derivatives are desired.

Definitions

Unless otherwise stated, the following terms used in the specification and claims have the following meanings set out below.

It is understood that the compounds described herein include the compounds themselves, as well as their salts, and their solvates, if applicable. A salt, for example, can be formed between an anion and a positively charged group (e.g., amino) on a substituted benzene compound. Suitable anions may include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations may include sodium ion, potassium ion, magnesium ion, calcium ion, and an ammonium cation such as tetramethylammonium ion. The substituted benzene compounds also include those salts containing quaternary nitrogen atoms.

It is understood that the compounds of the present disclosure, for example, the salts of the compounds, can exist in either hydrated or unhydrated (the anhydrous) form or as solvates with other solvent molecules. Nonlimiting examples of hydrates may include monohydrates and dihydrates. Nonlimiting examples of solvates may include ethanol solvates and acetone solvates.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of a crystalline form of Compound 1 or a pharmaceutically acceptable salt thereof.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that a crystalline form of Compound 1 or a pharmaceutically acceptable salt thereof can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognised reference textbooks of organic synthesis known to those in the art One of ordinary skill in the art will note that, during the reaction sequences and synthetic scheme described herein, the order of certain steps may be changed, such as the introduction and removal of protecting groups. One of ordinary skill in the art will recognise that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M.,

*Protective Groups in Organic Synthesis,* $3^{rd}$ edition, John Wiley & Sons: New York, 1999.

It is to be understood that, unless otherwise stated, any description of a method of treatment or prevention includes use of a crystalline form of Compound 1 or a pharmaceutically acceptable salt thereof to provide such treatment or prevention as is described herein. It is to be further understood, unless otherwise stated, any description of a method of treatment or prevention includes use of a crystalline form of Compound 1 or a pharmaceutically acceptable salt thereof to prepare a medicament to treat or prevent such condition. The treatment or prevention includes treatment or prevention of human or non-human animals including rodents and other disease models.

It is to be understood that, unless otherwise stated, any description of a method of treatment includes use of a crystalline form of Compound 1 or a pharmaceutically acceptable salt thereof to provide such treatment as is described herein. It is to be further understood, unless otherwise stated, any description of a method of treatment includes use of a crystalline form of Compound 1 or a pharmaceutically acceptable salt thereof to prepare a medicament to treat such condition. The treatment includes treatment of human or non-human animals including rodents and other disease models.

As used herein, the term "subject" refers to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

In some embodiments, the term "subject in need thereof" can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject in need thereof may be resistant at start of treatment or may become resistant during treatment. In some embodiments, the subject in need thereof received and failed all known effective therapies for a disease or disorder disclosed herein. In some embodiments, the subject in need thereof received at least one prior therapy.

It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

As used herein, the term "treating" or "treat" describes the management and care of a patient for the purpose of combating a disease, condition, or disorder and includes the administration of a compound of the present disclosure, or a pharmaceutically acceptable salt, crystalline form or solvate thereof, to alleviate the symptoms or complications of a disease, condition or disorder, or to eliminate the disease, condition or disorder. The term "treat" can also include treatment of a cell in vitro or an animal model.

It is to be understood that a crystalline form of Compound 1 or a pharmaceutically acceptable salt thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that "solubility" or "solubility rating" refers to the property of a crystalline form (e.g., Form I, II III, IV, V, VI, VII, VIII, or IX) disclosed herein to dissolve in a liquid solvent and form a homogeneous solution. In some embodiments, solubility is expressed as a concentration, either by mass of solute per unit volume of solvent (e.g., g of solute per kg of solvent, g per dL (100 mL), mg/ml, etc.), molarity, molality, mole fraction, or other similar descriptions of concentration. A person of skill in the art may understand that the maximum equilibrium amount of solute that can dissolve per amount of solvent is the solubility of that solute in that solvent under the specified conditions, including temperature, pressure, pH, and the nature of the solvent. In some embodiments, solubility is measured at physiological pH, or non-physiological pH, for example, at about pH 5.0, about pH 6.0, about pH 7.0, about pH 7.4, about pH 7.6, about pH 7.8, or about pH 8.0 (e.g., about pH 5-8). In some embodiments, solubility is measured in water or a physiological buffer, for example PBS, NaCl (with or without $NaPO_4$), or FaSSIF. In some embodiments, solubility is measured in a biological fluid (solvent) (e.g., blood or serum). In some embodiments, the temperature is be about room temperature (e.g., about 20, about 21, about 22, about 23, about 24, or about 25° C.) or about body temperature (about 37° C.). In some embodiments, an agent has a solubility rating of at least about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 40, about 50, about 60, about 70, about 80, about 90 or about 100 mg/ml at room temperature or at 37° C.

As used herein, "stable" refers to a crystalline form that maintains purity, appearance, and/or analytical parameters over a defined time and temperature as compared to the crystalline form as isolated. In some embodiments, the "stable" crystalline form exhibits less than about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, or about 0.1% impurity over a set period of time (e.g., 1 day, 2 days, 3 days, 4 days, 5 days, 6 days, one week, two weeks, three weeks, one month, two months, three months, or four months). For example, a crystalline form is stable if after two weeks at room temperature the DSC and TGA profiles are consistent with the originally isolated crystalline form.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising a crystalline form of Compound 1 or a pharmaceutically acceptable salt thereof in combination with at least one pharmaceutically acceptable excipient or carrier.

As used herein, the term "pharmaceutical composition" is a formulation containing a crystalline form of Compound 1 or a pharmaceutically acceptable salt thereof in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with one or more pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims may include both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for managing inflammation. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the term "effective amount", refers to an amount of a pharmaceutical agent to treat or ameliorate an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount or effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy.

The pharmaceutical compositions containing a crystalline form of Compound 1 or a pharmaceutically acceptable salt thereof may be manufactured in a manner that is generally known, e.g., by means of conventional mixing, dissolving, granulating, dragee-making, levigating, emulsifying, encapsulating, entrapping, or lyophilising processes. Pharmaceutical compositions may be formulated in a conventional manner using one or more pharmaceutically acceptable carrier comprising excipients and/or auxiliaries that facilitate processing of a crystalline form of Compound 1 or a pharmaceutically acceptable salt thereof into preparations that can be used pharmaceutically. The appropriate formulation is dependent upon the route of administration chosen.

The crystalline form of Compound 1 or a pharmaceutically acceptable salt thereof can be prepared with one or more pharmaceutically acceptable carrier that will protect the compound against rapid elimination from the body, such as a controlled release formulation, including an implant and microencapsulated delivery system.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term "pharmaceutically acceptable salts" refers to derivatives of the compounds of the present disclosure wherein the parent compound is modified by making an acid or base salt thereof. Examples of pharmaceutically acceptable salts may include, but are not limited to, mineral or organic acid salts of basic residues such as amines, alkali or organic salts of acidic residues such as carboxylic acids, and the like. The pharmaceutically acceptable salts may include the conventional non-toxic salts or the quaternary ammonium salts of the parent compound formed, for example, from non-toxic inorganic or organic acids. For example, such conventional non-toxic salts may include, but are not limited to, those derived from inorganic and organic acids selected from 2-acetoxybenzoic, 2-hydroxyethane sulphonic, acetic, ascorbic, benzene sulphonic, benzoic, bicarbonic, carbonic, citric, edetic, ethane disulphonic, 1,2-ethane sulphonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulphonic, maleic, malic, mandelic, methane sulphonic, napsylic, nitric, oxalic, pamoic, pantothenic, phenylacetic, phosphoric, polygalacturonic, propionic, salicylic, stearic, subacetic, succinic, sulphamic, sulphanilic, sulphuric, tannic, tartaric, toluene sulphonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt. In some embodiments, the pharmaceutically acceptable salt is a sodium salt.

Other examples of pharmaceutically acceptable salts may include hexanoic acid, cyclopentane propionic acid, pyruvic acid, malonic acid, 3-(4-hydroxybenzoyl)benzoic acid, cinnamic acid, 4-chlorobenzenesulphonic acid, 2-naphthalenesulphonic acid, 4-toluenesulphonic acid, camphorsulphonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts may include solvent addition forms (solvates) or crystal forms as defined herein, of the same salt.

Techniques for formulation and administration of the disclosed compounds of the disclosure can be found in *Remington: the Science and Practice of Pharmacy,* $19^{th}$ edition, Mack Publishing Co., Easton, PA (1995). In some embodiments, a crystalline form of Compound 1 or a pharmaceutically acceptable salt thereof, is used in pharmaceutical preparations in combination with one or more pharmaceutically acceptable carrier or diluent. A suitable pharmaceutically acceptable carrier includes, but is not limited to, inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic scheme described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Solid Forms

In some aspects, the present disclosure provides a crystalline form of Compound 1, Compound 1

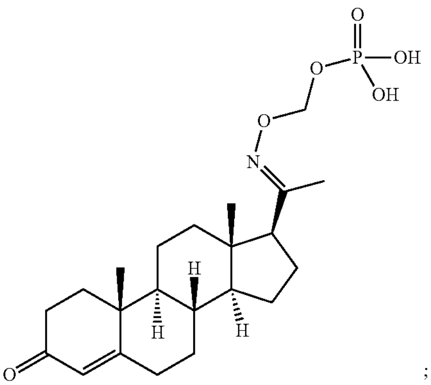

(i.e., ;

(((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy) methyl dihydrogen phosphate)) or a pharmaceutically acceptable salt thereof.

In some aspects, the present disclosure provides a crystalline form of a pharmaceutically acceptable salt of Compound 1.

In some embodiments, the pharmaceutically acceptable salt of Compound 1 is the sodium salt.

In some embodiments, the morphic form of Compound 1 is the bis-tris salt.

In some embodiments, the present disclosure provides a crystalline form of Form I of the bis-tris monohydrate salt of Compound 1.

In some embodiments, the present disclosure provides a crystalline form of Form II of the bis-tris salt of Compound 1.

In some embodiments, the pharmaceutically acceptable salt of Compound 1 is the mono-tris salt.

In some embodiments, the present disclosure provides a crystalline form of Form III of the mono-tris salt of Compound 1.

In some embodiments, the present disclosure provides a crystalline form of Form IV of the mono-tris anhydrous salt of Compound 1.

In some embodiments, the pharmaceutically acceptable salt of Compound 1 is the N-(hydroxyethyl) pyrrolidine salt.

In some embodiments, the pharmaceutically acceptable salt of Compound 1 is the bis-N-(hydroxyethyl) pyrrolidine salt.

In some embodiments, the present disclosure provides a crystalline form of Form V of the bis-N-(hydroxyethyl) pyrrolidine salt of Compound 1.

In some embodiments, the present disclosure provides the amorphous form of Compound 1.

In some embodiments, the crystalline form (e.g., Form I, II, III, IV, or V) has increased solubility relative to the free acid.

In some embodiments, the Form I crystalline form has increased solubility relative to the free acid.

In some embodiments, the Form II crystalline form has increased solubility relative to the free acid.

In some embodiments, the Form III crystalline form has increased solubility relative to the free acid.

In some embodiments, the Form IV crystalline form has increased solubility relative to the free acid.

In some embodiments, the Form V crystalline form has increased solubility relative to the free acid.

In some embodiments, the crystalline form (e.g., Form I, II, III, IV, or V) has increased solubility relative to the amorphous material.

In some embodiments, the Form I crystalline form has increased solubility relative to the amorphous material.

In some embodiments, the Form II crystalline form has increased solubility relative to the amorphous material.

In some embodiments, the Form III crystalline form has increased solubility relative to the amorphous material.

In some embodiments, the Form IV crystalline form has increased solubility relative to the amorphous material.

In some embodiments, the Form V crystalline form has increased solubility relative to the amorphous material.

Form I

X-Ray Power Diffraction (XRPD) Characterizations

In some embodiments, the present application provides a Form I crystalline salt of the bis-tris monohydrate salt of Compound 1 ("Form I") characterized by an X-ray diffraction ("XRPD") pattern comprising peaks at approximately 4.31±0.2, 13.04±0.2, and 17.66±0.2 ° 2θ using Cu Kα radiation. In some embodiments, Form I is characterized by an XRPD pattern comprising peaks at approximately 4.31±0.2, 6.84±0.2, 13.04±0.2, 13.19±0.2, 17.66±0.2, 19.10±0.2, and 21.71±0.2 ° 2θ using Cu Kα radiation.

In some embodiments, the Form I is characterized by an XRPD pattern having at least one peak selected from 4.31±0.2, 13.04±0.2, or 17.66±0.2 ° 2θ (e.g., 4.31±0.1, 13.04±0.1, or 17.66±0.1 ° 2θ (e.g., 4.31, 13.04, or 17.66° 2θ)) using Cu Kα radiation.

In some embodiments, the Form I is characterized by an XRPD pattern having at least two peaks selected from 4.31±0.2, 13.04±0.2, or 17.66±0.2 ° 2θ (e.g., 4.31±0.1, 13.04±0.1, or 17.66±0.1 ° 2θ (e.g., 4.31, 13.04, or 17.66° 2θ)) using Cu Kα radiation.

In some embodiments, the Form I is characterized by an XRPD pattern having at least three peaks selected from 4.31±0.2, 13.04±0.2, 13.19±0.2, or 17.66±0.2 ° 2θ (e.g., 4.31±0.1, 13.04±0.1, 13.19±0.1, or 17.66±0.1 ° 2θ (e.g., 4.31, 13.04, 13.19, or 17.66° 2θ)) using Cu Kα radiation.

In some embodiments, the Form I is characterized by an XRPD pattern having at least four peaks selected from 4.31±0.2, 13.04±0.2, 13.19±0.2, 17.66±0.2, or 19.10±0.2 ° 2θ (e.g., 4.31±0.1, 13.04±0.1, 13.19±0.1, 17.66±0.1, or 19.10±0.1 ° 2θ (e.g., 4.31, 13.04, 13.19, 17.66, or 19.10° 2θ)) using Cu Kα radiation.

In some embodiments, the Form I is characterized by an XRPD pattern having at least five peaks selected from 4.31±0.2, 6.84±0.2, 13.04±0.2, 13.19±0.2, 17.66±0.2, or 19.10±0.2 ° 2θ (e.g., 4.31±0.1, 6.84±0.1, 13.04±0.1, 13.19±0.1, 17.66±0.1, or 19.10±0.1 °2θ (e.g., 4.31, 6.84, 13.04, 13.19, 17.66, or 19.10° 2θ)) using Cu Kα radiation.

In some embodiments, the Form I is characterized by an XRPD pattern having at least six peaks selected from 4.31±0.2, 6.84±0.2, 13.04±0.2, 13.19±0.2, 17.66±0.2, 19.10±0.2, or 21.71±0.2 ° 2θ (e.g., 4.31±0.1, 6.84±0.1, 13.04±0.1, 13.19±0.1, 17.66±0.1, 19.10±0.1, or 21.71±0.1 ° 2θ (e.g., 4.31, 6.84, 13.04, 13.19, 17.66, 19.10, or 21.71° 2θ)) using Cu Kα radiation.

In some embodiments, Form I is characterized by an XRPD pattern comprising peaks at approximately the positions shown in the table below:

TABLE 1

| XRPD peak list for Form I | | |
|---|---|---|
| Pos. [°2θ] | d-spacing [Å] | Rel. Int. [%] |
| 4.33 | 20.407 | 100 |
| 6.86 | 12.881 | 4.3 |
| 8.66 | 10.210 | 4.33 |
| 9.18 | 9.633 | 3.11 |
| 10.85 | 8.151 | 2.69 |
| 13.02 | 6.801 | 9.53 |
| 13.23 | 6.691 | 12.08 |
| 13.75 | 6.442 | 5.12 |
| 14.08 | 6.289 | 1.41 |
| 14.56 | 6.085 | 4.2 |
| 15.35 | 5.773 | 6.22 |
| 15.53 | 5.706 | 12.86 |
| 15.97 | 5.551 | 5.2 |
| 16.41 | 5.402 | 8.1 |
| 16.71 | 5.304 | 17.52 |
| 16.99 | 5.219 | 7.39 |
| 17.37 | 5.106 | 7.05 |
| 17.68 | 5.017 | 50.23 |
| 18.83 | 4.712 | 11.62 |
| 19.12 | 4.641 | 17.39 |
| 19.62 | 4.524 | 14.57 |
| 20.22 | 4.392 | 7.09 |
| 20.63 | 4.306 | 1.1 |
| 21.02 | 4.226 | 1.33 |
| 21.74 | 4.088 | 9.82 |
| 22.74 | 3.910 | 1.84 |
| 23.20 | 3.833 | 4.87 |
| 23.59 | 3.772 | 1.8 |
| 24.24 | 3.671 | 3.34 |
| 24.52 | 3.630 | 2.22 |
| 25.03 | 3.558 | 2.79 |
| 25.45 | 3.500 | 0.75 |
| 25.94 | 3.435 | 1.79 |
| 26.23 | 3.398 | 2.56 |
| 26.57 | 3.355 | 2.29 |
| 27.00 | 3.302 | 4.1 |
| 27.53 | 3.241 | 6.78 |
| 28.02 | 3.184 | 2.03 |
| 28.35 | 3.148 | 3.68 |
| 28.85 | 3.094 | 5.47 |
| 29.14 | 3.065 | 1.69 |
| 29.93 | 2.985 | 5.34 |
| 30.16 | 2.963 | 2.32 |
| 30.84 | 2.899 | 2.52 |
| 31.13 | 2.873 | 3.72 |
| 31.40 | 2.849 | 1.98 |
| 31.79 | 2.815 | 3.73 |
| 32.25 | 2.776 | 3.34 |
| 32.68 | 2.740 | 2.52 |
| 33.79 | 2.653 | 2.4 |
| 34.74 | 2.582 | 0.95 |

In some embodiments, Form I is characterized by an XRPD pattern substantially similar to that set forth in FIG. 1.

Differential Scanning Calorimeter (DSC) Characterizations

In some embodiments, Form I is characterized by an endothermic event with onset at between approximately 45.4° C. and approximately 200.6° C. as measured by DSC.

In some embodiments, Form I is characterized by an endothermic event with onset at approximately 45.4±40° C. as measured by DSC. In some embodiments, Form I is characterized by an endothermic event with onset at approximately 45.4±30° C. as measured by DSC. In some embodiments, Form I is characterized by an endothermic event with onset at approximately 45.4±20° C. as measured by DSC. In some embodiments, Form I is characterized by an endothermic event with onset at approximately 45.4±10° C. as measured by DSC. In some embodiments, Form I is characterized by an endothermic event with onset at approximately 45.4±9° C. as measured by DSC. In some embodiments, Form I is characterized by an endothermic event with onset at approximately 45.4±8° C. as measured by DSC. In some embodiments, Form I is characterized by an endothermic event with onset at approximately 45.4±7° C. as measured by DSC. In some embodiments, Form I is characterized by an endothermic event with onset at approximately 45.4±6° C. as measured by DSC. In some embodiments, Form I is characterized by an endothermic event with onset at approximately 45.4±5° C. as measured by DSC. In some embodiments, Form I is characterized by an endothermic event with onset at approximately 45.4±4° C. as measured by DSC. In some embodiments, Form I is characterized by an endothermic event with onset at approximately 45.4±3° C. as measured by DSC. In some embodiments, Form I is characterized by an endothermic event with onset at approximately 45.4±2° C. as measured by DSC. In some embodiments, Form I is characterized by an endothermic event with onset at approximately 45.4±1° C. as measured by DSC. In some embodiments, Form I is characterized by an endothermic event with onset at approximately 45.4±0.5° C. as measured by DSC.

In some embodiments, Form I is characterized by an endothermic event with onset at approximately 200.6±40° C. as measured by DSC. In some embodiments, Form I is characterized by an endothermic event with onset at approximately 200.6±30° C. as measured by DSC. In some embodiments, Form I is characterized by an endothermic event with onset at approximately 200.6±20° C. as measured by DSC. In some embodiments, Form I is characterized by an endothermic event with onset at approximately 200.6±10° C. as measured by DSC. In some embodiments, Form I is characterized by an endothermic event with onset at approximately 200.6±9° C. as measured by DSC. In some embodiments, Form I is characterized by an endothermic event with onset at approximately 200.6±8° C. as measured by DSC. In some embodiments, Form I is characterized by an endothermic event with onset at approximately 200.6±7° C. as measured by DSC. In some embodiments, Form I is characterized by an endothermic event with onset at approximately 200.6±6° C. as measured by DSC. In some embodiments, Form I is characterized by an endothermic event with onset at approximately 200.6±5° C. as measured by DSC. In some embodiments, Form I is characterized by an endothermic event with onset at approximately 200.6±4° C. as measured by DSC. In some embodiments, Form I is characterized by an endothermic event with onset at approximately 200.6±3° C. as measured by DSC. In some embodiments, Form I is characterized by an endothermic event with onset at approximately 200.6±2° C. as measured by DSC. In some embodiments, Form I is characterized by an endothermic event with onset at approximately 200.6±1° C. as measured by DSC. In some embodiments, Form I is characterized by an endothermic event with onset at approximately 200.6±0.5° C. as measured by DSC.

In some embodiments, Form I is characterized by an endothermic event with onset at approximately 45.4° C. as measured by DSC. In some embodiments, Form I is characterized by an endothermic event with onset at approximately 200.6° C. as measured by DSC.

Thermogravimetric Analysis (TGA) Characterizations

In some embodiments, Form I shows a weight loss of approximately 2.2% between about 25±40° C. and about 60±40° C., as measured by TGA. In some embodiments, Form I shows a weight loss of approximately 2.2% between about 25±30° C. and about 60±30° C., as measured by TGA. In some embodiments, Form I shows a weight loss of approximately 2.2% between about 25±20° C. and about 60±20° C., as measured by TGA. In some embodiments, Form I shows a weight loss of approximately 2.2% between about 25±10° C. and about 60±10° C., as measured by TGA. In some embodiments, Form I shows a weight loss of approximately 2.2% between about 25±9° C. and about 60±9° C., as measured by TGA. In some embodiments, Form I shows a weight loss of approximately 2.2% between about 25±8° C. and about 60±8° C., as measured by TGA. In some embodiments, Form I shows a weight loss of approximately 2.2% between about 25±7° C. and about 60±7° C., as measured by TGA. In some embodiments, Form I shows a weight loss of approximately 2.2% between about 25±6° C. and about 60±6° C., as measured by TGA. In some embodiments, Form I shows a weight loss of approximately 2.2% between about 25±5° C. and about 60±5° C., as measured by TGA. In some embodiments, Form I shows a weight loss of approximately 2.2% between about 25±4° C. and about 60±4° C., as measured by TGA. In some embodiments, Form I shows a weight loss of approximately 2.2% between about 25±3° C. and about 60±3° C., as measured by TGA.

In some embodiments, Form I shows a weight loss of approximately 2.2% between about 25±2° C. and about 60±2° C., as measured by TGA. In some embodiments, Form I shows a weight loss of approximately 2.2% between about 25±1° C. and about 60±1° C., as measured by TGA. In some embodiments, Form I shows a weight loss of approximately 2.2% between about 25±0.5° C. and about 60±0.5° C., as measured by TGA.

In some embodiments, Form I shows a weight loss of approximately 2.2% between about 25° C. and about 60° C., as measured by TGA.

Properties of the Crystalline Form

In some embodiments, Form I is a white solid. In some embodiments, Form I is an off-white solid. In some embodiments, Form I is crystalline.

In some embodiments, Form I is a crystalline white solid. In some embodiments, Form I is a crystalline off-white solid.

Form II

X-Ray Power Diffraction (XRPD) Characterizations

In some embodiments, the present application provides a Form II crystalline salt of the bis-tris salt of Compound 1 ("Form II") characterized by an X-ray diffraction ("XRPD") pattern comprising peaks at approximately 13.51±0.2, 13.69±0.2, and 17.66±0.2 ° 2θ using Cu Kα radiation. In some embodiments, Form II is characterized by an XRPD pattern comprising peaks at approximately 13.51±0.2, 13.69±0.2, 16.74±0.2, 17.23±0.2, 17.66±0.2, 19.89±0.2, and 30.15±0.2 ° 2θ using Cu Kα radiation.

In some embodiments, the Form II is characterized by an XRPD pattern having at least one peak selected from 13.51±0.2, 13.69±0.2, or 17.66±0.2 ° 2θ (e.g., 13.51±0.1, 13.69±0.1, or 17.66±0.1 ° 2θ (e.g., 13.51, 13.69, or 17.66° 20)) using Cu Kα radiation.

In some embodiments, the Form II is characterized by an XRPD pattern having at least two peaks selected from 13.51±0.2, 13.69±0.2, or 17.66±0.2 ° 2θ (e.g., 13.51±0.1, 13.69±0.1, or 17.66=0.1 ° 2θ (e.g., 13.51, 13.69, or 17.66° 20)) using Cu Kα radiation.

In some embodiments, the Form II is characterized by an XRPD pattern having at least three peaks selected from 13.51±0.2, 13.69±0.2, 17.23±0.2, or 17.66±0.2 ° 2θ (e.g., 13.51±0.1, 13.69±0.1, 17.23±0.1, or 17.66±0.1 ° 2θ (e.g., 13.51, 13.69, 17.23, or 17.66° 20)) using Cu Karadiation.

In some embodiments, the Form II is characterized by an XRPD pattern having at least four peaks selected from 13.51±0.2, 13.69±0.2, 17.23±0.2, 17.66±0.2, or 19.89±0.2 ° 2θ (e.g., 13.51±0.1, 13.69±0.1, 17.23±0.1, 17.66±0.1, or 19.89±0.1 ° 2θ (e.g., 13.51, 13.69, 17.23, 17.66, or 19.89° 20)) using Cu Kα radiation.

In some embodiments, the Form II is characterized by an XRPD pattern having at least five peaks selected from 13.51±0.2, 13.69±0.2, 17.23±0.2, 17.66±0.2, 19.89±0.2, or 30.15±0.2 2θ (e.g., 13.51±0.1, 13.69±0.1, 17.23±0.1, 17.66±0.1, 19.89±0.1, or 30.15±0.1 ° 2θ (e.g., 13.51, 13.69, 17.23, 17.66, 19.89, or 30.15° 20)) using Cu Kα radiation.

In some embodiments, the Form II is characterized by an XRPD pattern having at least six peaks selected from 13.51±0.2, 13.69±0.2, 16.74±0.2, 17.23±0.2, 17.66±0.2, 19.89±0.2, or 30.15±0.2 ° 2θ (e.g., 13.51±0.1, 13.69±0.1, 16.74±0.1, 17.23±0.1, 17.66±0.1, 19.89±0.1, or 30.15±0.1 ° 2θ (e.g., 13.51, 13.69, 16.74, 17.23, 17.66, 19.89, or 30.15° 20)) using Cu Kα radiation.

In some embodiments, Form II is characterized by an XRPD pattern comprising peaks at approximately the positions shown in the table below:

TABLE 2

XRPD peak list for Form II

| Pos. [°2θ] | d-spacing [Å] | Rel. Int. [%] |
|---|---|---|
| 34.84 | 2.575 | 43.66 |
| 33.35 | 2.687 | 39.01 |
| 32.44 | 2.760 | 37.49 |
| 31.88 | 2.808 | 45.55 |
| 31.44 | 2.846 | 39.12 |
| 30.95 | 2.890 | 45.08 |
| 30.69 | 2.913 | 42.54 |
| 30.15 | 2.965 | 51.77 |
| 28.90 | 3.089 | 38.06 |
| 27.95 | 3.192 | 44.60 |
| 27.19 | 3.280 | 41.71 |
| 26.64 | 3.347 | 37.00 |
| 25.52 | 3.490 | 27.42 |
| 24.76 | 3.595 | 33.93 |
| 24.05 | 3.701 | 25.41 |
| 23.31 | 3.816 | 26.58 |
| 22.05 | 4.031 | 23.88 |
| 21.57 | 4.120 | 33.13 |
| 20.76 | 4.279 | 33.20 |
| 20.44 | 4.345 | 26.23 |
| 19.89 | 4.464 | 54.90 |
| 19.43 | 4.569 | 37.86 |
| 18.81 | 4.718 | 26.89 |
| 17.66 | 5.022 | 100.00 |
| 17.23 | 5.146 | 59.39 |
| 16.74 | 5.298 | 51.26 |
| 16.37 | 5.414 | 21.24 |
| 15.99 | 5.544 | 13.75 |
| 15.60 | 5.679 | 32.46 |
| 14.91 | 5.942 | 10.93 |
| 14.18 | 6.246 | 34.72 |
| 13.69 | 6.467 | 79.60 |
| 13.51 | 6.555 | 78.46 |
| 10.87 | 8.138 | 8.90 |
| 9.29 | 9.515 | 7.16 |
| 8.51 | 10.395 | 4.22 |
| 7.96 | 11.109 | 3.94 |
| 7.08 | 12.489 | 35.63 |
| 4.27 | 20.672 | 35.06 |

Figure 2:
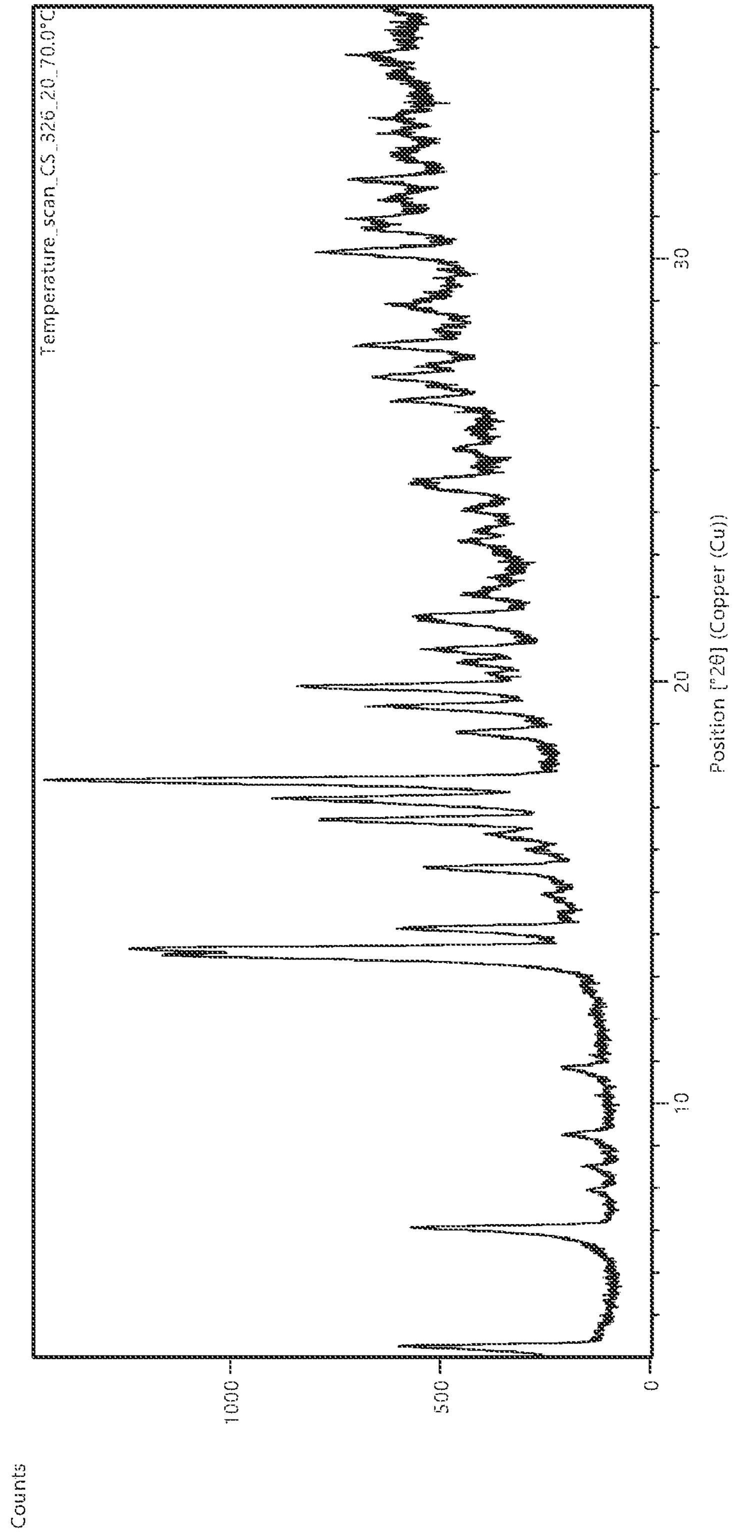
FIG. 2 depicts the XRPD spectrum for Form II.

In some embodiments, Form II is characterized by an XRPD pattern substantially similar to that set forth in FIG. 2.

Properties of the Crystalline Form

In some embodiments, Form II is a white solid. In some embodiments, Form II is crystalline. In some embodiments, Form II is a crystalline white solid.

Form III

X-Ray Power Diffraction (XRPD) Characterizations

In some embodiments, the present application provides a Form III crystalline salt of the mono-tris salt of Compound 1 ("Form III") characterized by an X-ray diffraction ("XRPD") pattern comprising peaks at approximately 15.06±0.2, 18.12±0.2, and 20.76±0.2 ° 2θ using Cu Kα radiation. In some embodiments, Form III is characterized by an XRPD pattern comprising peaks at approximately 4.33±0.2, 14.18±0.2, 14.62±0.2, 15.06±0.2, 18.12±0.2, 20.76±0.2, and 21.93±0.2 ° 2θ using Cu Kα radiation.

In some embodiments, the Form III is characterized by an XRPD pattern having at least one peak selected from 15.06±0.2, 18.12±0.2, or 20.76±0.2 ° 2θ (e.g., 15.06±0.1, 18.12±0.1, or 20.76±0.1 ° 2θ (e.g., 15.06, 18.12, or 20.76° 2θ)) using Cu Kα radiation.

In some embodiments, the Form III is characterized by an XRPD pattern having at least two peaks selected from 15.06±0.2, 18.12±0.2, or 20.76±0.2 ° 2θ (e.g., 15.06=0.1, 18.12±0.1, or 20.76±0.1 ° 2θ (e.g., 15.06, 18.12, or 20.76° 2θ)) using Cu Kα radiation.

In some embodiments, the Form III is characterized by an XRPD pattern having at least three peaks selected from 14.18±0.2, 15.06±0.2, 18.12±0.2, or 20.76±0.2 ° 2θ (e.g., 14.18±0.1, 15.06±0.1, 18.12±0.1, or 20.76±0.1 ° 2θ (e.g., 14.18, 15.06, 18.12, or 20.76° 2θ)) using Cu Kα radiation.

In some embodiments, the Form III is characterized by an XRPD pattern having at least four peaks selected from 14.18±0.2, 15.06±0.2, 18.12±0.2, 20.76±0.2, or 21.93±0.2 ° 2θ (e.g., 14:18±0.1, 15.06±0.1, 18.12±0.1, 20.76±0.1, or 21.93±0.1 ° 2θ (e.g., 14.18, 15.06, 18.12, 20.76, or 21.93° 2θ)) using Cu Kα radiation.

In some embodiments, the Form III is characterized by an XRPD pattern having at least five peaks selected from 14.18±0.2, 14.62±0.2, 15.06±0.2, 18.12±0.2, 20.76±0.2, or 21.93±0.2 ° 2θ (e.g., 14.18±0.1, 14.62±0.1, 15.06±0.1, 18.12±0.1, 20.76±0.1, or 21.93±0.1 ° 2θ (e.g., 14.18, 14.62, 15.06, 18.12, 20.76, or 21.93° 2θ)) using Cu Kα radiation.

In some embodiments, the Form III is characterized by an XRPD pattern having at least six peaks selected from 4.33±0.2, 14.18±0.2, 14.62±0.2, 15.06±0.2, 18.12±0.2, 20.76±0.2, or 21.93±0.2 ° 2θ (e.g., 4.33±0.1, 14.18±0.1, 14.62±0.1, 15.06±0.1, 18.12±0.1, 20.76=0.1, or 21.93±0.1 ° 2θ (e.g., 4.33, 14.18, 14.62, 15.06, 18.12, 20.76, or 21.93° 2θ)) using Cu Kα radiation.

In some embodiments, Form III is characterized by an XRPD pattern comprising peaks at approximately the positions shown in the table below:

TABLE 3

XRPD peak list for Form III

| Pos. [°2θ] | d-spacing [Å] | Rel. Int. [%] |
|---|---|---|
| 4.33 | 20.414 | 11.33 |
| 9.03 | 9.797 | 10.53 |
| 9.71 | 9.113 | 10.71 |
| 10.33 | 8.561 | 1.54 |
| 11.75 | 7.532 | 5 |
| 12.02 | 7.365 | 1.51 |
| 13.95 | 6.347 | 4.82 |
| 14.18 | 6.244 | 14.6 |
| 14.62 | 6.058 | 12.07 |
| 15.06 | 5.884 | 100 |
| 17.03 | 5.206 | 6.15 |
| 17.42 | 5.092 | 1.16 |
| 18.12 | 4.896 | 18.75 |
| 19.00 | 4.672 | 6.58 |
| 19.79 | 4.486 | 8.16 |

TABLE 3-continued

XRPD peak list for Form III

| Pos. [°2θ] | d-spacing [Å] | Rel. Int. [%] |
|---|---|---|
| 20.29 | 4.377 | 1.58 |
| 20.76 | 4.279 | 17.92 |
| 21.19 | 4.193 | 7.13 |
| 21.39 | 4.155 | 4.18 |
| 21.93 | 4.054 | 12.27 |
| 22.36 | 3.976 | 3.31 |
| 23.12 | 3.848 | 0.76 |
| 23.47 | 3.790 | 2.18 |
| 23.74 | 3.748 | 7.41 |
| 24.02 | 3.705 | 4.62 |
| 24.29 | 3.664 | 3.2 |
| 25.11 | 3.547 | 6.92 |
| 25.60 | 3.480 | 2.23 |
| 26.25 | 3.396 | 3.34 |
| 26.70 | 3.338 | 1.33 |
| 27.43 | 3.251 | 0.4 |
| 28.05 | 3.181 | 7.31 |
| 28.56 | 3.126 | 1.62 |
| 29.12 | 3.065 | 5.33 |
| 29.19 | 3.060 | 6.71 |
| 29.50 | 3.028 | 6.28 |
| 30.19 | 2.961 | 6.22 |
| 30.42 | 2.939 | 2.08 |
| 30.92 | 2.892 | 4.48 |
| 31.48 | 2.842 | 3.66 |
| 31.96 | 2.800 | 1.94 |
| 32.18 | 2.781 | 0.98 |
| 32.89 | 2.723 | 0.56 |
| 33.28 | 2.692 | 1.86 |
| 34.42 | 2.606 | 1.75 |

Figure 3:
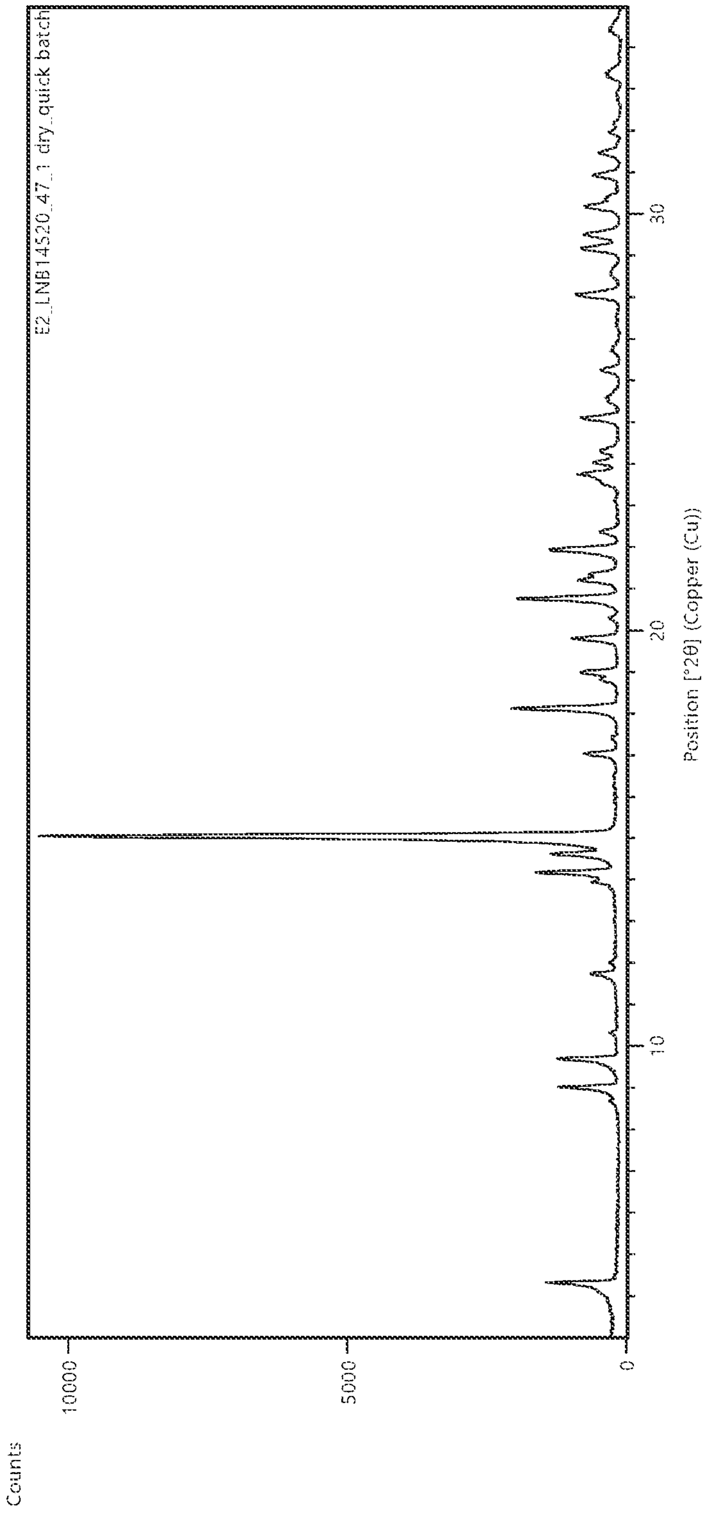
FIG. 3 depicts the XRPD spectrum for Form III.

In some embodiments, Form III is characterized by an XRPD pattern substantially similar to that set forth in FIG. 3.

Differential Scanning Calorimeter (DSC) Characterizations

In some embodiments, Form III is characterized by an endothermic event with onset at approximately 64.1° C. as measured by DSC.

In some embodiments, Form III is characterized by an endothermic event with onset at approximately 64.1±40° C. as measured by DSC. In some embodiments, Form III is characterized by an endothermic event with onset at approximately 64.1±30° C. as measured by DSC. In some embodiments, Form III is characterized by an endothermic event with onset at approximately 64.1±20° C. as measured by DSC. In some embodiments, Form III is characterized by an endothermic event with onset at approximately 64.1±10° C. as measured by DSC. In some embodiments, Form III is characterized by an endothermic event with onset at approximately 64.1±9° C. as measured by DSC. In some embodiments, Form III is characterized by an endothermic event with onset at approximately 64.1±8° C. as measured by DSC. In some embodiments, Form III is characterized by an endothermic event with onset at approximately 64.1±7° C. as measured by DSC. In some embodiments, Form III is characterized by an endothermic event with onset at approximately 64.1±6° C. as measured by DSC. In some embodiments, Form III is characterized by an endothermic event with onset at approximately 64.1±5° C. as measured by DSC. In some embodiments, Form III is characterized by an endothermic event with onset at approximately 64.1±4° C. as measured by DSC. In some embodiments, Form III is characterized by an endothermic event with onset at approximately 64.1±3° C. as measured by DSC. In some embodiments, Form III is characterized by an endothermic event with onset at approximately 64.1±2° C. as measured by DSC. In some embodiments, Form III is characterized by an endothermic event with onset at approximately 64.1±1° C. as measured by DSC. In some embodiments, Form III is characterized by an endothermic event with onset at approximately 64.1±0.5° C. as measured by DSC.

Thermogravimetric Analysis (TGA) Characterizations

In some embodiments, Form III shows a weight loss of approximately 10.7% between about 25±40° C. and about 120±40° C., as measured by TGA. In some embodiments, Form III shows a weight loss of approximately 10.7% between about 25±30° C. and about 120±30° C., as measured by TGA. In some embodiments, Form III shows a weight loss of approximately 10.7% between about 25±20° C. and about 120±20° C., as measured by TGA. In some embodiments, Form III shows a weight loss of approximately 10.7% between about 25±10° C. and about 120±10° C., as measured by TGA. In some embodiments, Form III shows a weight loss of approximately 10.7% between about 25±9° C. and about 120±9° C., as measured by TGA. In some embodiments, Form III shows a weight loss of approximately 10.7% between about 25±8° C. and about 120±8° C., as measured by TGA. In some embodiments, Form III shows a weight loss of approximately 10.7% between about 25±7° C. and about 120±7° C., as measured by TGA. In some embodiments, Form III shows a weight loss of approximately 10.7% between about 25±6° C. and about 120±6° C., as measured by TGA. In some embodiments, Form III shows a weight loss of approximately 10.7% between about 25±5° C. and about 120±5° C., as measured by TGA. In some embodiments, Form III shows a weight loss of approximately 10.7% between about 25±4° C. and about 120±4° C., as measured by TGA. In some embodiments, Form III shows a weight loss of approximately 10.7% between about 25±3° C. and about 120±3° C., as measured by TGA.

In some embodiments, Form III shows a weight loss of approximately 10.7% between about 25±2° C. and about 120±2° C., as measured by TGA. In some embodiments, Form III shows a weight loss of approximately 10.7% between about 25±1° C. and about 120±1° C., as measured by TGA. In some embodiments, Form III shows a weight loss of approximately 10.7% between about 25±0.5° C. and about 120±0.5° C., as measured by TGA.

Properties of the Crystalline Form

In some embodiments, Form III is a white solid. In some embodiments, Form III is crystalline. In some embodiments, Form III is a crystalline white solid.

Form IV

X-Ray Power Diffraction (XRPD) Characterizations

In some embodiments, the present application provides a Form IV crystalline salt of the mono-tris anhydrous salt of Compound 1 ("Form IV") characterized by an X-ray diffraction ("XRPD") pattern comprising peaks at approximately 13.74±0.2, 23.16±0.2, and 25.00±0.2 ° 2θ using Cu Kα radiation. In some embodiments, Form IV is characterized by an XRPD pattern comprising peaks at approximately 13.74±0.2, 14.25±0.2, 20.78±0.2, 21.04±0.2, 23.16±0.2, 25.00±0.2, and 25.14±0.2 ° 2θ using Cu Kα radiation.

In some embodiments, the Form IV is characterized by an XRPD pattern having at least one peak selected from 13.74±0.2, 23.16±0.2, or 25.00±0.2 ° 2θ (e.g., 13.74±0.1, 23.16±0.1, or 25.00±0.1 ° 2θ (e.g., 13.74, 23.16, or 25.00° 2θ)) using Cu Kα radiation.

In some embodiments, the Form IV is characterized by an XRPD pattern having at least two peaks selected from 13.74±0.2, 23.16±0.2, or 25.00±0.2 ° 2θ (e.g., 13.74±0.1, 23.16±0.1, or 25.00±0.1 ° 2θ (e.g., 13.74, 23.16, or 25.00° 2θ)) using Cu Kα radiation.

In some embodiments, the Form IV is characterized by an XRPD pattern having at least three peaks selected from 13.74±0.2, 20.78±0.2, 23.16±0.2, or 25.00±0.2 ° 2θ (e.g., 13.74±0.1, 20.78±0.1, 23.16±0.1, or 25.00±0.1 ° 2θ (e.g., 13.74, 20.78, 23.16, or 25.00° 2θ)) using Cu Kα radiation.

In some embodiments, the Form IV is characterized by an XRPD pattern having at least four peaks selected from 13.74±0.2, 20.78±0.2, 23.16±0.2, 25.00±0.2, or 25.14±0.2 ° 2θ (e.g., 13.74±0.1, 20.78±0.1, 23.16±0.1, 25.00±0.1, or 25.14±0.1 ° 2θ (e.g., 13.74, 20.78, 23.16, 25.00, or 25.14° 2θ)) using Cu Kα radiation.

In some embodiments, the Form IV is characterized by an XRPD pattern having at least five peaks selected from 13.74±0.2, 20.78±0.2, 21.04=0.2, 23.16±0.2, 25.00±0.2, or 25.14±0.2 ° 2θ (e.g., 13.74±0.1, 20.78±0.1, 21.04±0.1, 23.16±0.1, 25.00±0.1, or 25.14±0.1 ° 2θ (e.g., 13.74, 20.78, 21.04, 23.16, 25.00, or 25.14° 2θ)) using Cu Kα radiation.

In some embodiments, the Form IV is characterized by an XRPD pattern having at least six peaks selected from 13.74±0.2, 14.25±0.2, 20.78±0.2, 21.04=0.2, 23.16±0.2, 25.00±0.2, or 25.14±0.2 ° 2θ (e.g., 13.74±0.1, 14.25±0.1, 20.78=0.1, 21.04±0.1, 23.16±0.1, 25.00±0.1, or 25.14±0.1 ° 2θ (e.g., 13.74, 14.25, 20.78, 21.04, 23.16, 25.00, or 25.14° 2θ)) using Cu Kα radiation.

In some embodiments, Form IV is characterized by an XRPD pattern comprising peaks at approximately the positions shown in the table below:

TABLE 4

| XRPD peak list for Form IV | | |
|---|---|---|
| Pos. [°2θ] | d-spacing [Å] | Rel. Int. [%] |
| 3.17 | 27.855 | 9.22 |
| 4.29 | 20.598 | 1.09 |
| 6.36 | 13.894 | 1.00 |
| 12.57 | 7.040 | 8.84 |
| 13.20 | 6.707 | 4.13 |
| 13.74 | 6.446 | 100.00 |
| 14.25 | 6.216 | 13.40 |
| 14.59 | 6.071 | 9.84 |
| 14.89 | 5.950 | 4.72 |
| 15.40 | 5.753 | 5.30 |
| 16.53 | 5.364 | 2.30 |
| 16.90 | 5.245 | 2.28 |
| 17.61 | 5.037 | 1.37 |
| 18.77 | 4.728 | 1.41 |
| 19.18 | 4.628 | 2.92 |
| 32.21 | 2.779 | 5.55 |
| 32.62 | 2.745 | 4.97 |
| 20.78 | 4.274 | 19.70 |
| 21.04 | 4.222 | 16.41 |
| 21.83 | 4.072 | 1.18 |
| 23.16 | 3.840 | 21.71 |
| 23.47 | 3.790 | 10.70 |
| 23.86 | 3.730 | 1.24 |
| 24.24 | 3.672 | 1.20 |
| 25.00 | 3.562 | 24.10 |
| 25.14 | 3.543 | 18.96 |
| 27.02 | 3.299 | 0.91 |
| 27.70 | 3.221 | 1.66 |
| 28.17 | 3.168 | 3.46 |
| 28.73 | 3.108 | 1.90 |
| 29.62 | 3.016 | 0.75 |
| 31.61 | 2.831 | 2.01 |
| 33.30 | 2.691 | 1.19 |
| 34.88 | 2.572 | 3.22 |

Figure 4:
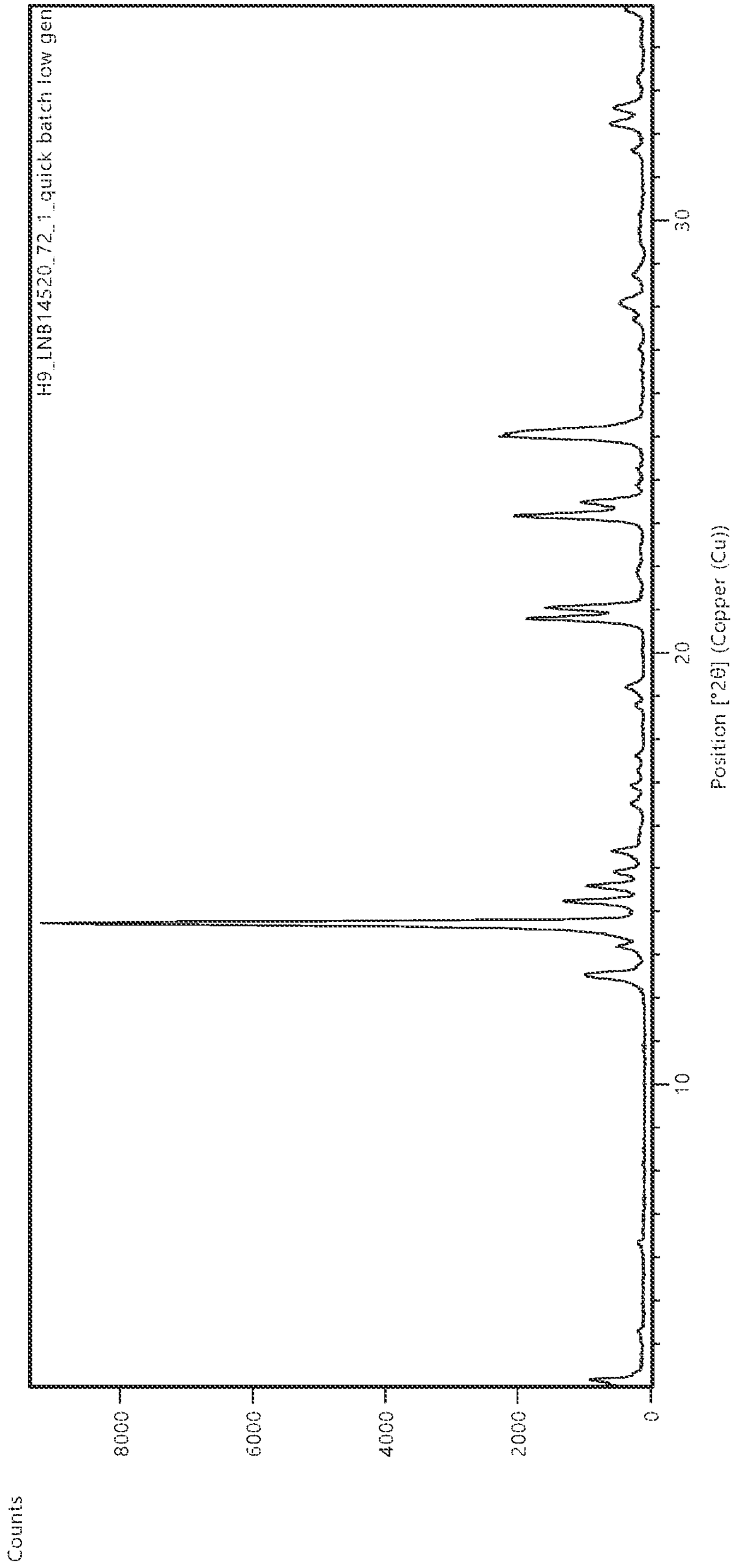
FIG. 4 depicts the XRPD spectrum for Form IV.

In some embodiments, Form IV is characterized by an XRPD pattern substantially similar to that set forth in FIG. 4.

Differential Scanning Calorimeter (DSC) Characterizations

In some embodiments, Form IV is characterized by an endothermic event with onset at approximately 153° C. as measured by DSC.

In some embodiments, Form IV is characterized by an endothermic event with onset at approximately 153±40° C. as measured by DSC. In some embodiments, Form IV is characterized by an endothermic event with onset at approximately 153±30° C. as measured by DSC. In some embodiments, Form IV is characterized by an endothermic event with onset at approximately 153±20° C. as measured by DSC. In some embodiments, Form IV is characterized by an endothermic event with onset at approximately 153±10° C. as measured by DSC. In some embodiments, Form IV is characterized by an endothermic event with onset at approximately 153±9° C. as measured by DSC. In some embodiments, Form IV is characterized by an endothermic event with onset at approximately 153±8° C. as measured by DSC. In some embodiments, Form IV is characterized. by an endothermic event with onset at approximately 153±7° C. as measured by DSC. In some embodiments, Form IV is characterized by an endothermic event with onset at approximately 153±6° C. as measured by DSC. In some embodiments, Form IV is characterized by an endothermic event with onset at approximately 153±5° C. as measured by DSC. In some embodiments, Form IV is characterized by an endothermic event with onset at approximately 153±4° C. as measured by DSC. In some embodiments, Form IV is characterized by an endothermic event with onset at approximately 153±3° C. as measured by DSC. In some embodiments, Form IV is characterized by an endothermic event with onset at approximately 153±2° C. as measured by DSC. In some embodiments, Form IV is characterized by an endothermic event with onset at approximately 153±1° C. as measured by DSC. In some embodiments, Form IV is characterized by an endothermic event with onset at approximately 153±0.5° C. as measured by DSC.

Properties of the Crystalline Form

In some embodiments, Form IV is a white solid. In some embodiments, Form IV is crystalline. In some embodiments, Form IV is a crystalline white solid.

Form V

X-Ray Power Diffraction (XRPD) Characterizations

In some embodiments, the present application provides a Form V crystalline salt of the bis-N-(hydroxyethyl) pyrrolidine salt of Compound 1 ("Form V") characterized by an X-ray diffraction ("XRPD") pattern comprising peaks at approximately 15.07±0.2, 15.65±0.2, and 15.88±0.2 ° 2θ using Cu Kα radiation. In some embodiments, Form V is characterized by an XRPD pattern comprising peaks at approximately 9.62±0.2, 15.07±0.2, 15.65±0.2, 15.88±0.2, 16.13±0.2, 18.01±0.2, and 21.39±0.2 ° 2θ using Cu Kα radiation.

In some embodiments, the Form V is characterized by an XRPD pattern having at least one peak selected from 15.07±0.2, 15.65±0.2, or 15.88±0.2 ° 2θ (e.g., 15.07±0.1, 15.65±0.1, or 15.88±0.1 ° 2θ (e.g., 15.07, 15.65, or 15.88° 2θ)) using Cu Kα radiation.

In some embodiments, the Form V is characterized by an XRPD pattern having at least two peaks selected from 15.07±0.2, 15.65±0.2, or 15.88±0.2 ° 2θ (e.g., 15.07=0.1, 15.65±0.1, or 15.88±0.1 ° 2θ (e.g., 15.07, 15.65, or 15.88° 2θ)) using Cu Kα radiation.

In some embodiments, the Form V is characterized by an XRPD pattern having at least three peaks selected from 15.07±0.2, 15.65±0.2, 15.88±0.2, or 18.01±0.2 ° 2θ (e.g., 15.07±0.1, 15.65±0.1, 15.88±0.1, or 18.01±0.1 ° 2θ (e.g., 15.07, 15.65, 15.88, or 18.01° 2θ)) using Cu Kα radiation.

In some embodiments, the Form V is characterized by an XRPD pattern having at least four peaks selected from 15.07±0.2, 15.65±0.2, 15.88±0.2, 16.13±0.2, or 18.01±0.2 ° 2θ (e.g., 15.07±0.1, 15.65±0.1, 15.88±0.1, 16.13±0.1, or 18.01±0.1 ° 2θ (e.g., 15.07, 15.65, 15.88, 16.13, or 18.01° 2θ)) using Cu Kα radiation.

In some embodiments, the Form V is characterized by an XRPD pattern having at least five peaks selected from 15.07±0.2, 15.65±0.2, 15.88±0.2, 16.13±0.2, 18.01±0.2, or 21.39±0.2 ° 2θ (e.g., 15.07±0.1, 15.65±0.1, 15.88±0.1, 16.13±0.1, 18.01±0.1, or 21.39±0.1 ° 2θ (e.g., 15.07, 15.65, 15.88, 16.13, 18.01, or 21.39° 2θ)) using Cu Kα radiation.

In some embodiments, the Form V is characterized by an XRPD pattern having at least six peaks selected from 9.62±0.2, 15.07±0.2, 15.65±0.2, 15.88±0.2, 16.13±0.2, 18.01±0.2, or 21.39±0.2 ° 2θ (e.g., 9.62±0.1, 15.07±0.1, 15.65±0.1, 15.88±0.1, 16.13±0.1, 18.01±0.1, or 21.39±0.1 ° 2θ (e.g., 9.62, 15.07, 15.65, 15.88, 16.13, 18.01, or 21.39° 2θ)) using Cu Kα radiation.

In some embodiments, Form V is characterized by an XRPD pattern comprising peaks at approximately the positions shown in the table below:

TABLE 5

XRPD peak list for Form V

| Pos. [°2θ] | d-spacing [Å] | Rel. Int. [%] |
|---|---|---|
| 8.67 | 10.195 | 5.85 |
| 9.62 | 9.190 | 17.83 |
| 12.01 | 7.367 | 6.09 |
| 12.53 | 7.064 | 2.57 |
| 13.09 | 6.766 | 3.92 |
| 14.44 | 6.133 | 8.06 |
| 14.60 | 6.066 | 14.12 |
| 15.07 | 5.878 | 71.86 |
| 15.65 | 5.661 | 100.00 |
| 15.88 | 5.580 | 43.95 |
| 16.13 | 5.496 | 22.97 |
| 16.88 | 5.254 | 6.05 |
| 17.43 | 5.089 | 3.90 |
| 18.01 | 4.926 | 26.64 |
| 18.34 | 4.837 | 5.44 |
| 19.03 | 4.664 | 5.26 |
| 19.51 | 4.551 | 5.24 |
| 20.12 | 4.412 | 10.00 |
| 20.64 | 4.304 | 7.24 |
| 20.94 | 4.242 | 3.95 |
| 21.39 | 4.153 | 22.35 |
| 21.87 | 4.064 | 14.76 |
| 22.40 | 3.969 | 4.13 |
| 23.00 | 3.867 | 6.31 |
| 23.54 | 3.780 | 13.21 |
| 23.99 | 3.710 | 6.37 |
| 25.26 | 3.525 | 8.55 |
| 26.60 | 3.352 | 3.71 |
| 26.95 | 3.308 | 3.10 |
| 28.36 | 3.147 | 3.09 |
| 29.35 | 3.044 | 2.83 |
| 31.96 | 2.801 | 2.46 |

Figure 5:
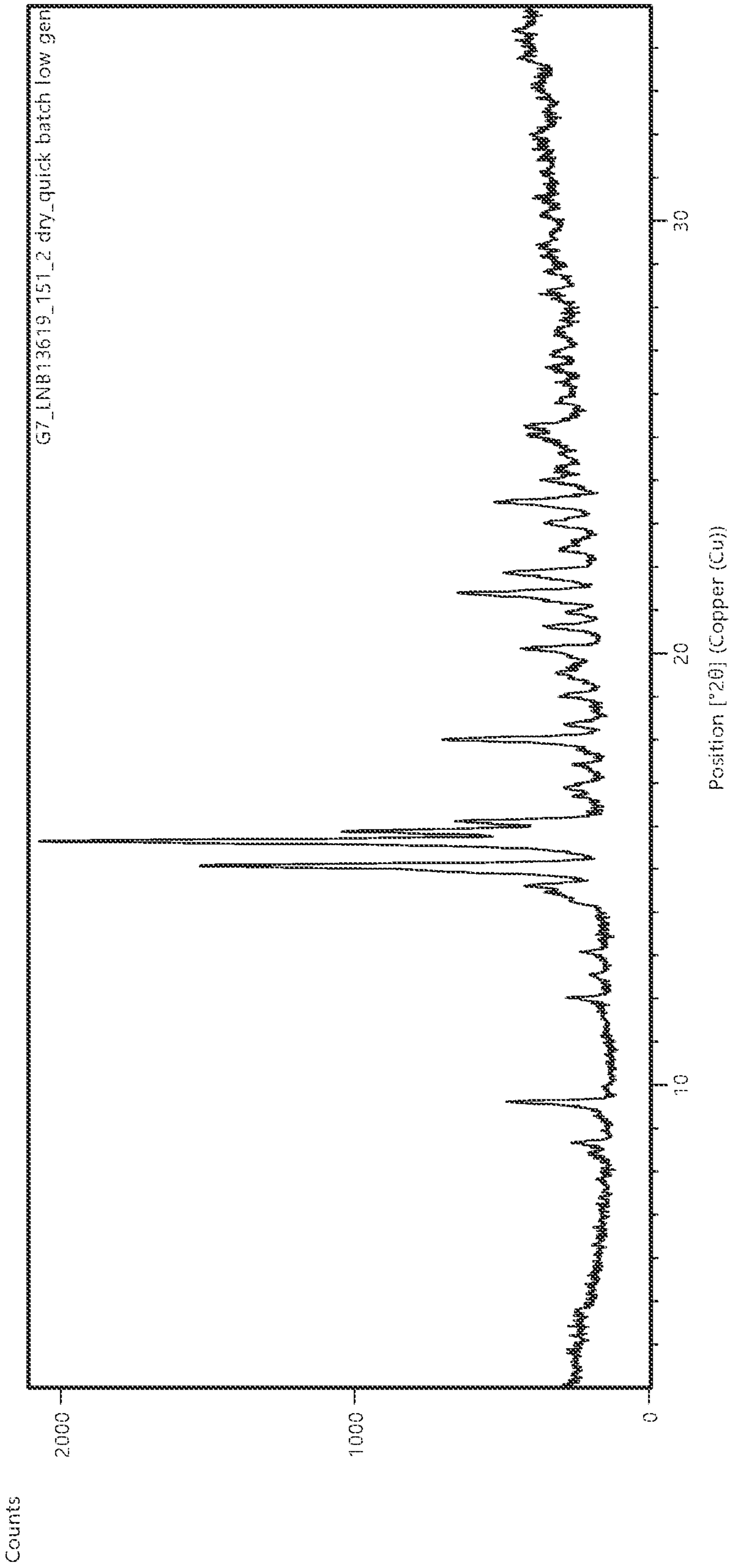
FIG. 5 depicts the XRPD spectrum for Form V.

In some embodiments, Form V is characterized by an XRPD pattern substantially similar to that set forth in FIG. 5.

Differential Scanning Calorimeter (DSC) Characterizations

In some embodiments, Form V is characterized by an endothermic event with onset at approximately 75° C. and approximately 156° C. as measured by DSC. In some embodiments, Form V is characterized by an endothermic event with onset at approximately 75° C. or approximately 156° C. as measured by DSC.

In some embodiments, Form V is characterized by an endothermic event with onset at approximately 75±40° C. as measured by DSC. In some embodiments, Form V is characterized by an endothermic event with onset at approximately 75±30° C. as measured by DSC. In some embodiments, Form V is characterized by an endothermic event with onset at approximately 75±20° C. as measured by DSC. In some embodiments, Form V is characterized by an endothermic event with onset at approximately 75±10° C. as measured by DSC. In some embodiments, Form V is characterized by an endothermic event with onset at approximately 75±9° C. as measured by DSC. In some embodiments, Form V is characterized by an endothermic event with onset at approximately 75±8° C. as measured by DSC. In some embodiments, Form V is characterized by an endothermic event with onset at approximately 75±7° C. as measured by DSC. In some embodiments, Form V is characterized by an endothermic event with onset at approximately 75±6° C. as measured by DSC. In some embodiments, Form V is characterized by an endothermic event with onset at approximately 75±5° C. as measured by DSC. In some embodiments, Form V is characterized by an endothermic event with onset at approximately 75±4° C. as measured by DSC. In some embodiments, Form V is characterized by an endothermic event with onset at approximately 75±3° C. as measured by DSC. In some embodiments, Form V is characterized by an endothermic event with onset at approximately 75±2° C. as measured by DSC. In some embodiments, Form V is characterized by an endothermic event with onset at approximately 75±1° C. as measured by DSC. In some embodiments, Form V is characterized by an endothermic event with onset at approximately 75±0.5° C. as measured by DSC.

In some embodiments, Form V is characterized by an endothermic event with onset at approximately 156±40° C. as measured by DSC. In some embodiments, Form V is characterized by an endothermic event with onset at approximately 156±30° C. as measured by DSC. In some embodiments, Form V is characterized by an endothermic event with onset at approximately 156±20° C. as measured by DSC. In some embodiments, Form V is characterized by an endothermic event with onset at approximately 156±10° C. as measured by DSC. In some embodiments, Form V is characterized by an endothermic event with onset at approximately 156±9° C. as measured by DSC. In some embodiments, Form V is characterized by an endothermic event with onset at approximately 156±8° C. as measured by DSC. In some embodiments, Form V is characterized by an endothermic event with onset at approximately 156±7° C. as measured by DSC. In some embodiments, Form V is characterized by an endothermic event with onset at approximately 156±6° C. as measured by DSC. In some embodiments, Form V is characterized by an endothermic event with onset at approximately 156±5° C. as measured by DSC. In some embodiments, Form V is characterized by an endothermic event with onset at approximately 156±4° C. as measured by DSC. In some embodiments, Form V is characterized by an endothermic event with onset at approximately 156±3° C. as measured by DSC. In some embodiments, Form V is characterized by an endothermic event with onset at approximately 156±2° C. as measured by DSC. In some embodiments, Form V is characterized by an endothermic event with onset at approximately 156±1° C. as measured by DSC. In some embodiments, Form V is characterized by an endothermic event with onset at approximately 156±0.5° C. as measured by DSC.

In some embodiments, Form V is characterized by an endothermic event with onset at approximately 75° C. as measured by DSC. In some embodiments, Form V is characterized by an endothermic event with onset at approximately 156° C. as measured by DSC.

Thermogravimetric Analysis (TGA) Characterizations

In some embodiments, Form V shows a weight loss of approximately 1.8% up to about 65±40° C., as measured by TGA. In some embodiments, Form V shows a weight loss of approximately 1.8% up to about 65±30° C., as measured by TGA. In some embodiments, Form V shows a weight loss of approximately 1.8% up to about 65±20° C., as measured by TGA. In some embodiments, Form V shows a weight loss of approximately 1.8% up to about 65±10° C., as measured by TGA. In some embodiments, Form V shows a weight loss of approximately 1.8% up to about 65±9° C., as measured by TGA. In some embodiments, Form V shows a weight loss of approximately 1.8% up to about 65±8° C., as measured by TGA. In some embodiments, Form V shows a weight loss of approximately 1.8% up to about 65±7° C., as measured by TGA. In some embodiments, Form V shows a weight loss of approximately 1.8% up to about 65±6° C., as measured by TGA. In some embodiments, Form V shows a weight loss of approximately 1.8% up to about 65±5° C., as measured by TGA. In some embodiments, Form V shows a weight loss of approximately 1.8% up to about 65±4° C., as measured by TGA. In some embodiments, Form V shows a weight loss of approximately 1.8% up to about 65±3° C., as measured by TGA.

In some embodiments, Form V shows a weight loss of approximately 1.8% up to about 65±2° C., as measured by TGA. In some embodiments, Form V shows a weight loss of approximately 1.8% up to about 65±1° C., as measured by TGA. In some embodiments, Form V shows a weight loss of approximately 1.8% up to about 65±0.5° C., as measured by TGA.

Properties of the Crystalline Form

In some embodiments, Form V is a white solid. In some embodiments, Form V is crystalline. In some embodiments, Form V is a crystalline white solid.

Tris Salt Composition

In some embodiments, Compound 1A is ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy)methyl dihydrogen phosphate tris salt, (Compound 1A)

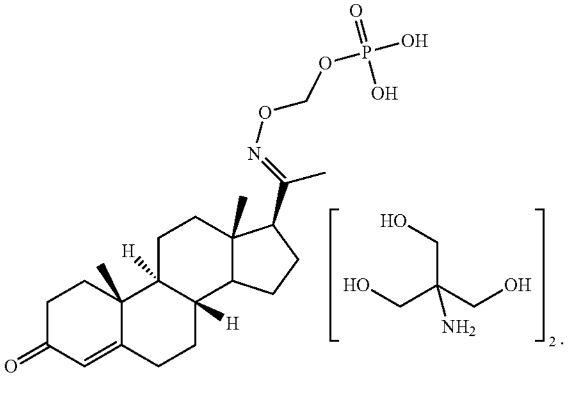

In some aspects, the present disclosure provides a composition comprising ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl) ethylidene)amino)oxy)methyl dihydrogen phosphate tris salt, (Compound 1A)

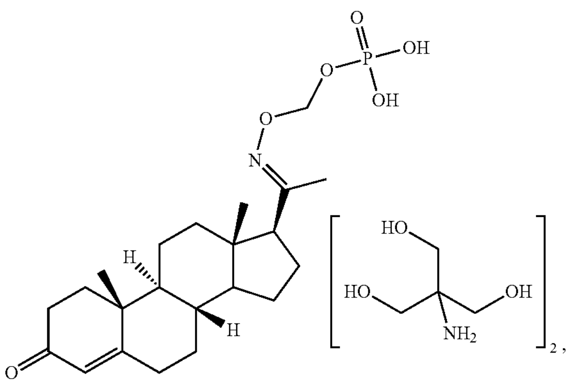

having a purity greater than or equal to about 98.0% as determined by HPLC.

In some aspects, the present disclosure provides a composition comprising Compound 1A, having a purity greater than or equal to about 98.1% as determined by HPLC.

In some aspects, the present disclosure provides a composition comprising Compound 1A, having a purity greater than or equal to about 98.2% as determined by HPLC.

In some aspects, the present disclosure provides a composition comprising Compound 1A, having a purity greater than or equal to about 98.3% as determined by HPLC.

In some aspects, the present disclosure provides a composition comprising Compound 1A, having a purity greater than or equal to about 98.4% as determined by HPLC.

In some aspects, the present disclosure provides a composition comprising Compound 1A, having a purity greater than or equal to about 98.5% as determined by HPLC.

In some aspects, the present disclosure provides a composition comprising Compound 1A, having a purity greater than or equal to about 98.6% as determined by HPLC.

In some aspects, the present disclosure provides a composition comprising Compound 1A, having a purity greater than or equal to about 98.7% as determined by HPLC.

In some aspects, the present disclosure provides a composition comprising Compound 1A, having a purity greater than or equal to about 98.8% as determined by HPLC.

In some aspects, the present disclosure provides a composition comprising Compound 1A, having a purity greater than or equal to about 98.9% as determined by HPLC.

In some aspects, the present disclosure provides a composition comprising Compound 1A, having a purity greater than or equal to about 99.0% as determined by HPLC.

In some aspects, the present disclosure provides a composition comprising Compound 1A, having a purity greater than or equal to about 99.1% as determined by HPLC.

In some aspects, the present disclosure provides a composition comprising Compound 1A, having a purity greater than or equal to about 99.2% as determined by HPLC.

In some aspects, the present disclosure provides a composition comprising Compound 1A, having a purity greater than or equal to about 99.3% as determined by HPLC.

In some aspects, the present disclosure provides a composition comprising Compound 1A, having a purity greater than or equal to about 99.4% as determined by HPLC.

In some aspects, the present disclosure provides a composition comprising Compound 1A, having a purity greater than or equal to about 99.5% as determined by HPLC.

In some aspects, the present disclosure provides a composition comprising Compound 1A, having a purity greater than or equal to about 99.6% as determined by HPLC.

In some aspects, the present disclosure provides a composition comprising Compound 1A, having a purity greater than or equal to about 99.7% as determined by HPLC.

In some aspects, the present disclosure provides a composition comprising Compound 1A, having a purity greater than or equal to about 99.8% as determined by HPLC.

In some aspects, the present disclosure provides a composition comprising Compound 1A, having a purity greater than or equal to about 99.9% as determined by HPLC.

In some embodiments, the composition contains less than 2% of an impurity selected from (Compound A)

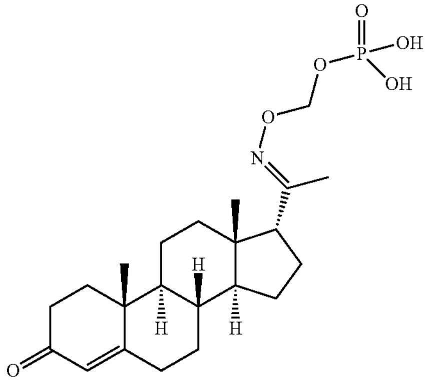

or pharmaceutically acceptable salt thereof, (Compound B)

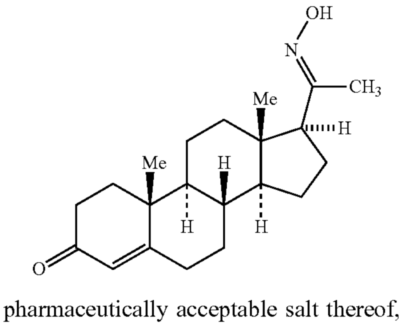

or pharmaceutically acceptable salt thereof, or, and (Compound C)

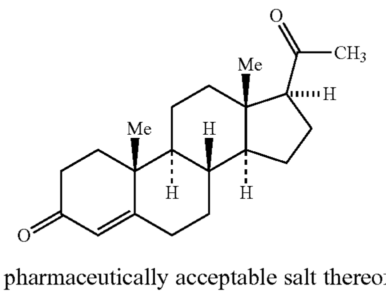

or a pharmaceutically acceptable salt thereof, and combinations thereof.

In some embodiments, Compound A is present by weight from about 0.01% to about 0.5%.

In some embodiments, Compound A is present by weight from about 0.02% to about 0.5%.

In some embodiments, Compound A is present by weight from about 0.03% to about 0.5%.

In some embodiments, Compound A is present by weight from about 0.04% to about 0.5%.

In some embodiments, Compound A is present by weight from about 0.05% to about 0.5%.

In some embodiments, Compound A is present by weight from about 0.06% to about 0.5%.

In some embodiments, Compound A is present by weight from about 0.07% to about 0.5%.

In some embodiments, Compound A is present by weight from about 0.08% to about 0.5%.

In some embodiments, Compound A is present by weight from about 0.09% to about 0.5%.

In some embodiments, Compound A is present by weight from about 0.1% to about 0.5%.

In some embodiments, Compound A is present by weight from about 0.2% to about 0.5%.

In some embodiments, Compound A is present by weight from about 0.3% to about 0.5%.

In some embodiments, Compound A is present by weight from about 0.4% to about 0.5%.

In some embodiments, Compound A is present by weight from about 0.01% to about 0.4%.

In some embodiments, Compound A is present by weight from about 0.01% to about 0.3%.

In some embodiments, Compound A is present by weight from about 0.01% to about 0.2%.

In some embodiments, Compound A is present by weight from about 0.01% to about 0.1%.

In some embodiments, Compound A is present by weight from about 0.01% to about 0.09%.

In some embodiments, Compound A is present by weight from about 0.01% to about 0.08%.

In some embodiments, Compound A is present by weight from about 0.01% to about 0.07%.

In some embodiments, Compound A is present by weight from about 0.01% to about 0.06%.

In some embodiments, Compound A is present by weight from about 0.01% to about 0.05%.

In some embodiments, Compound A is present by weight from about 0.01% to about 0.04%.

In some embodiments, Compound A is present by weight from about 0.01% to about 0.03%.

In some embodiments, Compound A is present by weight from about 0.01% to about 0.02%.

In some embodiments, Compound A is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some embodiments, Compound A is present by weight in about 0.01%.

In some embodiments, Compound A is present by weight in about 0.02%.

In some embodiments, Compound A is present by weight in about 0.03%.

In some embodiments, Compound A is present by weight in about 0.04%.

In some embodiments, Compound A is present by weight in about 0.05%.

In some embodiments, Compound A is present by weight in about 0.06%.

In some embodiments, Compound A is present by weight in about 0.07%.

In some embodiments, Compound A is present by weight in about 0.08%.

In some embodiments, Compound A is present by weight in about 0.09%.

In some embodiments, Compound A is present by weight in about 0.1%.

In some embodiments, Compound A is present by weight in about 0.2%.

In some embodiments, Compound A is present by weight in about 0.3%.

In some embodiments, Compound A is present by weight in about 0.4%.

In some embodiments, Compound A is present by weight in about 0.5%.

In some embodiments, Compound A is present by weight in about 1%.

In some embodiments, Compound A is present by weight in about 1.5%.

In some embodiments, Compound A is present by weight in about 2%.

In some embodiments, Compound B is present by weight from about 0.01% to about 0.5%.

In some embodiments, Compound B is present by weight from about 0.02% to about 0.5%.

In some embodiments, Compound B is present by weight from about 0.03% to about 0.5%.

In some embodiments, Compound B is present by weight from about 0.04% to about 0.5%.

In some embodiments, Compound B is present by weight from about 0.05% to about 0.5%.

In some embodiments, Compound B is present by weight from about 0.06% to about 0.5%.

In some embodiments, Compound B is present by weight from about 0.07% to about 0.5%.

In some embodiments, Compound B is present by weight from about 0.08% to about 0.5%.

In some embodiments, Compound B is present by weight from about 0.09% to about 0.5%.

In some embodiments, Compound B is present by weight from about 0.1% to about 0.5%.

In some embodiments, Compound B is present by weight from about 0.2% to about 0.5%.

In some embodiments, Compound B is present by weight from about 0.3% to about 0.5%.

In some embodiments, Compound B is present by weight from about 0.4% to about 0.5%.

In some embodiments, Compound B is present by weight from about 0.01% to about 0.4%.

In some embodiments, Compound B is present by weight from about 0.01% to about 0.3%.

In some embodiments, Compound B is present by weight from about 0.01% to about 0.2%.

In some embodiments, Compound B is present by weight from about 0.01% to about 0.1%.

In some embodiments, Compound B is present by weight from about 0.01% to about 0.09%.

In some embodiments, Compound B is present by weight from about 0.01% to about 0.08%.

In some embodiments, Compound B is present by weight from about 0.01% to about 0.07%.

In some embodiments, Compound B is present by weight from about 0.01% to about 0.06%.

In some embodiments, Compound B is present by weight from about 0.01% to about 0.05%.

In some embodiments, Compound B is present by weight from about 0.01% to about 0.04%.

In some embodiments, Compound B is present by weight from about 0.01% to about 0.03%.

In some embodiments, Compound B is present by weight from about 0.01% to about 0.02%.

In some embodiments, Compound B is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some embodiments, Compound B is present by weight in about 0.01%.

In some embodiments, Compound B is present by weight in about 0.02%.

In some embodiments, Compound B is present by weight in about 0.03%.

In some embodiments, Compound B is present by weight in about 0.04%.

In some embodiments, Compound B is present by weight in about 0.05%.

In some embodiments, Compound B is present by weight in about 0.06%.

In some embodiments, Compound B is present by weight in about 0.07%.

In some embodiments, Compound B is present by weight in about 0.08%.

In some embodiments, Compound B is present by weight in about 0.09%.

In some embodiments, Compound B is present by weight in about 0.1%.

In some embodiments, Compound B is present by weight in about 0.2%.

In some embodiments, Compound B is present by weight in about 0.3%.

In some embodiments, Compound B is present by weight in about 0.4%.

In some embodiments, Compound B is present by weight in about 0.5%.

In some embodiments, Compound B is present by weight in about 1%.

In some embodiments, Compound B is present by weight in about 1.5%.

In some embodiments, Compound B is present by weight in about 2%.

In some embodiments, Compound C is present by weight from about 0.01% to about 0.5%.

In some embodiments, Compound C is present by weight from about 0.02% to about 0.5%.

In some embodiments, Compound C is present by weight from about 0.03% to about 0.5%.

In some embodiments, Compound C is present by weight from about 0.04% to about 0.5%.

In some embodiments, Compound C is present by weight from about 0.05% to about 0.5%.

In some embodiments, Compound C is present by weight from about 0.06% to about 0.5%.

In some embodiments, Compound C is present by weight from about 0.07% to about 0.5%.

In some embodiments, Compound C is present by weight from about 0.08% to about 0.5%.

In some embodiments, Compound C is present by weight from about 0.09% to about 0.5%.

In some embodiments, Compound C is present by weight from about 0.1% to about 0.5%.

In some embodiments, Compound C is present by weight from about 0.2% to about 0.5%.

In some embodiments, Compound C is present by weight from about 0.3% to about 0.5%.

In some embodiments, Compound C is present by weight from about 0.4% to about 0.5%.

In some embodiments, Compound C is present by weight from about 0.01% to about 0.4%.

In some embodiments, Compound C is present by weight from about 0.01% to about 0.3%.

In some embodiments, Compound C is present by weight from about 0.01% to about 0.2%.

In some embodiments, Compound C is present by weight from about 0.01% to about 0.1%.

In some embodiments, Compound C is present by weight from about 0.01% to about 0.09%.

In some embodiments, Compound C is present by weight from about 0.01% to about 0.08%.

In some embodiments, Compound C is present by weight from about 0.01% to about 0.07%.

In some embodiments, Compound C is present by weight from about 0.01% to about 0.06%.

In some embodiments, Compound C is present by weight from about 0.01% to about 0.05%.

In some embodiments, Compound C is present by weight from about 0.01% to about 0.04%.

In some embodiments, Compound C is present by weight from about 0.01% to about 0.03%.

In some embodiments, Compound C is present by weight from about 0.01% to about 0.02%.

In some embodiments, Compound C is present by weight in about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, or about 0.5%.

In some embodiments, Compound C is present by weight in about 0.01%.

In some embodiments, Compound C is present by weight in about 0.02%.

In some embodiments, Compound C is present by weight in about 0.03%.

In some embodiments, Compound C is present by weight in about 0.04%.

In some embodiments, Compound C is present by weight in about 0.05%.

In some embodiments, Compound C is present by weight in about 0.06%.

In some embodiments, Compound C is present by weight in about 0.07%.

In some embodiments, Compound C is present by weight in about 0.08%.

In some embodiments, Compound C is present by weight in about 0.09%.

In some embodiments, Compound C is present by weight in about 0.1%.

In some embodiments, Compound C is present by weight in about 0.2%.

In some embodiments, Compound C is present by weight in about 0.3%.

In some embodiments, Compound C is present by weight in about 0.4%.

In some embodiments, Compound C is present by weight in about 0.5%.

In some embodiments, Compound C is present by weight in about 1%.

In some embodiments, Compound C is present by weight in about 1.5%.

In some embodiments, Compound C is present by weight in about 2%.

In some aspects, the present disclosure provides a pharmaceutical composition comprising:

a) about 98% ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy)methyl dihydrogen phosphate tris salt, (Compound 1A)

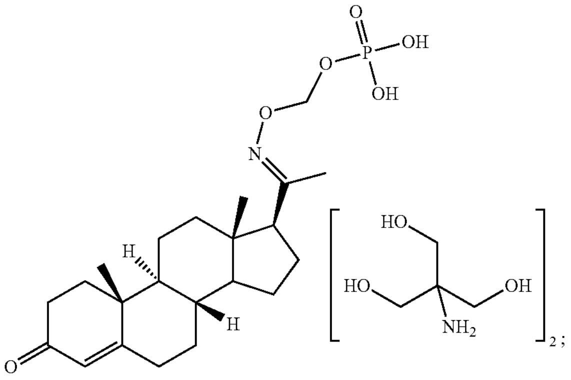

b) up to about 0.1%

(Compound A)

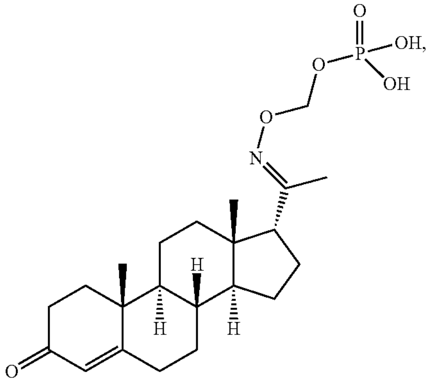

or pharmaceutically acceptable salt thereof;

c) up to about 0.5%

(Compound B)

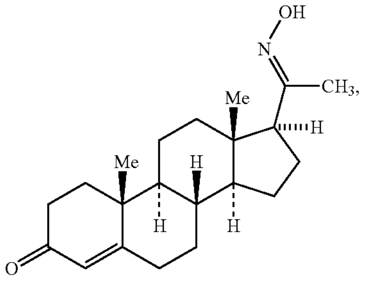

or a pharmaceutically acceptable salt thereof; and d) up to about 0.1%

(Compound C)

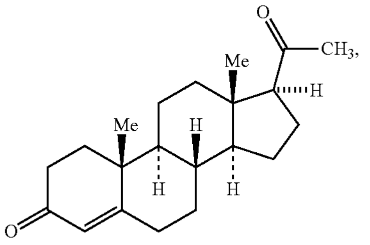

or a pharmaceutically acceptable salt thereof.

In some aspects, the present disclosure provides a pharmaceutical composition comprising about 98% ((((E)-1-((8S,9S,10R,13S,14S,17S)-10,13-dimethyl-3-oxo-2,3,6,7,8,9,10,11,12,13,14,15,16,17-tetradecahydro-1H-cyclopenta[a]phenanthren-17-yl)ethylidene)amino)oxy)methyl dihydrogen phosphate tris salt, (Compound 1A)

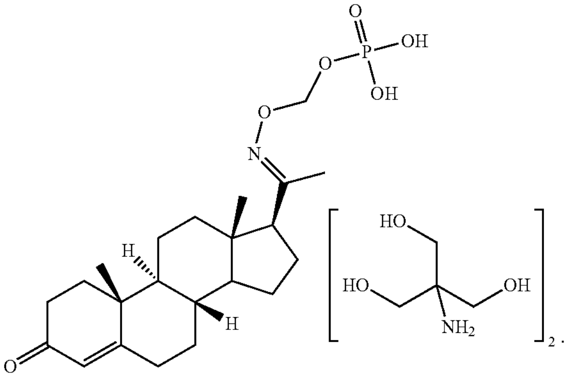

In some aspects, the present disclosure provides a pharmaceutical composition comprising about 97% Compound 1A.

In some aspects, the present disclosure provides a pharmaceutical composition comprising about 97.5% Compound 1A.

In some aspects, the present disclosure provides a pharmaceutical composition comprising about 98% Compound 1A.

In some aspects, the present disclosure provides a pharmaceutical composition comprising about 98.1% Compound 1A.

In some aspects, the present disclosure provides a pharmaceutical composition comprising about 98.2% Compound 1A.

In some aspects, the present disclosure provides a pharmaceutical composition comprising about 98.3% Compound 1A.

In some aspects, the present disclosure provides a pharmaceutical composition comprising about 98.4% Compound 1A.

In some aspects, the present disclosure provides a pharmaceutical composition comprising about 98.5% Compound 1A.

In some aspects, the present disclosure provides a pharmaceutical composition comprising about 98.6% Compound 1A.

In some aspects, the present disclosure provides a pharmaceutical composition comprising about 98.7% Compound 1A.

In some aspects, the present disclosure provides a pharmaceutical composition comprising about 98.8% Compound 1A.

In some aspects, the present disclosure provides a pharmaceutical composition comprising about 98.9% Compound 1A.

In some aspects, the present disclosure provides a pharmaceutical composition comprising about 99% Compound 1A.

In some aspects, the present disclosure provides a pharmaceutical composition comprising about 99.1% Compound 1A.

In some aspects, the present disclosure provides a pharmaceutical composition comprising about 99.2% Compound 1A.

In some aspects, the present disclosure provides a pharmaceutical composition comprising about 99.3% Compound 1A.

In some aspects, the present disclosure provides a pharmaceutical composition comprising about 99.4% Compound 1A.

In some aspects, the present disclosure provides a pharmaceutical composition comprising about 99.5% Compound 1A.

In some aspects, the present disclosure provides a pharmaceutical composition comprising about 99.6% Compound 1A.

In some aspects, the present disclosure provides a pharmaceutical composition comprising about 99.7% Compound 1A.

In some aspects, the present disclosure provides a pharmaceutical composition comprising about 99.8% Compound 1A.

In some aspects, the present disclosure provides a pharmaceutical composition comprising about 99.9% Compound 1A.

In some aspects, the present disclosure provides a pharmaceutical composition comprising up to about 0.1%

(Compound A)

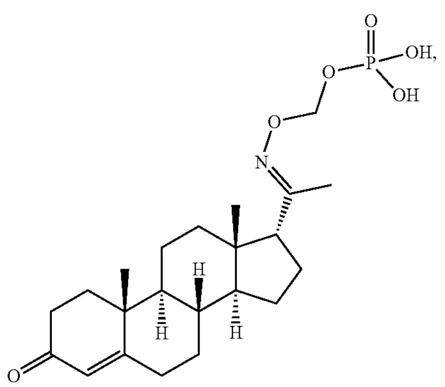

or pharmaceutically acceptable salt thereof.

In some aspects, the present disclosure provides a pharmaceutical composition comprising about 0.1% Compound A, or pharmaceutically acceptable salt thereof.

In some aspects, the present disclosure provides a pharmaceutical composition comprising about 0.09% Compound A, or pharmaceutically acceptable salt thereof.

In some aspects, the present disclosure provides a pharmaceutical composition comprising about 0.08% Compound A, or pharmaceutically acceptable salt thereof.

In some aspects, the present disclosure provides a pharmaceutical composition comprising about 0.07% Compound A, or pharmaceutically acceptable salt thereof.

In some aspects, the present disclosure provides a pharmaceutical composition comprising about 0.06% Compound A, or pharmaceutically acceptable salt thereof.

In some aspects, the present disclosure provides a pharmaceutical composition comprising about 0.05% Compound A, or pharmaceutically acceptable salt thereof.

In some aspects, the present disclosure provides a pharmaceutical composition comprising about 0.04% Compound A, or pharmaceutically acceptable salt thereof.

In some aspects, the present disclosure provides a pharmaceutical composition comprising about 0.03% Compound A, or pharmaceutically acceptable salt thereof.

In some aspects, the present disclosure provides a pharmaceutical composition comprising about 0.02% Compound A, or pharmaceutically acceptable salt thereof.

In some aspects, the present disclosure provides a pharmaceutical composition comprising about 0.01% Compound A, or pharmaceutically acceptable salt thereof.

In some aspects, the present disclosure provides a pharmaceutical composition comprising up to about 0.5%

(Compound B)

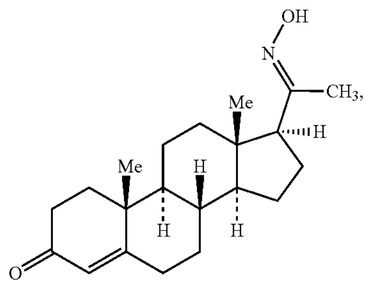

or a pharmaceutically acceptable salt thereof.

In some aspects, the present disclosure provides a pharmaceutical composition comprising about 0.5% Compound B, or a pharmaceutically acceptable salt thereof.

In some aspects, the present disclosure provides a pharmaceutical composition comprising about 0.4% Compound B, or a pharmaceutically acceptable salt thereof.

In some aspects, the present disclosure provides a pharmaceutical composition comprising about 0.3% Compound B, or a pharmaceutically acceptable salt thereof.

In some aspects, the present disclosure provides a pharmaceutical composition comprising about 0.2% Compound B, or a pharmaceutically acceptable salt thereof.

In some aspects, the present disclosure provides a pharmaceutical composition comprising about 0.1% Compound B, or a pharmaceutically acceptable salt thereof.

In some aspects, the present disclosure provides a pharmaceutical composition comprising about 0.09% Compound B, or a pharmaceutically acceptable salt thereof.

In some aspects, the present disclosure provides a pharmaceutical composition comprising about 0.08% Compound B, or a pharmaceutically acceptable salt thereof.

In some aspects, the present disclosure provides a pharmaceutical composition comprising about 0.07% Compound B, or a pharmaceutically acceptable salt thereof.

In some aspects, the present disclosure provides a pharmaceutical composition comprising about 0.06% Compound B, or a pharmaceutically acceptable salt thereof.

In some aspects, the present disclosure provides a pharmaceutical composition comprising about 0.05% Compound B, or a pharmaceutically acceptable salt thereof.

In some aspects, the present disclosure provides a pharmaceutical composition comprising about 0.04% Compound B, or a pharmaceutically acceptable salt thereof.

In some aspects, the present disclosure provides a pharmaceutical composition comprising about 0.03% Compound B, or a pharmaceutically acceptable salt thereof.

In some aspects, the present disclosure provides a pharmaceutical composition comprising about 0.02% Compound B, or a pharmaceutically acceptable salt thereof.

In some aspects, the present disclosure provides a pharmaceutical composition comprising about 0.01% Compound B, or a pharmaceutically acceptable salt thereof.

In some aspects, the present disclosure provides a pharmaceutical composition comprising up to about 0.1%

(Compound C)

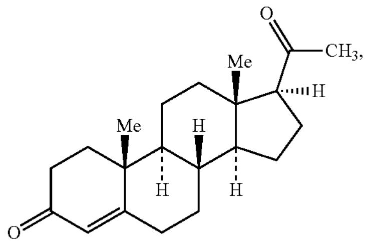

or a pharmaceutically acceptable salt thereof.

In some aspects, the present disclosure provides a pharmaceutical composition comprising about 0.1% Compound C, or a pharmaceutically acceptable salt thereof.

In some aspects, the present disclosure provides a pharmaceutical composition comprising about 0.09% Compound C, or a pharmaceutically acceptable salt thereof.

In some aspects, the present disclosure provides a pharmaceutical composition comprising about 0.08% Compound C, or a pharmaceutically acceptable salt thereof.

In some aspects, the present disclosure provides a pharmaceutical composition comprising about 0.07% Compound C, or a pharmaceutically acceptable salt thereof.

In some aspects, the present disclosure provides a pharmaceutical composition comprising about 0.06% Compound C, or a pharmaceutically acceptable salt thereof.

In some aspects, the present disclosure provides a pharmaceutical composition comprising about 0.05% Compound C, or a pharmaceutically acceptable salt thereof.

In some aspects, the present disclosure provides a pharmaceutical composition comprising about 0.04% Compound C, or a pharmaceutically acceptable salt thereof.

In some aspects, the present disclosure provides a pharmaceutical composition comprising about 0.03% Compound C, or a pharmaceutically acceptable salt thereof.

In some aspects, the present disclosure provides a pharmaceutical composition comprising about 0.02% Compound C, or a pharmaceutically acceptable salt thereof.

In some aspects, the present disclosure provides a pharmaceutical composition comprising about 0.01% Compound C, or a pharmaceutically acceptable salt thereof.

Methods of Preparing the Crystalline Forms

In some aspects, the present disclosure features a method of preparing a crystalline form of Compound 1 or the pharmaceutically acceptable salt thereof described herein.

In some aspects, the present disclosure provides a method of preparing a crystalline form of Compound 1 or the pharmaceutically acceptable salt thereof, comprising one or more steps as described herein.

In some aspects, the present disclosure provides a compound obtainable by, or obtained by, or directly obtained by a method for preparing a crystalline form of Compound 1 or the pharmaceutically acceptable salt thereof as described herein.

The crystalline form of Compound 1 or the pharmaceutically acceptable salt thereof can be prepared by any suitable technique known in the art. Particular processes for the preparation of these compounds are described further in the accompanying examples.

An exemplary preparation of a compound of the application is described in Scheme 1 herein.

Scheme 1

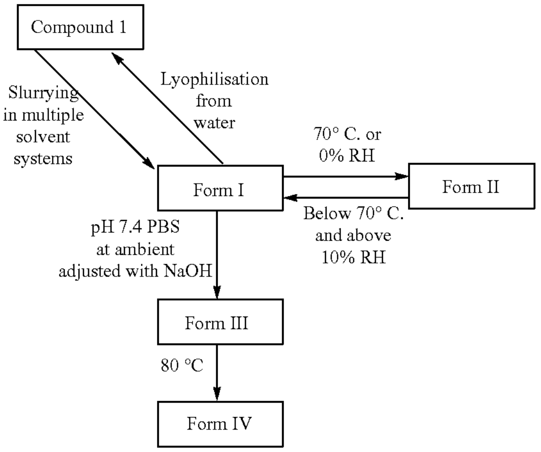

Scheme 1 demonstrates a general synthetic route to the Form I or II of the bis-tris salt of Compound 1 or Form III or IV of the mono-tris salt of Compound 1.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cyclopentylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulphoxides, such as dimethyl sulphoxide (DMSO); nitro compounds, such as nitromethane or nitrobenzene; esters, such as ethyl acetate or methyl acetate, or mixtures of the said solvents or mixtures with water.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between about 5 minutes and about 48 hours.

In some aspects, the present disclosure features a method of preparing a high purity Compound 1A described herein.

In some aspects, the present disclosure provides a method of preparing a high purity Compound 1A, comprising one or more steps as described herein.

In some aspects, the present disclosure provides a compound obtainable by, or obtained by, or directly obtained by a method for preparing a high purity Compound 1A as described herein.

The high purity Compound 1A can be prepared by any suitable technique known in the art. Particular processes for the preparation of these compounds are described further in the accompanying examples.

An exemplary preparation of a compound of the application is described in Scheme A herein.

In some embodiments, Compound 1A is prepared from Intermediate 2, as descried herein. In some embodiments, Compound 1A is purified by seed crystallization in a solvent.

In some embodiments, Compound 1A is purified by seed crystallization with solvent addition. In some embodiments, the solvent is methanol. In some embodiments, the solvent is water. In some embodiments, the solvent is a mixture of methanol and water.

In some embodiments, Compound 1A is prepared on an about 1 to about 2 kilogram scale.

In some embodiments, Compound 1A is prepared on an about 2 kilogram scale. In some embodiments, Compound 1A is prepared on an about 1.75 kilogram scale. In some embodiments, Compound 1A is prepared on an about 1.5 kilogram scale. In some embodiments, Compound 1A is prepared on an about 1.25 kilogram scale. In some embodiments, Compound 1A is prepared on an about 1 kilogram scale. In some embodiments, Compound 1A is prepared on an about 0.75 kilogram scale. In some embodiments, Compound 1A is prepared on an about 0.50 kilogram scale. In some embodiments, Compound 1A is prepared on an about 0.25 kilogram scale. In some embodiments, Compound 1A is prepared on an about 0.1 kilogram scale.

Pharmaceutical Compositions

In some aspects, the present disclosure features pharmaceutical compositions comprising a crystalline form of Compound 1 or the pharmaceutically acceptable salt thereof described herein, and one or more pharmaceutically acceptable carriers or excipients.

In some aspects, the present disclosure features pharmaceutical compositions comprising a crystalline form of Compound 1A or the pharmaceutically acceptable salt thereof described herein, and one or more pharmaceutically acceptable carriers or excipients.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, half-normal saline, bacteriostatic water, Cremophor EL™ (BASF, Parsippany, N.J.), dextrose 5% in water (D5 or DSW) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It may be especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease and also preferably causing complete regression of the disease.

It is understood that the pharmaceutical compositions can be included in a container, pack, or dispenser together with instructions for administration.

Methods of Use

In some aspects, the present disclosure provides a method of preventing or treating a disease in a subject, comprising administering to the subject a pharmaceutically effective amount of a crystalline form of Compound 1 or the pharmaceutically acceptable salt thereof described herein.

In some aspects, the present disclosure provides a method of treating a disease in a subject, comprising administering to the subject a pharmaceutically effective amount of a crystalline form of Compound 1 or the pharmaceutically acceptable salt thereof described herein.

In some aspects, the present disclosure provides a method of preventing or treating a disease in a subject, comprising administering to the subject a crystalline form of Compound 1 or the pharmaceutically acceptable salt thereof described herein.

In some aspects, the present disclosure provides a method of treating a disease in a subject, comprising administering to the subject a crystalline form of Compound 1 or the pharmaceutically acceptable salt thereof described herein.

In some aspects, the present disclosure provides a crystalline form of Compound 1 or the pharmaceutically acceptable salt thereof described herein for use in preventing or treating a disease in a subject.

In some aspects, the present disclosure provides a crystalline form of Compound 1 or the pharmaceutically acceptable salt thereof described herein for use in treating a disease in a subject.

In some aspects, the present disclosure provides use of a crystalline form of Compound 1 or the pharmaceutically acceptable salt thereof described herein in the manufacture of a medicament for preventing or treating a disease in a subject.

In some aspects, the present disclosure provides use of a crystalline form of Compound 1 or the pharmaceutically acceptable salt thereof described herein in the manufacture of a medicament for treating a disease in a subject.

In some aspects, the present disclosure provides use of a crystalline form of Compound 1 or the pharmaceutically acceptable salt thereof described herein for preventing or treating a disease in a subject.

In some aspects, the present disclosure provides use of a crystalline form of Compound 1 or the pharmaceutically acceptable salt thereof described herein for treating a disease in a subject.

In some aspects, the present disclosure provides a method of preventing or treating a disease in a subject, comprising administering to the subject a pharmaceutically effective amount of Form I crystalline salt.

In some aspects, the present disclosure provides a method of treating a disease in a subject, comprising administering to the subject a pharmaceutically effective amount of Form I crystalline salt.

In some aspects, the present disclosure provides a method of preventing or treating a disease in a subject, comprising administering to the subject the Form I crystalline salt.

In some aspects, the present disclosure provides a method of treating a disease in a subject, comprising administering to the subject the Form I crystalline salt.

In some aspects, the present disclosure provides Form I crystalline salt for use in preventing or treating a disease in a subject.

In some aspects, the present disclosure provides Form I crystalline salt for use in treating a disease in a subject.

In some aspects, the present disclosure provides use of Form I crystalline salt in the manufacture of a medicament for preventing or treating a disease in a subject.

In some aspects, the present disclosure provides use of Form I crystalline salt in the manufacture of a medicament for treating a disease in a subject.

In some aspects, the present disclosure provides use of Form I crystalline salt for preventing or treating a disease in a subject.

In some aspects, the present disclosure provides use of Form I crystalline salt for treating a disease in a subject.

In some aspects, the present disclosure provides a method of preventing or treating a disease in a subject, comprising administering to the subject the Form II crystalline salt.

In some aspects, the present disclosure provides a method of treating a disease in a subject, comprising administering to the subject the Form II crystalline salt.

In some aspects, the present disclosure provides a method of preventing or treating a disease in a subject, comprising administering to the subject a pharmaceutically effective amount of Form II crystalline salt.

In some aspects, the present disclosure provides a method of treating a disease in a subject, comprising administering to the subject a pharmaceutically effective amount of Form II crystalline salt.

In some aspects, the present disclosure provides Form II crystalline salt for use in preventing or treating a disease in a subject.

In some aspects, the present disclosure provides Form II crystalline salt for use in treating a disease in a subject.

In some aspects, the present disclosure provides use of Form II crystalline salt in the manufacture of a medicament for preventing or treating a disease in a subject.

In some aspects, the present disclosure provides use of Form II crystalline salt in the manufacture of a medicament for treating a disease in a subject.

In some aspects, the present disclosure provides use of Form II crystalline salt for preventing or treating a disease in a subject.

In some aspects, the present disclosure provides use of Form II crystalline salt for treating a disease in a subject.

In some aspects, the present disclosure provides a method of preventing or treating a disease in a subject, comprising administering to the subject a pharmaceutically effective amount of Form III crystalline salt.

In some aspects, the present disclosure provides a method of treating a disease in a subject, comprising administering to the subject a pharmaceutically effective amount of Form III crystalline salt.

In some aspects, the present disclosure provides a method of preventing or treating a disease in a subject, comprising administering to the subject the Form III crystalline salt.

In some aspects, the present disclosure provides a method of treating a disease in a subject, comprising administering to the subject the Form III crystalline salt.

In some aspects, the present disclosure provides Form III crystalline salt for use in preventing or treating a disease in a subject.

In some aspects, the present disclosure provides Form III crystalline salt for use in treating a disease in a subject.

In some aspects, the present disclosure provides use of Form III crystalline salt in the manufacture of a medicament for preventing or treating a disease in a subject.

In some aspects, the present disclosure provides use of Form III crystalline salt in the manufacture of a medicament for treating a disease in a subject.

In some aspects, the present disclosure provides use of Form III crystalline salt for preventing or treating a disease in a subject.

In some aspects, the present disclosure provides use of Form III crystalline salt for treating a disease in a subject.

In some aspects, the present disclosure provides a method of preventing or treating a disease in a subject, comprising administering to the subject a pharmaceutically effective amount of Form IV crystalline salt.

In some aspects, the present disclosure provides a method of treating a disease in a subject, comprising administering to the subject a pharmaceutically effective amount of Form IV crystalline salt.

In some aspects, the present disclosure provides a method of preventing or treating a disease in a subject, comprising administering to the subject the Form IV crystalline salt.

In some aspects, the present disclosure provides a method of treating a disease in a subject, comprising administering to the subject the Form IV crystalline salt.

In some aspects, the present disclosure provides Form IV crystalline salt for use in preventing or treating a disease in a subject.

In some aspects, the present disclosure provides Form IV crystalline salt for use in treating a disease in a subject.

In some aspects, the present disclosure provides use of Form IV crystalline salt in the manufacture of a medicament for preventing or treating a disease in a subject.

In some aspects, the present disclosure provides use of Form IV crystalline salt in the manufacture of a medicament for treating a disease in a subject.

In some aspects, the present disclosure provides use of Form IV crystalline salt for preventing or treating a disease in a subject.

In some aspects, the present disclosure provides use of Form IV crystalline salt for treating a disease in a subject.

In some aspects, the present disclosure provides a method of preventing or treating a disease in a subject, comprising administering to the subject a pharmaceutically effective amount of Form V crystalline salt.

In some aspects, the present disclosure provides a method of treating a disease in a subject, comprising administering to the subject a pharmaceutically effective amount of Form V crystalline salt.

In some aspects, the present disclosure provides a method of preventing or treating a disease in a subject, comprising administering to the subject the Form V crystalline salt.

In some aspects, the present disclosure provides a method of treating a disease in a subject, comprising administering to the subject the Form V crystalline salt.

In some aspects, the present disclosure provides Form V crystalline salt for use in preventing or treating a disease in a subject.

In some aspects, the present disclosure provides Form V crystalline salt for use in treating a disease in a subject.

In some aspects, the present disclosure provides use of Form V crystalline salt in the manufacture of a medicament for preventing or treating a disease in a subject.

In some aspects, the present disclosure provides use of Form V crystalline salt in the manufacture of a medicament for treating a disease in a subject.

In some aspects, the present disclosure provides use of Form V crystalline salt for preventing or treating a disease in a subject.

In some aspects, the present disclosure provides use of Form V crystalline salt for treating a disease in a subject.

In some aspects, the present disclosure provides a method of preventing or treating a disease in a subject, comprising administering to the subject a pharmaceutically effective amount of a composition of Compound 1A.

In some aspects, the present disclosure provides a method of treating a disease in a subject, comprising administering to the subject a pharmaceutically effective amount of a composition of Compound 1A.

In some aspects, the present disclosure provides a method of preventing or treating a disease in a subject, comprising administering to the subject a composition of Compound 1A.

In some aspects, the present disclosure provides a method of treating a disease in a subject, comprising administering to the subject a composition of Compound 1A, In some aspects, the present disclosure provides a composition of Compound 1A for use in preventing or treating a disease in a subject.

In some aspects, the present disclosure provides a composition of Compound 1A for use in treating a disease in a subject.

In some aspects, the present disclosure provides use of a composition of Compound 1A in the manufacture of a medicament for preventing or treating a disease in a subject.

In some aspects, the present disclosure provides use of a composition of Compound 1A in the manufacture of a medicament for treating a disease in a subject.

In some aspects, the present disclosure provides use of a composition of Compound 1A for preventing or treating a disease in a subject.

In some aspects, the present disclosure provides use of a composition of Compound 1A for treating a disease in a subject.

In some embodiments, the disease or disorder is a neurodegenerative disease or disorder.

In some embodiments, the disease or disorder is a stroke or a traumatic brain injury.

In some embodiments, the disease or disorder is a stroke.

In some embodiments, the disease or disorder is a traumatic brain injury.

In some embodiments, the disease or disorder is a symptom of a stroke or a traumatic brain injury.

In some embodiments, the disease or disorder is a symptom of stroke.

In some embodiments, the disease or disorder is a symptom of a traumatic brain injury.

In some embodiments, the disease or disorder is progression of a stroke or a traumatic brain injury.

In some embodiments, the disease or disorder is progression of stroke.

In some embodiments, the disease or disorder is progression of a traumatic brain injury.

In some embodiments, the disease or disorder is an edema of a stroke or a traumatic brain injury.

In some embodiments, the disease or disorder is an edema of stroke.

In some embodiments, the disease or disorder is an edema of a traumatic brain injury.

In some embodiments, the disease or disorder is frontal lobe dementia.

In some embodiments, the disease or disorder is a neurodegenerative disease.

In some embodiments, the neurodegenerative disease is multiple sclerosis, Parkinson's disease, Alzheimer's disease, Huntington's Disease, Lewy body disease, amyotrophic lateral sclerosis, or synucleinopathy.

In some aspects, the present disclosure features a method of managing inflammation in a subject, (e.g., in vitro or in vivo), comprising contacting a cell with an effective amount of a crystalline form of Compound 1 or a pharmaceutically acceptable salt thereof.

In some aspects, the present disclosure features a method of managing inflammation in a subject, comprising administering to the subject a pharmaceutically effective amount of a crystalline form of Compound 1 or a pharmaceutically acceptable salt thereof described herein.

In some aspects, the present disclosure features a crystalline form of Compound 1 or the pharmaceutically acceptable salt thereof described herein for use in managing inflammation in a subject, (e.g., in vitro or in vivo), comprising contacting a cell with an effective amount of a crystalline form of Compound 1 or a pharmaceutically acceptable salt thereof.

In some aspects, the present disclosure features a method of managing inflammation in a subject, (e.g., in vitro or in vivo), comprising contacting a cell with a crystalline form of Compound 1 or a pharmaceutically acceptable salt thereof.

In some aspects, the present disclosure features a method of managing inflammation in a subject, comprising administering to the subject a crystalline form of Compound 1 or a pharmaceutically acceptable salt thereof described herein.

In some aspects, the present disclosure features a crystalline form of Compound 1 or the pharmaceutically acceptable salt thereof described herein for use in managing inflammation in a subject, (e.g., in vitro or in vivo), comprising contacting a cell with a crystalline form of Compound 1 or a pharmaceutically acceptable salt thereof.

In some aspects, the present disclosure features a crystalline form of Compound 1 or a pharmaceutically acceptable salt thereof described herein for use in managing inflammation in a subject.

In some aspects, the present disclosure features use of a crystalline form of Compound 1 or a pharmaceutically acceptable salt thereof described herein in the manufacture of a medicament for managing inflammation (e.g., in vitro or in vivo).

In some aspects, the present disclosure features use of a crystalline form of Compound 1 or a pharmaceutically acceptable salt thereof described herein in the manufacture of a medicament for managing inflammation in a subject.

In some aspects, the present disclosure features use of a crystalline form of Compound 1 or a pharmaceutically acceptable salt thereof described herein for managing inflammation (e.g., in vitro or in vivo).

In some aspects, the present disclosure features use of a crystalline form of Compound 1 or a pharmaceutically acceptable salt thereof described herein for managing inflammation in a subject.

In some aspects, the present disclosure features a method of managing inflammation in a subject, (e.g., in vitro or in vivo), comprising contacting a cell with an effective amount of Form I crystalline form described herein.

In some aspects, the present disclosure features a method of managing inflammation in a subject, comprising administering to the subject a pharmaceutically effective amount of Form I crystalline form described herein.

In some aspects, the present disclosure features Form I crystalline form described herein for use in managing inflammation in a subject, (e.g., in vitro or in vivo), comprising contacting a cell with an effective amount of Form I crystalline form.

In some aspects, the present disclosure features a method of managing inflammation in a subject, (e.g., in vitro or in vivo), comprising contacting a cell with the Form I crystalline form described herein.

In some aspects, the present disclosure features a method of managing inflammation in a subject, comprising administering to the subject the Form I crystalline form described herein.

In some aspects, the present disclosure features Form I crystalline form described herein for use in managing inflammation in a subject, (e.g., in vitro or in vivo), comprising contacting a cell with the Form I crystalline form.

In some aspects, the present disclosure features Form I crystalline form described herein for use in managing inflammation in a subject.

In some aspects, the present disclosure features use of Form I crystalline form described herein in the manufacture of a medicament for managing inflammation (e.g., in vitro or in vivo).

In some aspects, the present disclosure features use of Form I crystalline form described herein in the manufacture of a medicament for managing inflammation in a subject.

In some aspects, the present disclosure features use of Form I crystalline form described herein for managing inflammation (e.g., in vitro or in vivo).

In some aspects, the present disclosure features use of Form I crystalline form described herein for managing inflammation in a subject.

In some aspects, the present disclosure features a method of managing inflammation in a subject, (e.g., in vitro or in vivo), comprising contacting a cell with an effective amount of Form II crystalline form described herein.

In some aspects, the present disclosure features a method of managing inflammation in a subject, comprising administering to the subject a pharmaceutically effective amount of Form II crystalline form described herein.

In some aspects, the present disclosure features Form II crystalline form described herein for use in managing inflammation in a subject, (e.g., in vitro or in vivo), comprising contacting a cell with an effective amount of Form II crystalline form.

In some aspects, the present disclosure features a method of managing inflammation in a subject, (e.g., in vitro or in vivo), comprising contacting a cell with the Form II crystalline form described herein.

In some aspects, the present disclosure features a method of managing inflammation in a subject, comprising administering to the subject the Form II crystalline form described herein.

In some aspects, the present disclosure features Form II crystalline form described herein for use in managing inflammation in a subject, (e.g., in vitro or in vivo), comprising contacting a cell with the Form II crystalline form.

In some aspects, the present disclosure features Form II crystalline form described herein for use in managing inflammation in a subject.

In some aspects, the present disclosure features use of Form II crystalline form described herein in the manufacture of a medicament for managing inflammation (e.g., in vitro or in vivo).

In some aspects, the present disclosure features use of Form II crystalline form described herein in the manufacture of a medicament for managing inflammation in a subject.

In some aspects, the present disclosure features use of Form II crystalline form described herein for managing inflammation (e.g., in vitro or in vivo).

In some aspects, the present disclosure features use of Form II crystalline form described herein for managing inflammation in a subject.

In some aspects, the present disclosure features a method of managing inflammation in a subject, (e.g., in vitro or in vivo), comprising contacting a cell with an effective amount of Form III crystalline form described herein.

In some aspects, the present disclosure features a method of managing inflammation in a subject, comprising administering to the subject a pharmaceutically effective amount of Form III crystalline form described herein.

In some aspects, the present disclosure features Form III crystalline form described herein for use in managing inflammation in a subject, (e.g., in vitro or in vivo), comprising contacting a cell with an effective amount of Form III crystalline form.

In some aspects, the present disclosure features a method of managing inflammation in a subject, (e.g., in vitro or in vivo), comprising contacting a cell with the Form III crystalline form described herein.

In some aspects, the present disclosure features a method of managing inflammation in a subject, comprising administering to the subject the Form III crystalline form described herein.

In some aspects, the present disclosure features Form III crystalline form described herein for use in managing inflammation in a subject, (e.g., in vitro or in vivo), comprising contacting a cell with the of Form III crystalline form.

In some aspects, the present disclosure features Form III crystalline form described herein for use in managing inflammation in a subject.

In some aspects, the present disclosure features use of Form III crystalline form described herein in the manufacture of a medicament for managing inflammation (e.g., in vitro or in vivo).

In some aspects, the present disclosure features use of Form III crystalline form described herein in the manufacture of a medicament for managing inflammation in a subject.

In some aspects, the present disclosure features use of Form III crystalline form described herein for managing inflammation (e.g., in vitro or in vivo).

In some aspects, the present disclosure features use of Form III crystalline form described herein for managing inflammation in a subject.

In some aspects, the present disclosure features a method of managing inflammation in a subject, (e.g., in vitro or in vivo), comprising contacting a cell with an effective amount of Form IV crystalline form described herein.

In some aspects, the present disclosure features a method of managing inflammation in a subject, comprising administering to the subject a pharmaceutically effective amount of Form IV crystalline form described herein.

In some aspects, the present disclosure features Form IV crystalline form described herein for use in managing inflammation in a subject, (e.g., in vitro or in vivo), comprising contacting a cell with an effective amount of Form IV crystalline form.

In some aspects, the present disclosure features a method of managing inflammation in a subject, (e.g., in vitro or in vivo), comprising contacting a cell with the Form IV crystalline form described herein.

In some aspects, the present disclosure features a method of managing inflammation in a subject, comprising administering to the subject the Form IV crystalline form described herein.

In some aspects, the present disclosure features Form IV crystalline form described herein for use in managing inflammation in a subject, (e.g., in vitro or in vivo), comprising contacting a cell with the Form IV crystalline form.

In some aspects, the present disclosure features Form IV crystalline form described herein for use in managing inflammation in a subject.

In some aspects, the present disclosure features use of Form IV crystalline form described herein in the manufacture of a medicament for managing inflammation (e.g., in vitro or in vivo).

In some aspects, the present disclosure features use of Form IV crystalline form described herein in the manufacture of a medicament for managing inflammation in a subject.

In some aspects, the present disclosure features use of Form IV crystalline form described herein for managing inflammation (e.g., in vitro or in vivo).

In some aspects, the present disclosure features use of Form IV crystalline form described herein for managing inflammation in a subject.

In some aspects, the present disclosure features a method of managing inflammation in a subject, (e.g., in vitro or in vivo), comprising contacting a cell with an effective amount of Form V crystalline form described herein.

In some aspects, the present disclosure features a method of managing inflammation in a subject, comprising administering to the subject a pharmaceutically effective amount of Form V crystalline form described herein.

In some aspects, the present disclosure features Form V crystalline form described herein for use in managing inflammation in a subject, (e.g., in vitro or in vivo), comprising contacting a cell with an effective amount of Form V crystalline form.

In some aspects, the present disclosure features a method of managing inflammation in a subject, (e.g., in vitro or in vivo), comprising contacting a cell with the Form V crystalline form described herein.

In some aspects, the present disclosure features a method of managing inflammation in a subject, comprising administering to the subject the Form V crystalline form described herein.

In some aspects, the present disclosure features Form V crystalline form described herein for use in managing inflammation in a subject, (e.g., in vitro or in vivo), comprising contacting a cell with the Form V crystalline form.

In some aspects, the present disclosure features Form V crystalline form described herein for use in managing inflammation in a subject.

In some aspects, the present disclosure features use of Form V crystalline form described herein in the manufacture of a medicament for managing inflammation (e.g., in vitro or in vivo).

In some aspects, the present disclosure features use of Form V crystalline form described herein in the manufacture of a medicament for managing inflammation in a subject.

In some aspects, the present disclosure features use of Form V crystalline form described herein for managing inflammation (e.g., in vitro or in vivo).

In some aspects, the present disclosure features use of Form V crystalline form described herein for managing inflammation in a subject.

In some aspects, the present disclosure features a method of managing inflammation in a subject, (e.g., in vitro or in vivo), comprising contacting a cell with an effective amount of a composition of Compound 1A.

In some aspects, the present disclosure features a method of managing inflammation in a subject, comprising administering to the subject a pharmaceutically effective amount of a composition of Compound 1A.

In some aspects, the present disclosure features a composition of Compound 1A described herein for use in managing inflammation in a subject, (e.g., in vitro or in vivo), comprising contacting a cell with an effective amount of a composition of Compound 1A.

In some aspects, the present disclosure features a method of managing inflammation in a subject, (e.g., in vitro or in vivo), comprising contacting a cell with the composition of Compound 1A.

In some aspects, the present disclosure features a method of managing inflammation in a subject, comprising administering to the subject the composition of Compound 1A.

In some aspects, the present disclosure features a composition of Compound 1A described herein for use in managing inflammation in a subject, (e.g., in vitro or in vivo), comprising contacting a cell with the composition of Compound 1A.

In some aspects, the present disclosure features a composition of Compound 1A described herein for use in managing inflammation in a subject.

In some aspects, the present disclosure features use of a composition of Compound 1A described herein in the manufacture of a medicament for managing inflammation (e.g., in vitro or in vivo).

In some aspects, the present disclosure features use of a composition of Compound 1A described herein in the manufacture of a medicament for managing inflammation in a subject.

In some aspects, the present disclosure features use of a composition of Compound 1A described herein for managing inflammation (e.g., in vitro or in vivo).

In some aspects, the present disclosure features use of a composition of Compound 1A described herein for managing inflammation in a subject.

In some embodiments, the inflammation is inflammation resulting from traumatic brain injury or stroke. In some embodiments, the inflammation is inflammation resulting from traumatic brain injury.

In some embodiments, the inflammation is inflammation resulting from stroke.

In some embodiments, the subject is an animal. In some embodiments, the subject is a mammal. In some embodiments, the subject is a human. In some embodiments, the subject is a cell. In some embodiments, the subject is a cell population.

The disclosure having been described, the following examples are offered by way of illustration and not limitation.

EXAMPLES

Example 1. Salt Screen of Compound 1

Methods of Analysis

X-ray Powder Diffraction (XRPD). XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha 1$ $\lambda$=1.54060 Å; $\alpha 2$=1.54443 Å; $\beta$=1.39225 Å; $\alpha 1$: $\alpha 2$ ratio=0.5) running in transmission mode (step size 0.0130° 2θ, step time 18.87s) using 40 kV/40 mA generator settings. Data were visualized and images generated using the HighScore Plus 4.7 desktop application (PANalytical, 2017).

Polarised Light Microscopy (PLM). The presence of crystallinity (birefringence) was determined using an Olympus BX53 microscope, equipped with cross-polarising lenses and a Motic camera. Images were captured using Motic Images Plus 3.0. All images were recorded using the 20× objective, unless otherwise stated.

Thermogravimetric/Differential Thermal Analysis (TG/DSC). Approximately, 5-10 mg of material was added into a pre-tared open aluminum pan and loaded into a TA Instruments Discovery SDT 650 Auto-Simultaneous DSC and held at room temperature. The sample was then heated at a rate of 10° C./min from 30° C. to 300° C. during which time the change in sample weight was recorded along with the heat flow response (DSC). Nitrogen was used as the sample purge gas, at a flow rate of 200 $cm^3$/min.

Differential Scanning calorimetry (DSC). Approximately, 1-5 mg of material was weighed into an aluminum DSC pan and sealed nonhermetically with an aluminum lid. The sample pan was then loaded into a TA Instruments Discovery DSC 2500 differential scanning calorimeter equipped with a RC90 cooler. The sample and reference were heated to 200° C. or 225° C. at a scan rate of 10° C./min and the resulting heat flow response monitored. The sample was re-cooled to 20° C. and then reheated again to 205° C. all at 10° C./min. Nitrogen was used as the purge gas, at a flow rate of 50 $cm^3$/min.

Infrared Spectroscopy (IR). Infrared spectroscopy was carried out on a Bruker ALPHA P spectrometer. Sufficient material was placed onto the centre of the plate of the spectrometer and the spectra were obtained using the following parameters:

Resolution: 4 cm-1
Background Scan Time: 16 scans
Sample Scan Time: 16 scans
Data Collection: 4000 to 400 cm-1
Result Spectrum: Transmittance.
Software: OPUS version 6

Nuclear Magnetic Resonance (NMR). NMR experiments were performed on a Bruker AVIIIHD spectrometer equipped with a DCH cryoprobe operating at 500.12 MHz for protons. Experiments were performed in D20 and each sample was prepared to ca. 10 mM concentration.

Dynamic Vapour Sorption (DVS). Approximately 10-20 mg of sample was placed into a mesh vapour sorption balance pan and loaded into a DVS Advantage dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 500 minutes) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

High Performance Liquid Chromatography-Ultraviolet Detection (HPLC-UV)

Instrument: Dionex Ultimate 3000
Column: Water Acquity HSS T3 1.8 μm 150 mm×2.1 mm
Column Temperature: 40° C.
Autosampler Temperature: Ambient
UV wavelength: 243 nm
Injection Volume: 2 μL
Flow Rate: 0.5 mL/min
Mobile Phase A: 0.1% formic acid in water
Mobile Phase B: 0.1% formic acid in acetonitrile
Diluent: Water: acetonitrile 80:20 v/v
Working concentration: 0.5 mg/mL
Gradient program:

| Time (minutes) | Solvent B [%] |
|---|---|
| 0.00 | 15 |
| 12.00 | 95 |
| 15.00 | 95 |
| 15.01 | 15 |
| 22.00 | 15 |

High Performance Liquid Chromatography-Charged Aerosol Detection (HPLC-CAD)

Instrumentation: Dionex Ultimate 3000 with Dionex Corona Ultra CAD.
Column: Phenomenex Aeris Peptide XB-C18 100 Å, 150×4.6 mm, 3.6 μm (as guard column) and Dionex Acclaim Trinity P2, 50×2.1 mm, 3 μm
Mobile Phase A: Water.
Mobile Phase B: 100 mM ammonium formate pH 3.65
Flow Rate: 0.45 mL/min
Runtime: 23 min
Column Temperature: 30° C.
Injection Volume: 4 μL
Detection: CAD
Nebuliser Temperature: 30° C.
Filter: Corona
Gradient program:

| Time (minutes) | Solvent B [%] |
|---|---|
| 0.00 | 20 |
| 1.7 | 20 |
| 7.0 | 95 |
| 11.7 | 95 |
| 12.3 | 20 |
| 23.0 | 20 |

Results

NMR analysis of Compound 1 bis sodium salt, a primary salt screen using ion exchange resins and 19 basic counterions and a secondary screen were performed (Table 6). 11 of the 19 counterions were investigated by resin ion exchange.

TABLE 6

Counterions selected for salt screening

| Counterions | Mass/volume (g/mL) | Stock Solvent | Volume Added (mL) |
|---|---|---|---|
| Potassium hydroxide | 6.58568 | Water | 100 |
| Zinc chloride | 13.90816 | Water | 100 |
| L-Lysine | 14.91735 | Water | 100 |
| Bis(2-hydroxyethyl)-amine (Diethanolamine) | 9.632 | Water | 90.368 |
| N-Methyl glucamine | 19.521 | Water | 100 |
| Tromethamine (TRIS) | 12.126 | Water | 100 |
| Calcium chloride | 11.806 | Water | 100 |
| Magnesium chloride | 20.53535 | Water | 100 |
| L-Arginine | 17.77551 | Water | 100 |
| Choline hydroxide | 24.5512 | Water | 75.4488 |
| Ammonium hydroxide | 13.5695 | Water | 86.4305 |
| Diethylamine | 10.3971 | Water | 89.6029 |
| Benzathine (Dibenzylethylenediamine) | 24.291 | Ethanol:water 95:5 v/v | 75.709 |
| Ethanolamine | 6.1587 | Water | 93.8413 |
| N-(hydroxyethyl)pyrrolidine | 12.3706 | Water | 87.6294 |
| 2-Dimethylaminoethanol | 10.1115 | Water | 89.8885 |
| Morpholine | 8.83534 | Water | 91.16466 |
| N-ethyl-D-glucamine | 21.35102 | Water | 100 |
| 2-(diethylamino)ethanol | 13.3234 | Water | 86.6766 |

TABLE 7

Solvents selected for salt screening

| Solvent | ICH Class |
|---|---|
| Ethanol | 3 |
| THF | 2 |
| Isopropyl Acetate | 3 |
| MEK | 3 |
| Acetonitrile | 2 |
| IPA:Water 95:5 v/v | 3 |

Salt formation was investigated via ion exchange resin as follows. Ca. 4 g of BIO-RAD AG 50W-X8 Cation Exchange Resin was weighed into an empty solid phase extraction tube. The resin was washed with 15 mL of deionized water, followed by 30 mL of 1 M counterion solution followed by a further 15 mL of deionized water. The pH of the resin rinse was then measured and a further 30 mL of deionized water was added and the pH re-measured. This procedure was continued until the rinse was pH neutral. Approximately 120 mg of Compound 1 was dissolved in 1 mL of deionized water and passed through the resin into a tared vial. The material was washed off the resin with 15 mL of deionized water into the tared vial. The solutions were then frozen and lyophilized. 1H NMR and CAD analysis were carried out as appropriate to confirm salt formation.

Salt crystallization screening was carried out as follows. Ca. 16 mg of Compound 1 ion exchanged material from the counterions shown in was slurried in 400 to 700 μL of solvent as shown in Table 7. The experiments were temperature cycled between ambient and 40° C. in 4 hour cycles for ca. 72 h. Further material was added to N-methyl glucamine IPA:water 95:5 v/v due to dissolution. The solids were then isolated via centrifuge filter and analyzed by XRPD. Selected salts were dried at 40° C. for ca. two days and re-analyzed by XRPD. The salts were also characterized by TG/DSC and $^{1}$H NMR. Potential salts were also stored at 40° C./75% RH for ca. 24 h then re-analyzed by XRPD.

pH 7.4 solubility was carried out for Form I prior to progression to the secondary screen. Ca. 6 mg of the salt was weighed into a 2 mL vial and 50 μL aliquots of pH 7.4 PBS was added until dissolution was obtained. Form I and Form V were scaled-up for the secondary screen. The preparations were analyzed by XRPD, PLM, TG/DSC, DSC, DVS, FTIR, 1H and 31P NMR and HPLC purity. One week stability testing was carried out, salt disproportionation and hydration studies and thermodynamic solubility.

Ion exchange experiments were carried out as follows. Ca. 10 g of BIO-RAD AG 50W-X8 Cation Exchange Resin was weighed into an empty solid phase extraction tube. The resin was washed with 40 mL of deionized water, followed by 80 mL of 1 M counterion solution followed by a further 80 mL of deionized water. The pH of the resin rinse was then measured and a further 25 mL of deionized water was added and the pH re-measured. This procedure was continued until the rinse was pH neutral. Approximately 500 mg of Compound 1 was dissolved in 3 mL of deionized water and passed through the resin into a tared vial. The material was washed off the resin with 40 mL of deionized water into the tared vial. The solutions were then frozen and lyophilized. 1H NMR analysis was carried out to confirm salt formation.

Secondary screen crystallization was carried out as follows. The Compound 1 ion exchanged tromethamine material was slurried in 15 mL of ethanol. The Compound 1 ion exchanged Form V material was slurried in 15 mL of isopropyl acetate. The experiments were temperature cycled between ambient and 40° C. in 4 hour cycles for ca. 20 h. Ca. 0.5 mL of the slurries were isolated by centrifuge filtration after ca. 20 h and analyzed by XRPD. The solids were then isolated by glass sinter filtration with Grade 1 filter paper and dried under vacuum on the filter paper for ca. 1.25 h. XRPD analysis was then carried out on the dried solids.

One week stability testing was carried out for the Form I and Form V at 40° C./75% RH and ambient light and temperature in open vials and 80° C. in an open 2 mL vials within a closed 20 mL vial. After one week the solids were analyzed by XRPD for physical stability and HPLC for purity.

Salt disproportionation and hydration studies were carried out as follows: Ca. 30 mg of each salt was suspended in 400 μL of the solvent systems shown in and shaken at ambient for ca. 24 h. Thermodynamic solubility studies were carried out as follows: Ca. 30 mg of each salt was suspended in 400 μL of the solvent systems shown in and shaken at ambient for ca. 24 h.

The primary salt screen identified salts from nine of the 11 counterions investigated. Ion exchange was successful for potassium, N-methyl glucamine, tromethamine, diethanolamine, L-Lysine, L-Arginine, choline, ammonia ethanolamine, N-(hydroxyethyl) pyrrolidine and N-ethyl glucamine. One salt Pattern was identified from the majority of the salts. One crystal form was observed for N-methyl glucamine, tromethamine, L-lysine, L-arginine, ethanolamine and ammonia salts. Five salt forms were identified for potassium, with two patterns as mixtures with the first pattern. Two crystal forms were observed for bis-N-(hydroxyethyl) pyrrolidine. Two crystal forms were also observed for N-ethyl glucamine with the second pattern observed as a mixture with the first pattern. The results from the primary salt screen are shown in Table 8.

TABLE 8

Primary Salt Screen Results

| | Solvent | | | | | |
|---|---|---|---|---|---|---|
| Counterion | Ethanol | THF | Isopropyl Acetate | MEK | Acetonitrile | IPA:Water 95:5 v/v |
| N-methyl glucamine | 1 (PS) | 1 (PS) | 1 (PS) | 1 (PS) | 1 (PS) | 1 (PS) |
| Tromethamine | 1 (PS) | 1 (PS) | 1 (PS) | 1 (PS) | 1 (PS) | 1 (PS) |
| Diethanolamine | # | # 1 (PS) | ^ 1 (PS) | ^ # | % | # 2 (PS) |
| Potassium | 1 (PS) 3 (PS) | 1 (PS) | 1 (PS) | 1 (PS) | 1 (PS) | 1 (PS) 2 (PS) |
| L-lysine | AM | AM | 1 PC (PS) | 1 PC (PS) | % | AM |
| L-arginine | 1 (PS) | 1 (PS) | 1 (PS) | 1 (PS) | 1 (PS) | 1 (PS) |
| Ethanolamine | GG | 1 (PS) | 1 (PS) | AM | 1 (PS) | 1* (PS) |
| N-(hydroxyethyl) pyrrolidine | GG | 1 (PS) | 2 (PS) | 1 (PS) | 1* (PS) | GG |
| Ammonia | 1 (PS) | 1 (PS) | 1 (PS) | 1 (PS) | AM | 1 (PS) |
| Choline | GG | GG | GG | GG | GG | GG |
| N-ethyl glucamine | 1 (PS) | % | 1 (PS) | 1 (PS) | 1 (PS) | AM |

Figure 6:
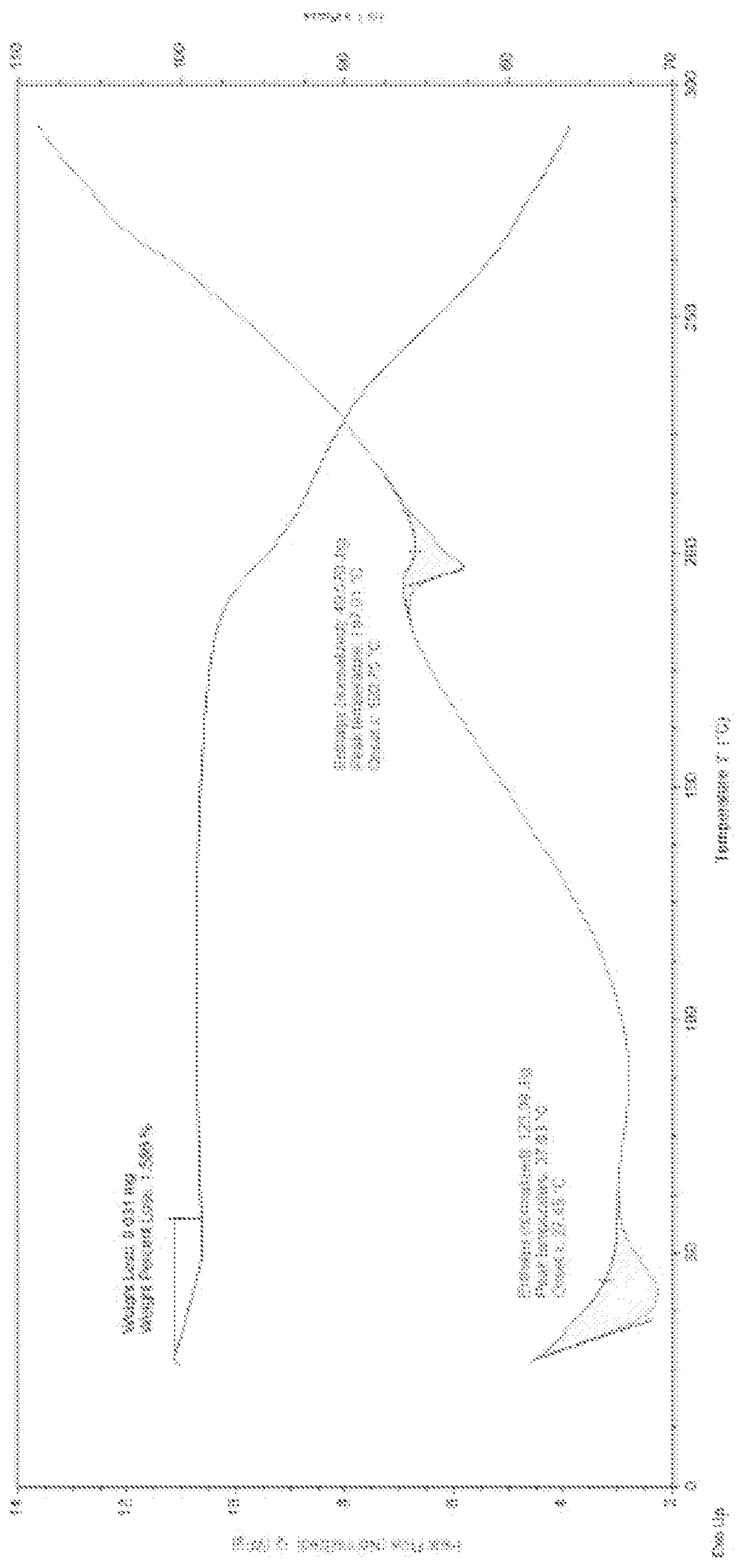
FIG. 6 depicts TG/DSC thermogram of Form I from ethanol.

PS Potential salt
Numbers Salt Pattern
PC Poorly crystalline
* Limited material
AM Amorphous
% Predominantly amorphous
GG Gum/ glass-like
^ Pattern 1 Free Acid
Pattern 2 Free Acid Tris Salt Thermal analysis of Form I from ethanol (FIG. 6) showed a loss of 1.6% up to ca. 60° C. with the onset of degradation ca. 190° C. The weight loss corresponded with 0.6 equivalents of water or 0.3 equivalents of ethanol. Two broad endothermic events were observed with onset of ca. 27° C. (peak at 38° C.) and 193° C. (peak at 197° C.).

Form I was found to be hydrated with 0.5% uptake between 40% RH and 90% RH. Total uptake at 90% RH was corresponded with 1.2 equivalents of water. One week stability testing showed ≤0.2% Area decrease in purity under the conditions tested and Pattern 1 remained unchanged. Solubility was found to be ≤45 mg/mL at pH 8 and 8.5 and 29 mg/mL at pH 7.4. Hydration experiments showed Form I to remain. Solubility in water was too high for solids to be recovered to assess disproportionation.

Potassium

Figure 7:
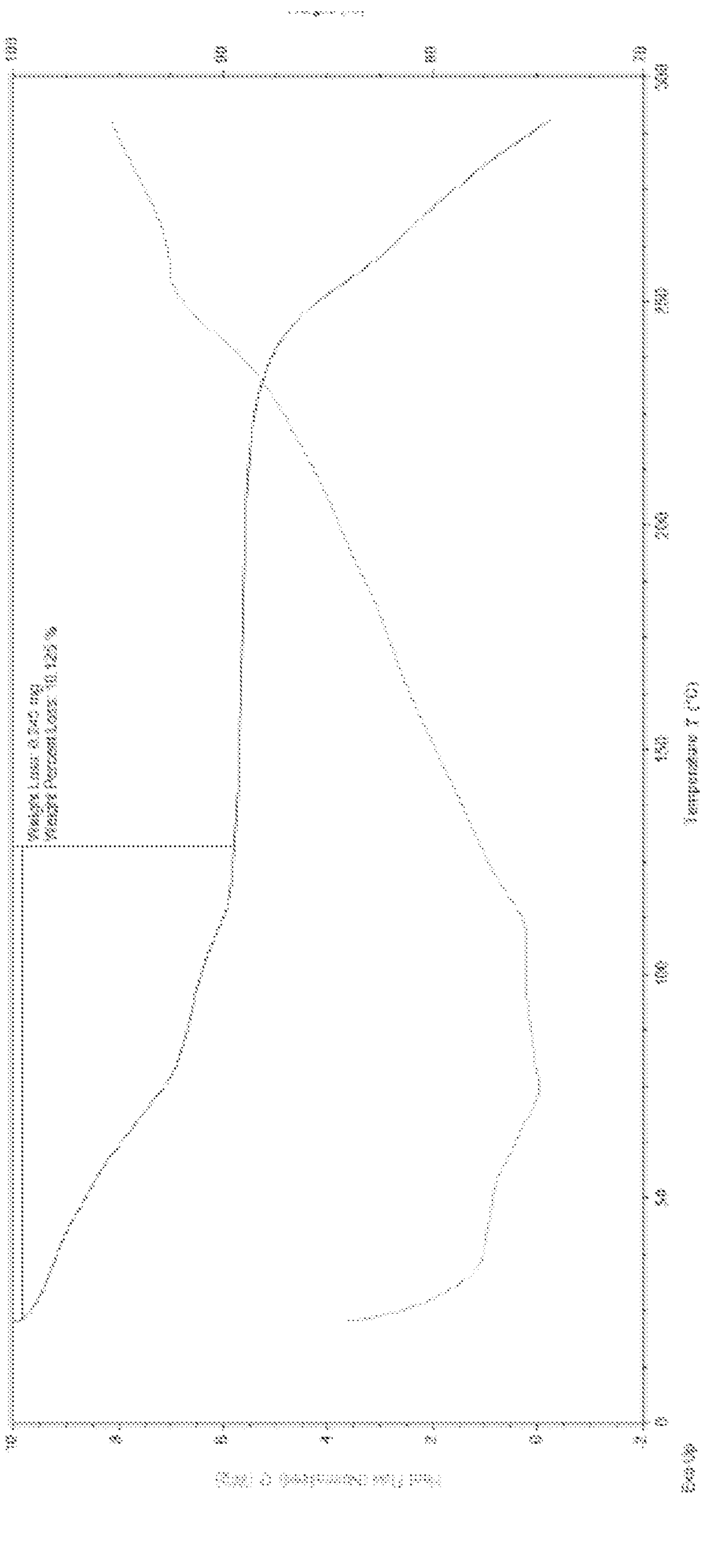
FIG. 7 depicts TG/DSC thermogram of potassium Pattern 1 from isopropyl acetate.
Figure 8:
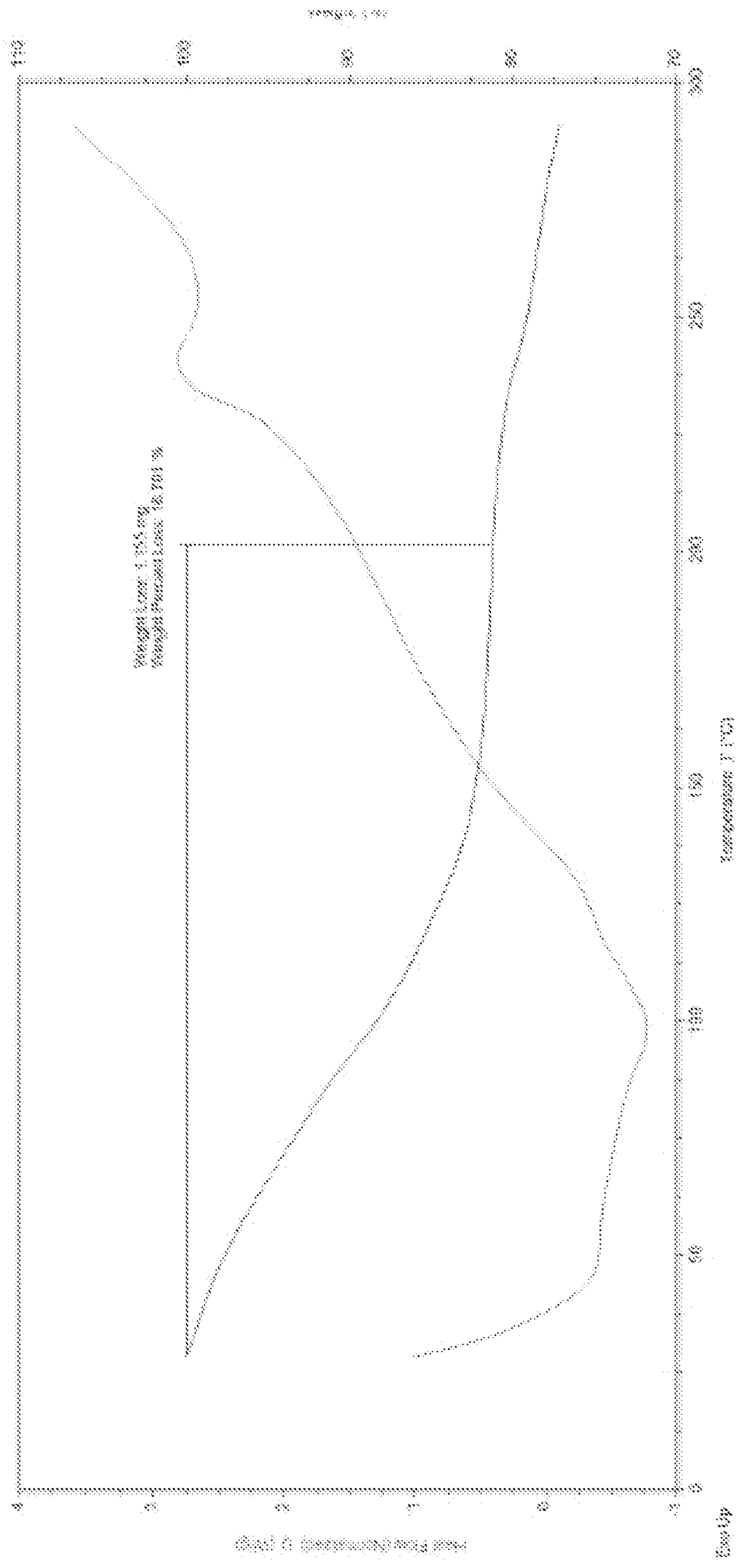
FIG. 8 depicts TG/DSC thermogram of potassium Pattern 5 from storage of Pattern 1 at 40° C./75% RH.

Thermal analysis of Pattern 1 from isopropyl acetate (FIG. 7) showed a loss of 10.1% up to ca. 125° C. with the onset of degradation ca. 210° C. The weight loss observed corresponded to 3.5 equivalents of water. No defined thermal events were observed. Thermal analysis of Pattern 5 from storage at 40° C./75% RH of Pattern 1 (FIG. 8) showed a loss of 18.7% up to ca. 200° C. The weight loss observed corresponded with 6.5 equivalents of water. No defined thermal events were observed.

Form V

Figure 9:
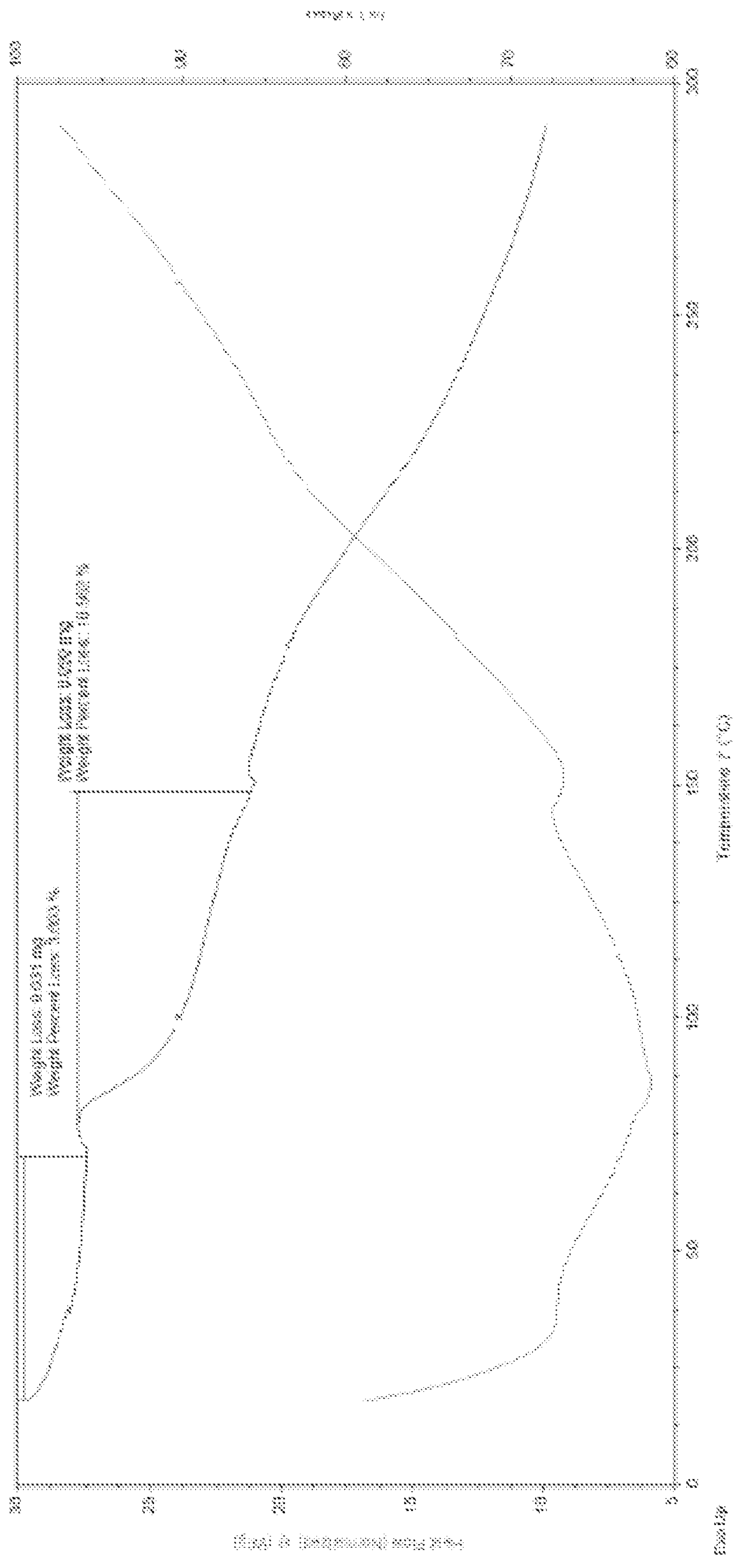
FIG. 9 depicts TG/DSC thermogram of Form V from isopropyl acetate.

Thermal analysis of Form V from isopropyl acetate (FIG. 9) showed a loss of 3.6% up to ca. 75° C. followed by a loss of 10.6%. The initial weight loss corresponded with 0.2 equivalents of isopropyl acetate. DSC analysis showed no defined thermal events.

Form V was found to be hygroscopic with 19.0% uptake at 90% RH. One week stability testing showed no loss in purity at ambient and 40° C./75% RH but 0.9% Area decrease in purity at 80° C. Form V remained after stability testing but with some minor changes at 80° C. Solubility was found to be >45 mg/mL at pH 7.4 and >39 mg/mL at pH 8 and 8.5. Solutions were obtained from disproportionation and hydration study experiments due to high solubility.

TABLE 9

Summary of Primary Salt Screen

| Counterion | Solvent | Pattern | Polymorphism observed for counterion | TG/DSC | Remained pattern after 40 °C | Remained pattern after 40 °C/75% RH | NMR |
|---|---|---|---|---|---|---|---|
| N-methyl glucamime | All 6 | 1 | No | N/A | Yes | No | N/A |
| Tromethamine | All 6 | 1 | No | 1.6% loss. Endothermic event onsets 27 °C & 193 °C | Yes | Yes | 0.3 equivalents of ethanol |
| Potassium | THF, isopropyl acetate, MEK & acetonitrile | 1 | Yes | 10.1% loss. No defined thermal events. | Yes | No - Pattern 5 (6.5 eq. water) | Trace of isopropyl acetate hydrated) |
| L-lysine | Isopropyl acetate & MEK | 1, poorly crystalline | No | N/A | Not carried out poorly crystalline material | Not carried out poorly crystalline material | N/A |
| L-arginine | All 6 | 1, poorly crystalline | No | N/A | Predominantly unchanged, poorly crystalline | Predominantly unchanged, poorly crystalline | N/A |
| Ethanolamine | THF, isopropyl acetate, aceto-nitrile & IPA: water 95:5 v/v | 1 | No | N/A | Yes | Loss in crystallinity | N/A |
| N-(hydroxyethyl) pyrrolidine | THF, MEK & acetonitrile | 1 | Yes | N/A | Yes | No, Pattern 2 | N/A |
| N-(hydroxyethyl) pyrrolidine | Isopropyl acetate | 2 | Yes | N/A | Yes | Yes | N/A |
| Amonia | Ethanol, THF, isopropyl acetate, MEK & IPA:water 95:5 v/v | 1 | No | N/A | Predominantly unchanged | Predominantly unchanged | N/A |
| N-ethyl glucamine | Ethanol, isopropyl acetate, MEK & acetonitrile | 1 | Yes | N/A | Yes | No. Mixture Pattern 1 & 2 | |

Form I (Pattern 1 of the Tromethamine Salt)

Figure 10:
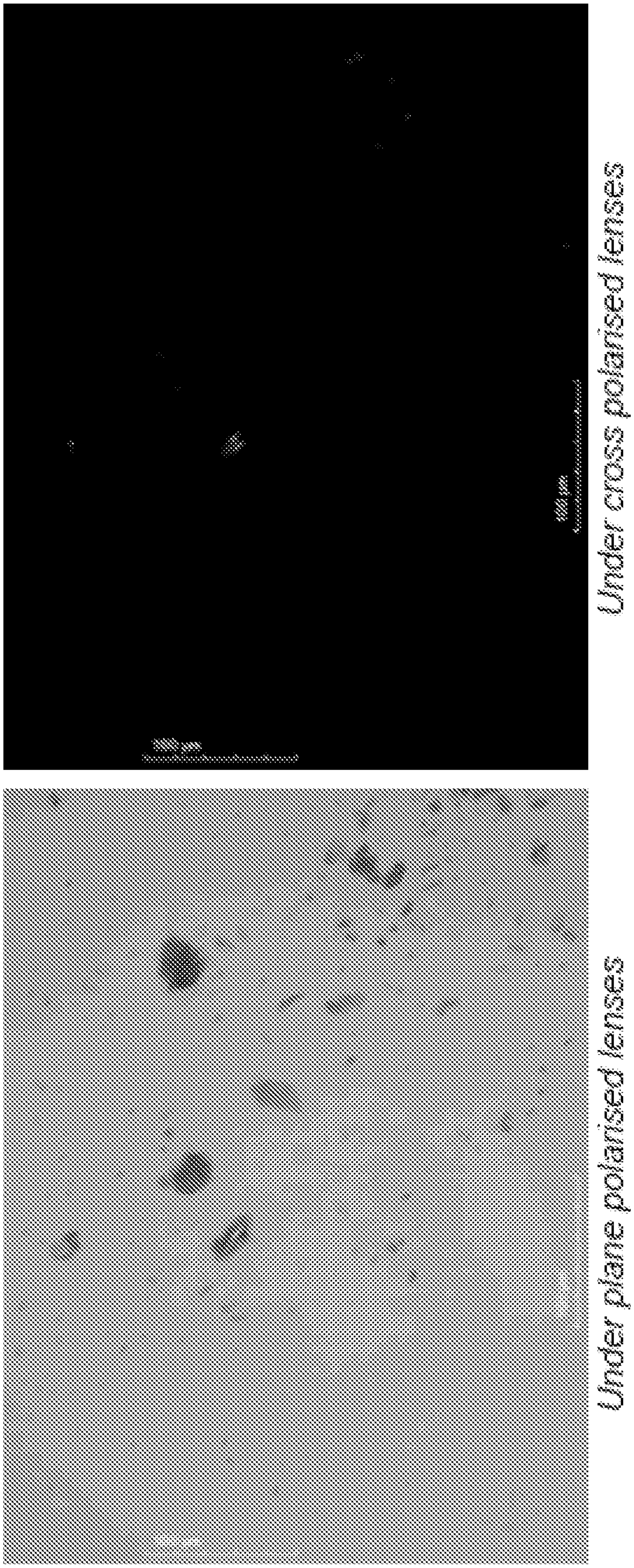
FIG. 10 depicts PLM images of Form I.
Figure 11:
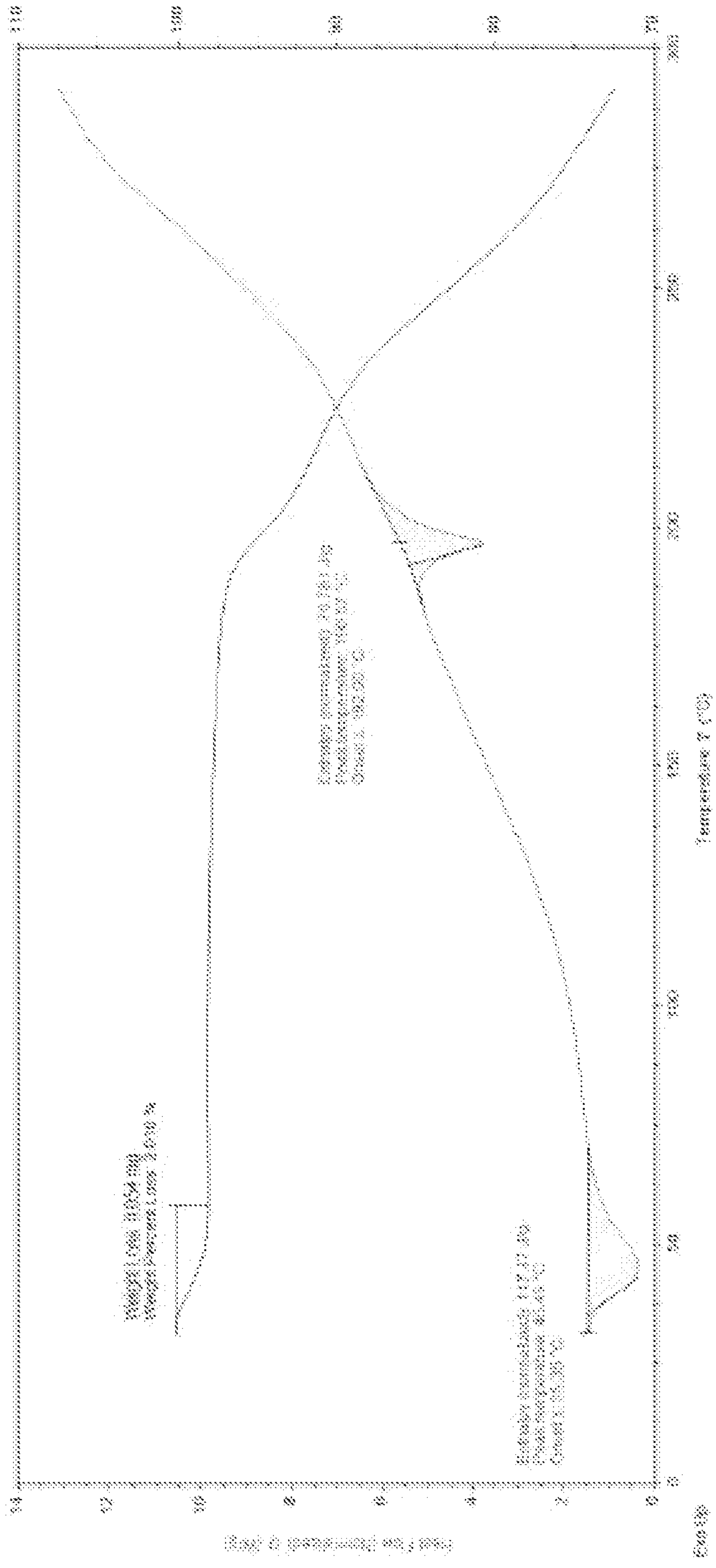
FIG. 11 depicts TG/DSC thermogram of Form I.
Figure 12:
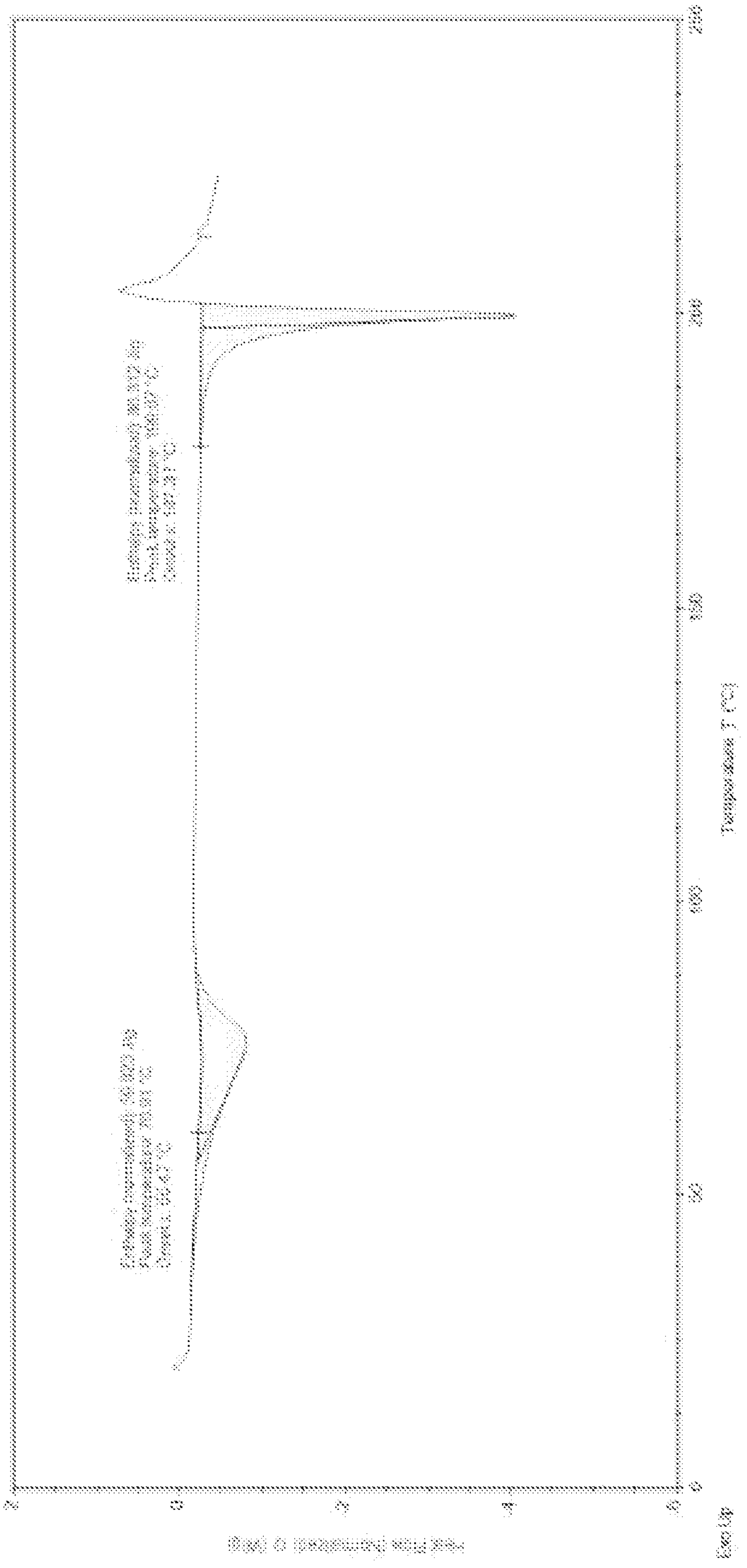
FIG. 12 depicts DSC thermogram of Form I.
Figure 13A:
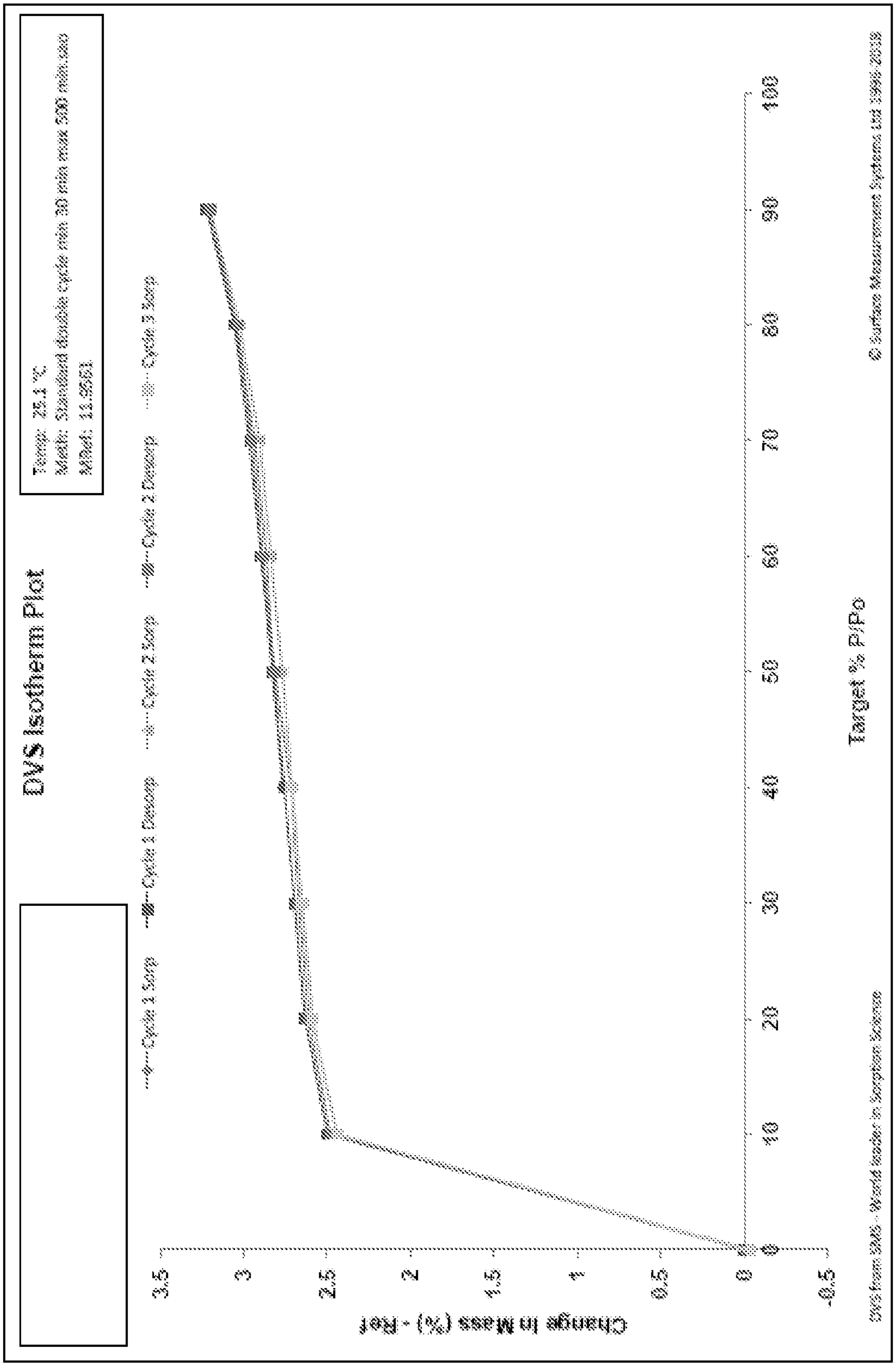
FIG. 13A depicts the DVS isotherm of Form I and FIG. 13B depicts the DVS kinetic plot of Form V.
Figure 13B:
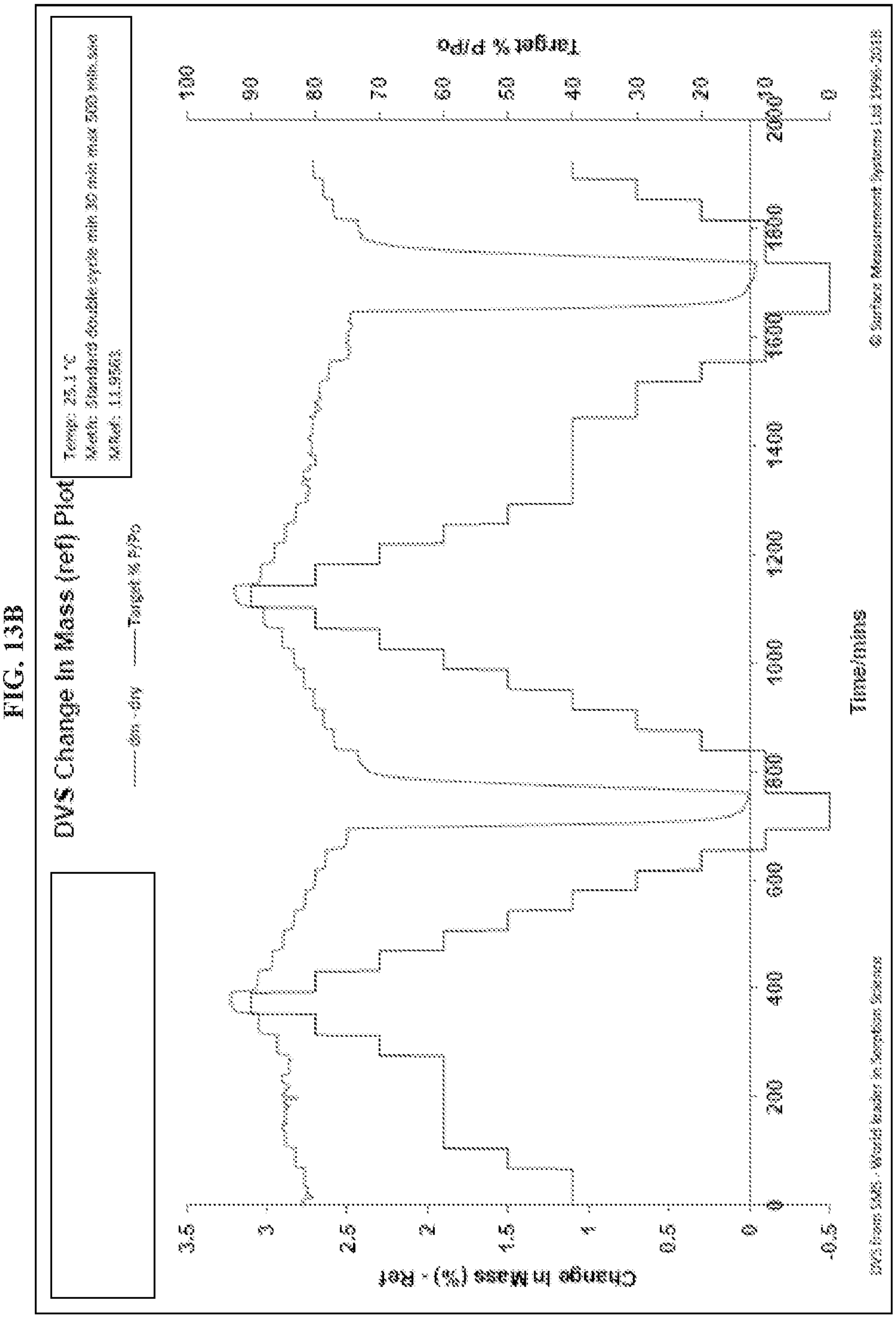
Figure 14:
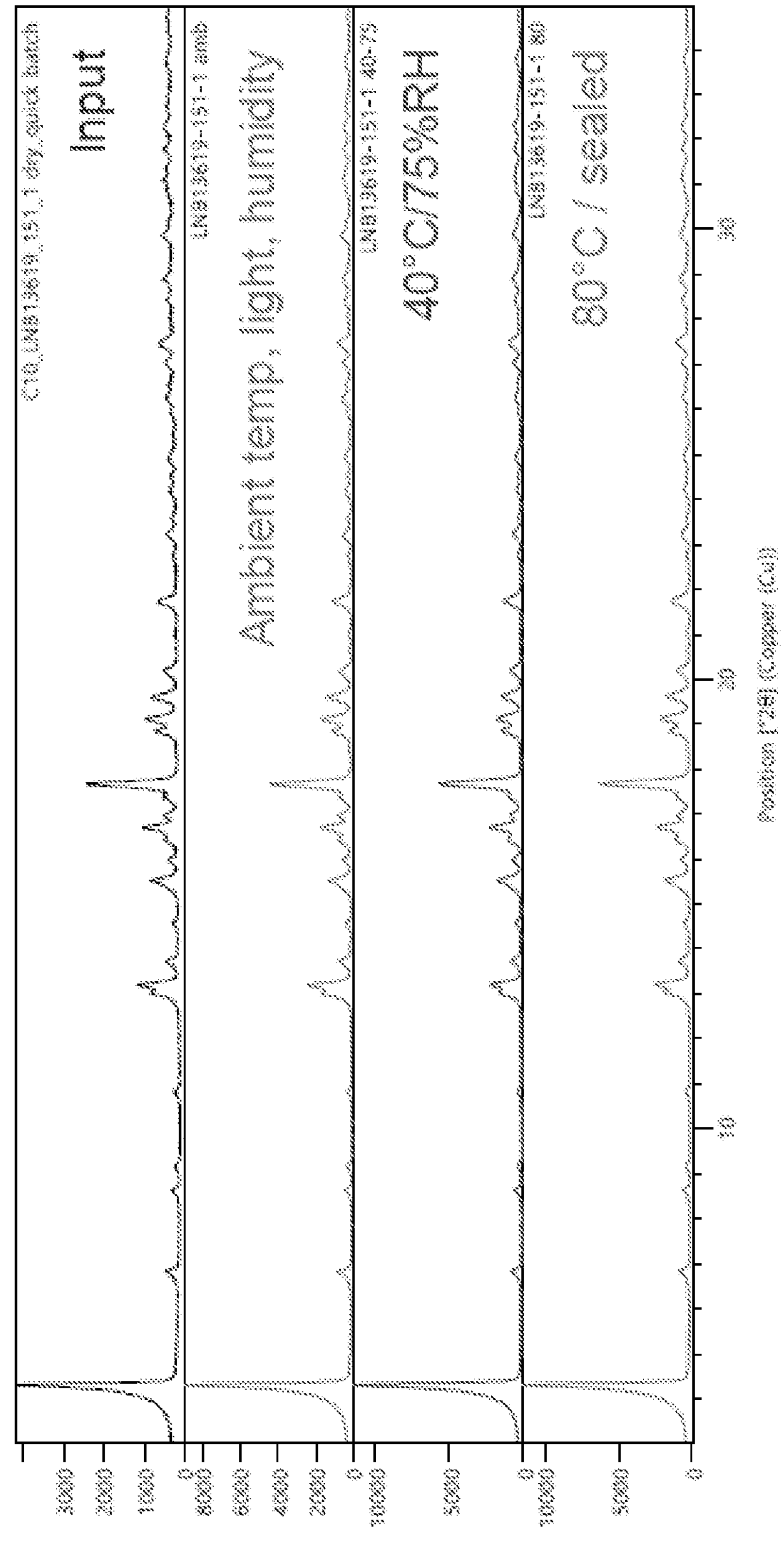
FIG. 14 depicts the one week stability XRPD diffractograms of Form I.

Form I was scaled-up, confirmed with XRPD analysis. PLM analysis (FIG. 10) showed a rod-like morphology with slight birefringence. TG analysis (FIG. 11) showed a loss of 2.0% from the outset up to ca. 60° C. This weight loss corresponded with 0.4 equivalents of ethanol. DSC analysis showed two endothermic events with onset ca. 35° C. (peak at 45° C.) and 192° C. (peak at 197° C.). The thermal analysis was found to be consistent with the primary screen data. DSC analysis (FIG. 12) showed two endothermic events with onset ca. 55° C. (peak at 77° C.) and 197° C. (peak at 200° C.). DVS analysis (FIGS. 13A and 13B) showed Form I to be hydrated. Between 40% RH and 90% RH 0.5% uptake was observed. The total uptake at 90% RH (3.2%) corresponded with 1.2 equivalents of water. Between 10% RH and 0% RH 2.5% loss was observed. Post DVS XRPD analysis showed Form I to remain unchanged. FT-IR analysis showed some differences compared with amorphous Compound 1. $^{1}$H NMR analysis showed 2.1 equivalents of tromethamine and reprocess for ethanol. HPLC analysis indicated 99.7% Area purity. The one week stability results are shown in Table 10. ≤0.2% Area decrease in purity was observed for the tromethamine salt. Form I was observed to remain under all conditions (FIG. 14). Hydration studies showed Form I to remain under all 3 water activities tested. Insufficient solids remained from the disproportionation water experiment. Thermodynamic solubility studies (Table 11) showed solubility >45 mg/mL for pH 8 and 8.5 and 29 mg/mL for pH 7.4.

TABLE 10

One week stability results for Form I

| Condition | XRPD Analysis | Input Purity (% Area) | HPLC Purity (% Area) |
|---|---|---|---|
| 40° C./75% RH | Salt Pattern 1 | 99.7 | 99.9 |
| 80° C. | Salt Pattern 1 | | 99.5 |
| Ambient | Salt Pattern 1 | | 99.9 |

TABLE 11 pH solubility results for Form I

| Buffer | Solubility (mg/mL) | XRPD Analysis |
|---|---|---|
| pH 7.4 PBS | 29.4 | P2TS |
| pH 8.0 borate buffer | >51.4 | S |
| pH 8.5 borate buffer | >45.0 | S |

Key
P2TS Potential Pattern 2 Tromethamine salt
S Solution

Form V (Bis-N-(Hydroxyethyl) Pyrrolidine Pattern 2)

Figure 15:
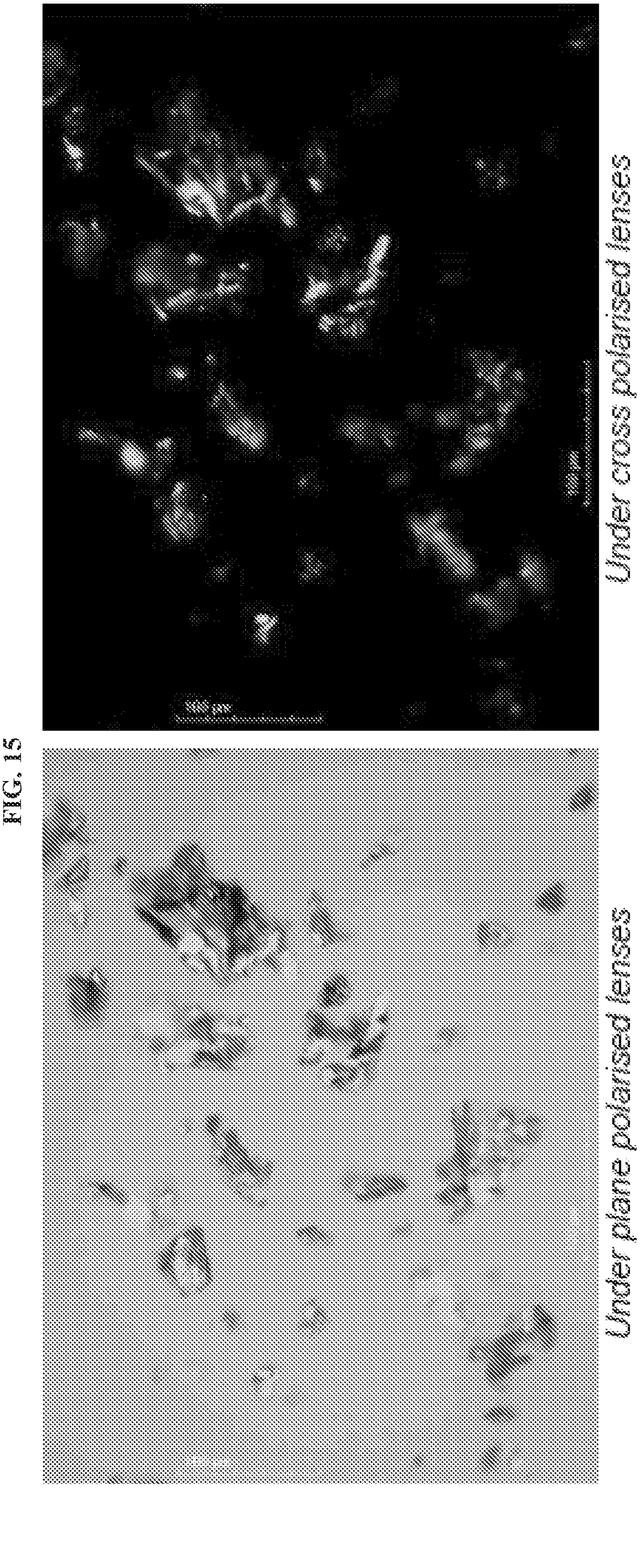
FIG. 15 depicts the PLM images of Form V.
Figure 16:
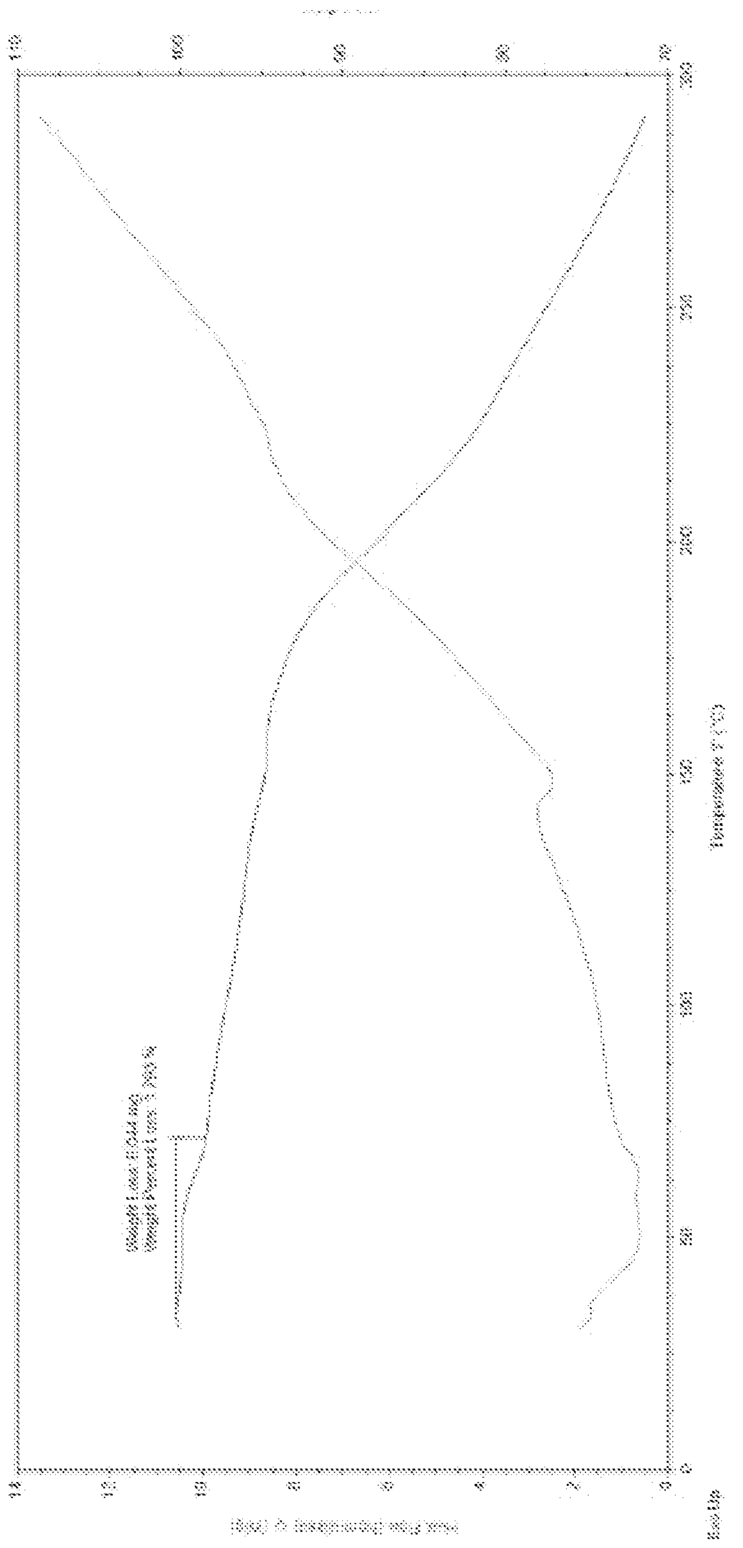
FIG. 16 depicts the TG/DSC thermogram of Form V.
Figure 17:
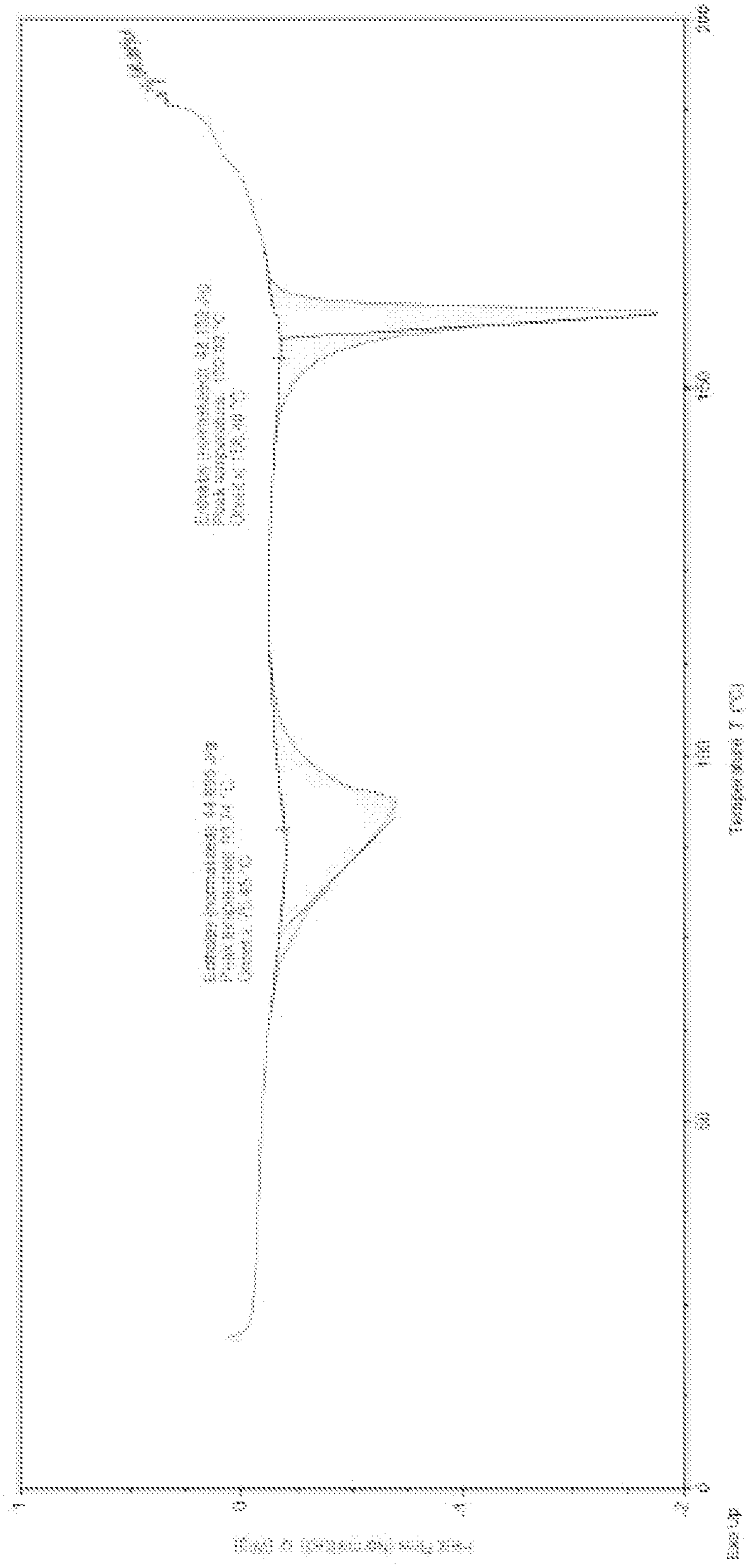
FIG. 17 depicts the DSC thermogram of Form V.
Figure 18A:
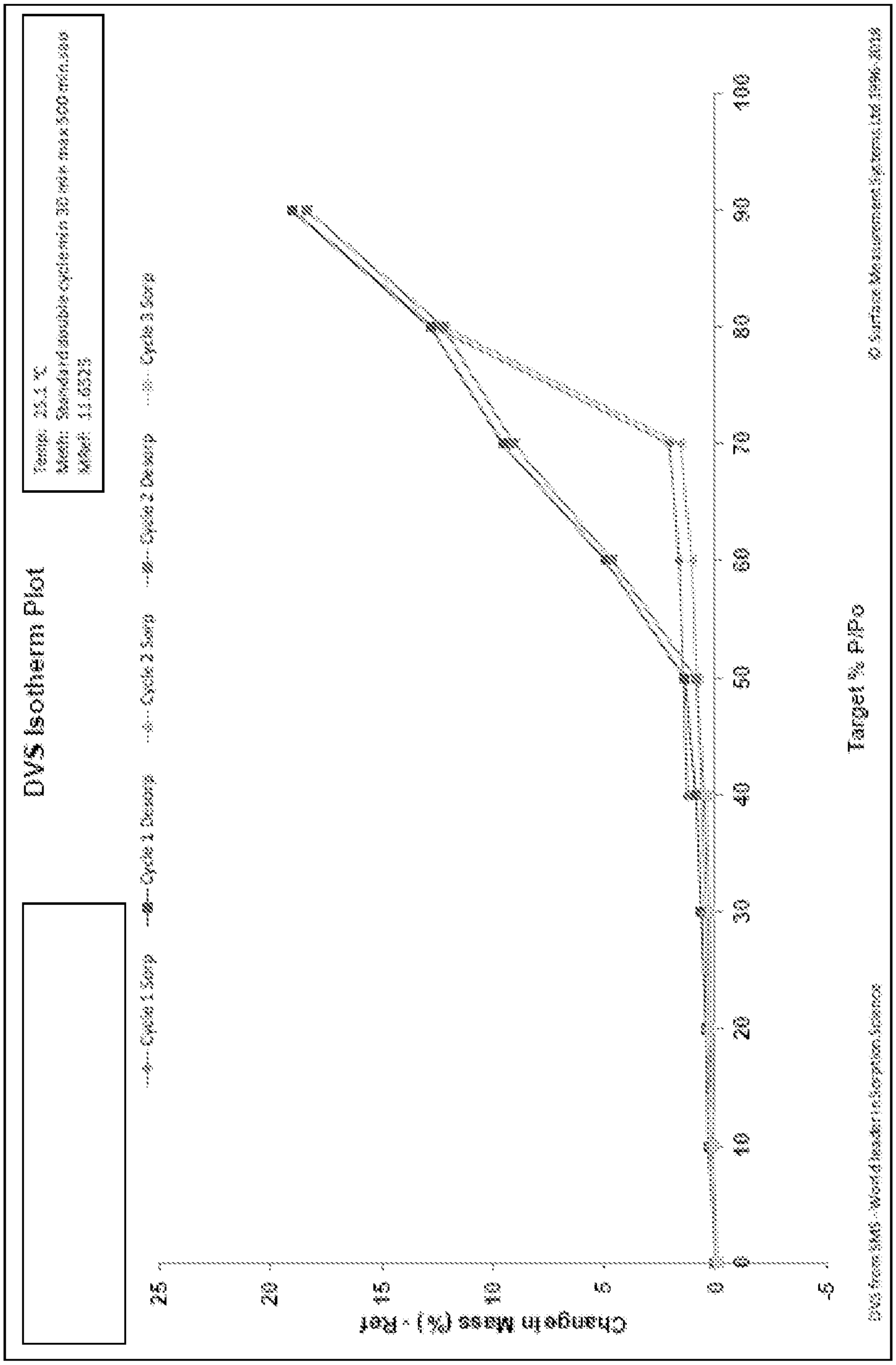
FIG. 18A depicts the DVS isotherm of Form V and FIG. 18B depicts the DVS kinetic plot of Form V.
Figure 18B:
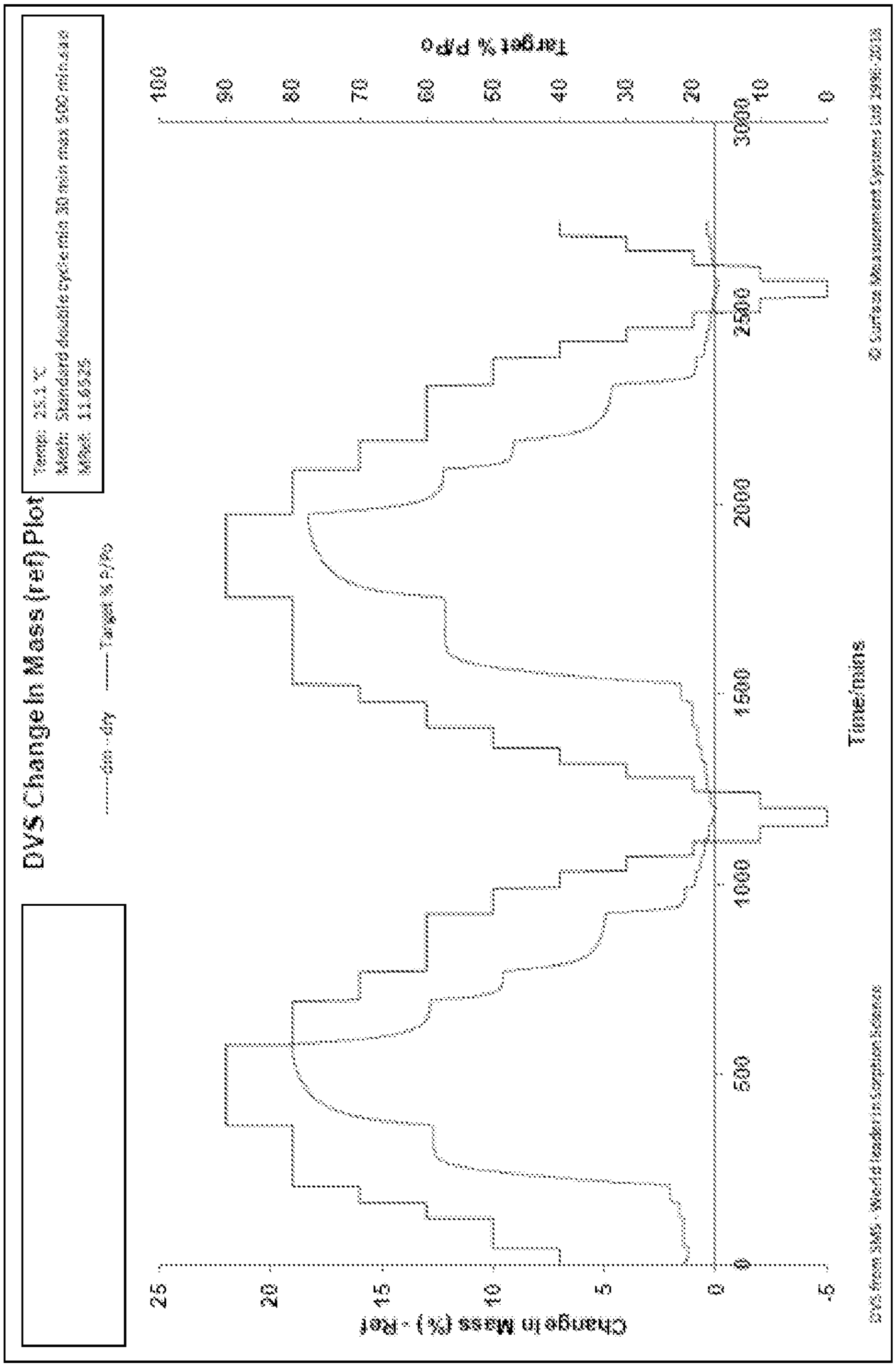
Figure 19:
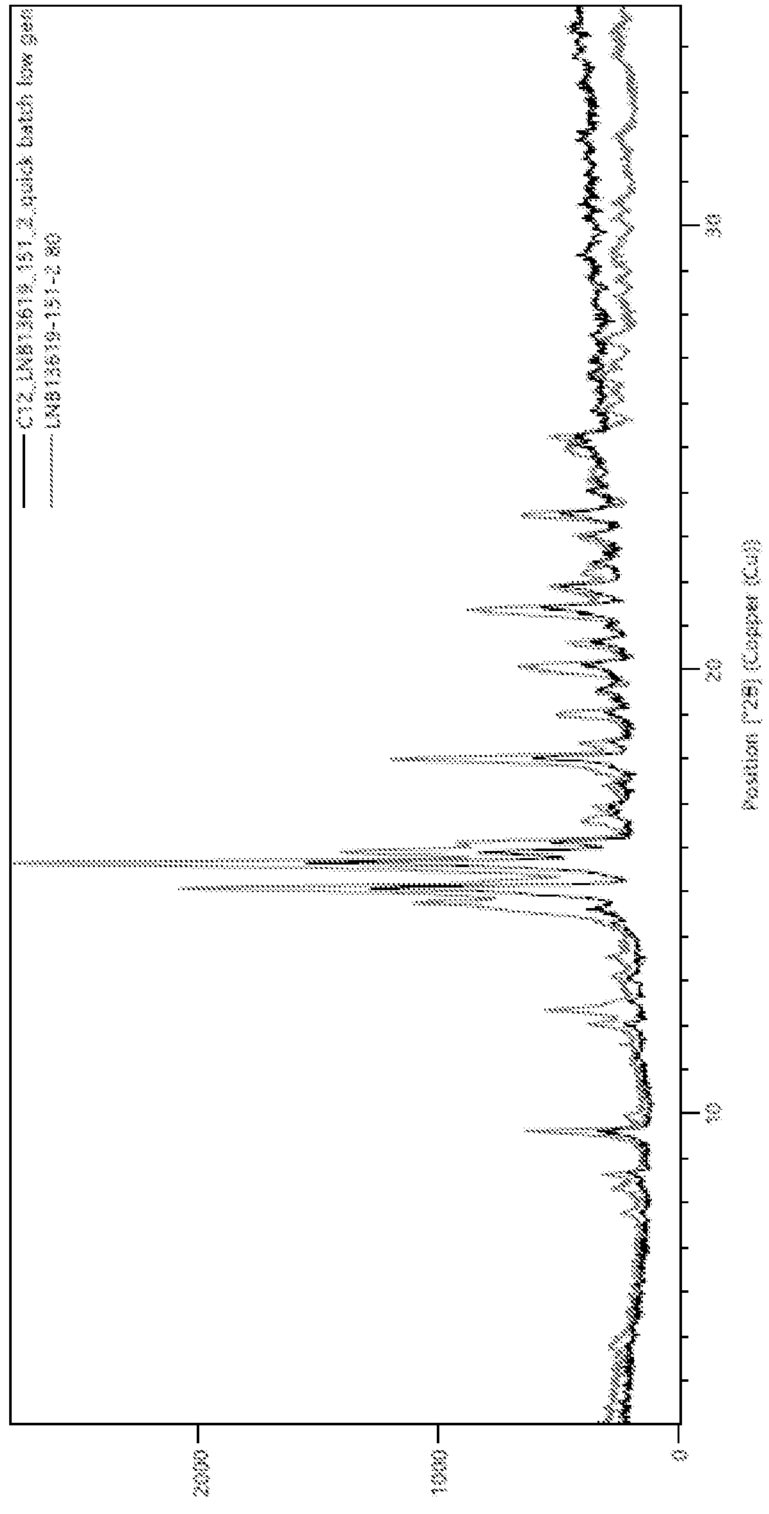
FIG. 19 depicts one week stability XRPD diffractograms of Form I and overlay of 80° C. and input N-(hydroxyethyl) pyrrolidine salt.

Form V salt was scaled-up. PLM analysis (FIG. 15) showed birefringent particles with no clearly defined morphology. TG analysis (FIG. 16) showed a weight loss of 1.8% up to ca. 65° C. This weight loss corresponded with 0.7 eq. water. DSC analysis showed no defined thermal events. DSC analysis (FIG. 17) showed two endothermic events with onset ca. 75° C. (peak at 94° C.) and 156° C. (peak at 160° C.). DVS analysis (FIGS. 18A and 18B) showed Form V to be hygroscopic with 17.8% uptake between 40% RH and 90% RH. The total uptake observed at 90% RH was 19.0%, this corresponded with 7.3 equivalents of water. Post DVS XRPD analysis showed Form V to remain unchanged. FT-IR analysis showed some differences compared with amorphous Compound 1. $^{1}$H NMR analysis showed 1.0 equivalents of N-(hydroxyethyl) pyrrolidine. HPLC analysis indicated 99.6% Area purity. The one week stability results are shown in (Table 12a). No loss in purity was observed apart from 0.9% Area decrease for 80° C. Pattern 2 was observed to remain unchanged apart from some minor changes were noted at 80° C. (FIG. 19). Hydration studies and disproportionation experiments showed no solids after 24 h. Thermodynamic solubility studies (Table 12b) showed solubility >39 mg/mL for pH 8.0 and 8.5 and >45 mg/mL for pH 7.4.

TABLE 12a

One week stability results for Form V

| Condition | XRPD Analysis | Input Purity (% Area) | HPLC Purity (% Area) |
|---|---|---|---|
| 40° C./75% RH | Salt Pattern 2 | 99.6 | 99.6 |
| 80° C. | Salt Pattern 2 with some minor changed | | 98.7 |
| Ambient | Salt Pattern 2 | | 99.8 |

TABLE 12b pH solubility results for Form V

| Buffer | Solubility (mg/mL) | XRPD Analysis |
|---|---|---|
| pH 7.4 PBS | >45.3 | S |
| pH 8.0 borate buffer | >39.1 | S |
| pH 8.5 borate buffer | >39.9 | S |

Key
S Solution

SUMMARY

The primary salt screen located salts from nine of the 11 counterions investigated. 19 counterions were investigated for resin ion exchange, 11 of these showed ion exchanged to be successful. One salt Pattern was identified from the majority of the salts. One crystal form was observed for N-methyl glucamine, tromethamine, L-lysine, L-arginine, ethanolamine and ammonia. Five salt forms were identified for potassium. Two crystal forms were observed for N-(hydroxyethyl) pyrrolidine. Two crystal forms were also observed for bis-N-ethyl glucamine. Form I (Tromethamine Pattern 1) and Form V (N-(hydroxyethyl) pyrrolidine Pattern 2) were scaled-up. The properties of these salt forms are summarized in Table 13. The tromethamine salt showed one week stability and solubility ≤45 mg/mL at pH 8 and 8.5 and 29 mg/mL at pH 7:4. The tromethamine salt was observed to be hydrated in comparison with the bis-N-(hydroxyethyl) pyrrolidine salt which was found to be hygroscopic. The tromethamine salt Pattern 1 was found to have favourable properties in comparison with the sodium salt Pattern 3. An improvement in stability was observed in comparison with the sodium salt Pattern 3 which showed form conversion during one week stability testing and a large drop in purity at 80° C. Pattern 3 sodium salt was scaled-up. Higher solubility at pH 7.4 was also observed for the tromethamine salt compared with the sodium salt.

TABLE 13

| Summary of secondary screen | | | |
|---|---|---|---|
| | Tromethamine Pattern 1 | N-(hydroxyethyl)pyrrolidine Pattern 2 | Sodium Pattern 3 |
| PLM morphology | Rod-like | No clearly defined morphology | N/A |
| TGA mass loss (%) | 2.0% | 1.8% | 11 |
| DSC event onsets ( °C) | 55 & 197 | 75 & 156 | No thermal events (DTA primary screen) |
| DVS | 0.5% uptake between 40 & 90% RH. Total uptake 3.2% (1.2 eq. water) | 17.8% uptake between 40 & 90% RH. Total uptake 19.0% (7.3 eq. water) | N/A |
| Stoichiometry | Bis | Mono | Bis |
| HPLC purity (% Area) | 99.7 | 99.6 | 98.8 |
| Stability | ≤0.2% Area decrease, remained Pattern 1 | No loss in purity at ambient & 40 °C/75% RH. 0.9% Area decrease at 80 °C Remained Pattern 2, some minor changes at 80 °C | Large drop in purity at 80 °C Pattern 1 & 2 mixture at 40 °C/75% RH, Pattern 5 obtained at 80 °C, Pattern 3 & 4 mixture from ambient. |
| Solubility | ≥45 mg/mL pH 8 & 8.5, 29 mg/mL pH 7.4. Pattern 2 obtained at pH 7.4 | >45 mg/mL at pH 7.4, >39 mg/mL at pH 8 & 8.5 | <12 mg/mL at pH 7.4 |
| Disproportionation & Hydration | Remained Pattern 1, insufficient solids from water | Solutions obtained | N/A |

Example 2. Tris Salt Properties (Form I, Form II, Form III, and Form IV)

Methods of Analysis

X-ray Powder Diffraction (XRPD). XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha1$ $\lambda$=1.54060 Å; $\alpha2$=1.54443 Å; $\beta$=1.39225 Å; $\alpha1$: $\alpha2$ ratio=0.5) running in transmission mode (step size 0.0130° 2θ, step time 18.87s) using 40 kV/40 mA generator settings. Data were visualized and images generated using the HighScore Plus 4.7 desktop application (PANalytical, 2017).

Polarized Light Microscopy (PLM). The presence of crystallinity (birefringence) was determined using an Olympus BX50 microscope, equipped with cross-polarizing lenses and a Motic camera. Images were captured using Motic Images Plus 2.0. All images were recorded using the 20× objective, unless otherwise stated.

Hot Stage Light Microscopy. Thermal events were monitored visually using a calibrated Linkam THM600 hotstage with connected controller unit coupled to an Olympus BX50 polarizing microscope equipped with a Motic camera and image capture software (Motic Images Plus 2.0). Approximately 0.5 mg of material was placed onto a microscope coverslip and heated at a rate of 10° C./min with images taken at routine intervals to document any thermal transitions. All images were recorded using the 10× objective, unless otherwise stated.

Thermogravimetric Analysis/Differential Scanning calorimetry (TGA/DSC). Approximately, 5-10 mg of material was added into a pre-tared open aluminum pan and loaded into a TA Instruments Discovery SDT 650 Auto-Simultaneous DSC or simultaneous thermogravimetric/differential thermal analyzer (TG/DTA) and held at room temperature. The sample was then heated at a rate of 10° C./min from 30° C. to 400° C. during which time the change in sample weight was recorded along with the heat flow response (DSC) or any differential thermal events (DTA). Nitrogen was used as the sample purge gas, at a flow rate of 200 $cm^3$/min for TG/DSC or 300 $cm^3$/min for TG/DTA.

Differential Scanning calorimetry (DSC). Approximately, 1-5 mg of material was weighed into an aluminum DSC pan and sealed nonhermetically with an aluminum lid. The sample pan was then loaded into a TA Instruments Discovery DSC 2500 differential scanning calorimeter equipped with a RC90 cooler. The sample and reference were heated to 220° C. at a scan rate of 10° C./min and the resulting heat flow response monitored. The sample was re-cooled to 20° C. and then reheated again to 220° C. all at 10° C./min. Nitrogen was used as the purge gas, at a flow rate of 50 $cm^3$/min. Alternatively, a modulated DSC was used.

Infrared Spectroscopy (IR). Infrared spectroscopy was carried out on a Bruker ALPHA P spectrometer. Sufficient material was placed onto the centre of the plate of the spectrometer and the spectra were obtained using the following parameters:

Resolution: 4 cm-1
Background Scan Time: 16 scans
Sample Scan Time: 16 scans
Data Collection: 4000 to 400 cm-1
Result Spectrum: Transmittance
Software: OPUS version 6

Nuclear Magnetic Resonance (NMR). NMR experiments were performed on a Bruker AVIIIHD spectrometer equipped with a PRODIGY cryoprobe operating at 500.23 MHz for protons or DCH cryoprobe operating at 500.12 MHz for protons. Experiments were performed in D20 or DMSO-d6 and each sample was prepared to ca. 10 mM concentration.

Dynamic Vapour Sorption (DVS). Approximately, 10-20 mg of sample was placed into a mesh vapour sorption balance pan and loaded into a DVS Advantage dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 120 minutes) at 25° C. After completion of the sorption cycle, the sample was dried using the same procedure to 0% RH and then a second sorption cycle back to 40% RH. Additional cycles were performed at 40° C. and 60° C. On changing the instrument temperature 2 hours were allowed to equilibrate. The weight change during the sorption/desorption cycles were plotted, allowing for the hygroscopic nature of the sample to be determined. XRPD analysis was then carried out on any solid retained.

Variable temperature X-ray Powder Diffraction (VT-XRPD). VT-XRPD analysis was carried out on a Philips X'Pert Pro Multipurpose diffractometer equipped with a temperature chamber. The samples were scanned between 4 and 35.99 ° 2θ using Cu K radiation (al)=1.54060 Å; α2=1.54443 Å; β=1.39225 Å; α1: α2 ratio=0.5) running in Bragg-Brentano geometry (step size 0.008° 2θ) using 40 kV/40 mA generator settings.

Variable Humidity X-ray Powder Diffraction (VH-XRPD). VH-XRPD analysis was carried out on a Philips X'Pert Pro Multipurpose diffractometer equipped with a humidity chamber. The samples were scanned between 4 and 35.99 ° 2θ using Cu K radiation (α1 λ=1.54060 Å; α2=1.54443 Å; β=1.39225 Å; α1: α2 ratio=0.5) running in Bragg-Brentano geometry (step size 0.008° 2θ) using 40 kV/40 mA generator settings. Measurements for received Pattern 1 were performed at 40% RH, 0% RH and 40% RH. Two measurements were taken at 0% RH after ca. 10 minutes at 0% RH and after ca. 100 minutes in total at 0% RH.

High Performance Liquid Chromatography-Ultraviolet Detection (HPLC-UV)

Instrument: Dionex Ultimate 3000
Column: Agilent Zorbax Eclipse Plus C18, 150×3 mm, 3.5 μm
Column Temperature: 25° C.
Autosampler Temperature: Ambient
UV wavelength: 246 nm
Injection Volume: 5 μL
Flow Rate: 1.2 mL/min
Mobile Phase A: 50 mM ammonium acetate in water
Mobile Phase B: Acetonitrile
Diluent: Water: methanol 70:30 v/v
Working Concentration: 0.4 mg/mL
J Gradient Program:

| Time (minutes) | Solvent B [%] |
|---|---|
| 0.0 | 15 |
| 2.0 | 30 |
| 10.0 | 50 |
| 15.5 | 85 |
| 19.0 | 85 |
| 19.1 | 15 |
| 25.0 | 15 |

Solvent Solubility Screen

An amorphous batch of Compound 1 bis-tris salt was prepared by fast rotary evaporation (e.g. from a methanolic solution) or freeze drying of an API solution (solubility depending). An organic and aqueous solvent solubility screen was carried out using 32 solvent systems.

The solubility screen was carried out as follows. To ca. 10 mg of the lyophilized material, the appropriate solvent system was added in aliquots of 50 μL and if solid remained, the vial was gently heated to ca. 40° C. to aid dissolution. The solvent systems used in the solubility assessment can be found in Table 14. Solvent addition was continued until the material had fully dissolved or 1 mL of the appropriate solvent system had been added (<10 mg/mL). Clear solutions recovered from the assessment were uncapped and allowed to evaporate at ambient temperature to recover solids. Any solids produced via slurries or evaporation were analyzed by XRPD to determine the form.

TABLE 14

Solvent selections for solubility assessment of Form I

| No. | Solvent System |
|---|---|
| 1 | 1-Butanol |
| 2 | 1-Propanol |
| 3 | 99% 1,4 Dioxane:1% Water (% v/v) |
| 4 | 1,4 Dioxane |
| 5 | 59% 2-Propanol:41% Water (% v/v) |
| 6 | 93% 2-Propanol:7% Water (% v/v) |
| 7 | 2-Propanol |
| 8 | 2-Methyl THF |
| 9 | 69% Acetone:31% Water (% v/v) |
| 10 | 95% Acetone:5% Water (% v/v) |
| 11 | Acetone |
| 12 | Acetonitrile |
| 13 | Dimethyl Sulfoxide |
| 14 | 48% Ethanol:52% Water (% v/v) |
| 15 | 86% Ethanol:14% Water (% v/v) |
| 16 | Ethanol |
| 17 | Ethyl Acetate |
| 18 | Ethylene Glycol |
| 19 | Cyclopentane Methyl Ether |
| 20 | Isopropyl Acetate |
| 21 | 48% Methanol:52% Water (% v/v) |
| 22 | Methanol |
| 23 | Methyl Acetate |
| 24 | Methylethyl Ketone |
| 25 | Methylisobutyl Ketone |
| 26 | N,N'-Dimethylacetamide |
| 27 | N,N'-Dimethylformamide |
| 28 | Nitromethane |
| 29 | tert-Butylmethyl Ether |
| 30 | THF |
| 31 | Toluene |
| 32 | Water |

Primary Polymorph Screen

A second batch of Compound 1 bis-tris salt was prepared via normal methods (e.g. lyophilisation, rotary evaporation, milling or quench cooling) to provide a disordered starting point and minimise the presence of seed material. A polymorph screen was carried out in 24 solvent systems in order to identify any potential anhydrous or solvated forms. Crystallization conditions investigated included thermal cycling, evaporation, cooling, anti-solvent addition and solvent drop grinding. The primary polymorph screen was carried out as follows. To ca. 50 mg of poorly crystalline Form I from freeze drying in water an appropriate volume of the solvent system was added to form a slurry. See Table 15 for the volumes of solvent used.

The solvent systems were selected based on the results of the approximate solubility screen. Ethylene glycol and water mixtures were used for increased solubility. Temperature cycling was carried out between ambient temperature and 40° C. in 4 hour cycles for ca. 72 h with agitation. After ca. 24 h further solvent was added where experiments were observed to be immobile slurries (1,4-dioxane:water 59:41 v/v, 2-propanol: ethylene glycol 50:50 v/v, ethanol: ethylene glycol 50:50 v/v, DMA: ethylene glycol 50:50 v/v, THF: ethylene glycol 50:50 v/v, methanol:water 48:52 v/v and DMA:water 50:50 v/v) and further solid was added to solutions or thin slurries (2-Me THF: ethylene glycol 50:50 v/v, 1,4-dioxane: ethylene glycol 50:50 v/v, ethylene glycol, water and acetone: ethylene glycol 50:50 v/v). After ca. 48 h further solid was added to 2-Me THF: ethylene glycol 50:50 v/v which was observed to be a solution and further solvent was added to methyl acetate experiment. Post temperature cycling the solids were isolated by centrifugation using 0.22 μm nylon filters and analyzed by XRPD. The saturated solutions obtained were then divided into four for fast cooling, anti-solvent addition at ambient, slow evaporation at ambient and solvent drop grinding.

TABLE 15

Solvent volumes used for temperature cycling

| Number | Solvent System | ICH Class | Volume Added (mL) |
|---|---|---|---|
| 1 | 1-Butanol | 3 | 2.5 |
| 2 | Acetone | 3 | 2.5 |
| 3 | 50% 1,4-Dioxane:50% Elhylene Glycol (% v/v) | 2 | 1.0 |
| 4 | 59% 1,4-dioxane:41% Water (% v/v) | 2 | 0.5 |
| 5 | 50% 2-Propanol:50% Ethylene Glycol (% v/v) | 2 | 0.5 |
| 6 | 59% 2-Propanol:41% Water (% v/v) | 3 | 0.3 |
| 7 | 50% 2-Methyl THF:50% Ethylene Glycol (% v/v) | 2 | 1.0 |
| 8 | 2-Methyl THF | 3 | 2.5 |
| 9 | 50% Acetone:50% Ethylene Glycol (% v/v) | 2 | 0.5 |
| 10 | 59% Acetone:41% Water (% v/v) | 3 | 0.8 |
| 11 | 50% Acetonitrile:50% Ethylene glycol (% v/v) | 2 | 0.5 |
| 12 | Dimethyl Sulfoxide | 3 | 0.3 |
| 13 | 48% Ethanol:52% Water (% v/v) | 3 | 0.3 |
| 14 | 50% Ethanol:50% Ethylene Glycol (% v/v) | 2 | 0.3 |
| 15 | Ethanol | 3 | 2.0 |
| 16 | Ethylene Glycol | 2 | 0.3 |
| 17 | Ethyl Acetate | 3 | 2.5 |
| 18 | 50% Methanol:50% Ethylene Glycol (% v/v) | 2 | 0.3 |
| 19 | 48% Methanol:52% Water (% v/v) | 2 | 0.3 |
| 20 | Methyl Acetate | 3 | 2.5 |
| 21 | 50% N,N'-Dimethylacetamide:50% Water (% v/v) | 2 | 0.3 |
| 22 | 50% N,N'-Dimethylformamide:50% Ethylene Glycol (% v/v) | 2 | 0.3 |
| 23 | 50% THF:50% Ethylene Glycol (% v/v) | 2 | 0.3 |
| 24 | Water | N/A | 0.3 |

Subsequent crystallization experiments were carried out as follows. Fast cooling: Saturated solutions of Compound 1 tris salt were stored in the fridge (5° C.) for ca. 4 days then moved to −18° C. where no or an insufficient amount of solids for analysis was observed. Slow Evaporation: Saturated solutions were transferred to 2 mL vials and uncapped and allowed to evaporate at ambient temperature and pressure to recover solid material. Anti-solvent addition: Anti-solvent was added dropwise with stirring to saturated solutions at ambient. The anti-solvent and volumes used are shown in Table 16. Where there was insufficient material the experiments were stored at 5° C. to encourage precipitation. Solvent drop grinding: To ca. 20 mg of poorly crystalline Pattern 1 from freeze drying in water, 1-2 drops of saturated solution was added and 2×2.8 mm bead mill beads were added. The experiments were loaded into the bead mill and shaken in 10×90 second intervals with a 10 second pause between each interval at 6000 rpm. 4 cycles in total were carried out.

TABLE 16

Anti-solvent volumes used for anti-solvent additions

| Number | Solvent Systen | Anti-Solvent | Volume of Anti-solvent Added (mL) |
|---|---|---|---|
| 1 | 1-Butanol | t-BME | 1.7 |
| 2 | Acetone | t-BME | 1.7 |
| 3 | 50% 1,4-Dioxane:50% Ethylene Glycol (% v/v) | THF | 1.7 |
| 4 | 59% 1,4-dioxane:41% Water (% v/v) | THF | 1.7 |
| 5 | 50% 2-Propanol:50% Ethylene Glycol (% v/v) | THF | 1.8 |
| 6 | 59% 2-Propanol:41% Water (% v/v) | THF | 1.8 |
| 7 | 50% 2-Methyl THF:50% Ethylene Glycol (% v/v) | THF | 1.7 |
| 8 | 2-Methyl THF | t-BME | 1.7 |
| 9 | 50% Acetone:50% Ethylene glycol (% v/v) | THF | 1.6 |
| 10 | 59% Acetone:41% Water (% v/v) | THF | 1.8 |
| 11 | 50% Acetonitrile:50% Ethylene Glycol (% v/v) | THF | 1.8 |
| 12 | Dimethyl Sulfoxide | THF | 1.8 |
| 13 | 48% Ethanol:52% Water (% v/v) | THF | 1.8 |
| 14 | 50% Ethanol:50% Ethylene Glycol (% v/v) | THF | 1.8 |
| 15 | Ethanol | t-BME | 1.7 |
| 16 | Ethylene Glycol | THF | 1.8 |
| 17 | Ethyl Acetate | t-BME | 1.8 |
| 18 | 50% Methanol:50% Ethylene Glycol (% v/v) | THF | 1.8 |
| 19 | 48% Methanol:52% Water (% v/v) | THF | 1.6 |
| 20 | Methyl Acetate | THF | 1.7 |
| 21 | 50% N,N'-Dimethylacetamide:50% Water (% v/v) | THF | 1.8 |
| 22 | 50% N,N'-Dimethylformamide:50% Ethylene Glycol (% v/v) | THF | 1.8 |
| 23 | 50% THF:50% Ethylene Glycol (% v/v) | THF | 1.8 |
| 24 | Water | THF | 1.8 |

All solids were characterized by XRPD, gently dried, and re-analyzed by TG/DSC, NMR, FT-IR, and PLM (where material allowed). XRPD samples were dried at elevated temperature (e.g. 40° C.) and re-analyzed by XRPD.

pH 7.4 PBS Pattern 3 Experiment

A pH 7.4 PBS experiment was carried out to repeat the experiment which produced the new Form III in order to investigate and characterize this pattern. The experiment was carried out as follows. 1.3 mL of pH 7.4 PBS was added to ca. 121 mg of Form I to create a slurry. The pH was adjusted from pH 7.20 to 7.47 using 0.2 M NaOH. The experiment was agitated at ambient for ca. 24 h. After ca. 24 h the pH was adjusted from pH 7.21 to 7.44. The solids were isolated by centrifugation using 0.22 μm nylon filter and analyzed by XRPD. The solids were then dried under vacuum at ambient for ca. 17 h and re-analyzed by XRPD.

The pH 7.4 PBS experiment was repeated on a 1 g scale in order to carry out further characterization. The experiment was carried out as follows. 10.7 mL of pH 7.4 PBS was added to ca. 1 g of Form I to create a slurry. The pH was adjusted from pH 7.22 to 7.41 using 0.2 M NaOH. The experiment was agitated at ambient for ca. 24 h. After ca. 24 h the pH was adjusted from pH 7.16 to 7.41. The slurry was analyzed by PLM. Ca. 1 mL of the slurry was isolated by centrifugation using 0.22 μm nylon filter and analyzed by XRPD. The solids were isolated by Büchner filtration with Grade 1 filter paper and dried under vacuum on the filter paper for ca. 1 h. XRPD analysis was carried out on the dried solids.

Stability Testing of Form III

Seven day stability testing was carried out for Form III at 40° C./75% RH and ambient in open vials. 80° C. was carried out in an open 2 mL vial within a closed 20 mL vial.

Form IV

Form IV which was obtained from Form III after stability testing at 80° C. was attempted to be prepared as follows in order to obtain characterization. Ca. 24 mg of Form III was weighed into a 2 mL vial and dried open at 80° C. for ca. 18 h then analyzed by XRPD. Form IV was prepared as follows within a closed vial. Ca. 56 mg of Form III was weighed into a 2 mL vial and dried open at 80° C. within a closed 20 mL vial for ca. 24 h then analyzed by XRPD.

Secondary Polymorph Screen

The secondary screen examined forms obtained from the primary polymorph screen. The forms were scaled-up to 400-500 mg to test reproducibility and carry out the following analyses: XRPD; TG/DSC; DSC; NMR; PLM; VT-/VH-XRPD; thermomicroscopy; DVS; FT-IR; U (H) PLC; 7-Day indicative stability tests at 40° C./75% RH (open vial), at ambient temperature, light and humidity or 25° C./60% RH (open vial) and 80° C. (sealed vial); and solubility in three media with postsolubility.

Polymorph Stability Studies (Competitive Slurring)

Competitive slurry experiments between any anhydrous forms of Compound bis-tris salt were performed in up to 4 solvents at room temperature and at elevated temperature (e.g. 60° C.) with an approximate 1:1 wt./wt. mix of each form in the selected solvents and agitated for ca. 48 hours. The resulting material was analyzed by XRPD to ascertain the form.

Single Crystal Growth

Form I crystals were grown using the following procedure. Ca. 10 mg of Form I was weighed into 9 2 mL vials. 100, 150 or 200 μL of solvent was added. See Table 17 for the volumes of solvent used. The experiments were temperature cycled between 40° C. and ambient in 4 h cycles for ca.48 h. After 48 h ethanol:water 48:52 v/v, methanol:water 48:52 v/v, 2-propanol: water 59:41 v/v and water experiments were observed to be solutions and were stored at ca. 5° C. After 48 h PLM analysis was carried out for the remaining experiments which were observed to be slurries. The slurries were temperature cycled for ca. 4 further days then stored at ca. 5° C.

TABLE 17

Preparation of slurries for single crystal growth experiments

| Solvent System | Volume (μL) |
|---|---|
| 59% Acetone:41% Water (% v/v) | 100 |
| 69% Acetone:31% Water (% v/v) | 100 |
| 48% Ethanol:52% Water (% v/v) | 100 |
| 59% Ethanol:41% Water (% v/v) | 100 |
| 48% Methanol:52% Water (% v/v) | 200 |
| 59% 2-Propanol:41% Water (% v/v) | 150 |
| 59% 1,4-dioxane:41% Water (% v/v) | 100 |
| 50% N,N'-Dimethylacetamide:50% Water (% v/v) | 100 |
| Water | 100 |

Metastable Zone Width Experiments

Metastable zone width experiments were conducted for Form I using the following Procedure. Form I was weighed into 16×1.5 mL vials and 1 mL of ethanol:water was added to each vial at the concentrations shown in Table 18. A magnetic stirrer bar was then added to each experiment and the experiments were placed into the crystal 16 and temperature cycled between 5° C. and 70° C. at 0.1° C./min with 1 h holds at 5° C. and 70° C. for 4 cycles. The experiments were stirred at 700 rpm. After cooling to 5° C. the experiments were then heated to 25° C. and removed from the instrument. XRPD analysis was carried out on the remaining solids.

TABLE 18

Concentrations and solvent systems used for MSZW experiments

| Solvent System | Concentration (mg/mL) |
|---|---|
| Water:Ethanol | 50 |
| 50:50 v/v | 80 |
| | 100 |
| | 125 |
| Water:Ethanol | 50 |
| 40:60 v/v | 80 |
| | 100 |
| | 125 |
| Water:Ethanol | 50 |
| 35:75 | 80 |
| (32:68) v/v | 100 |
| | 125 |
| Water:Ethanol | 50 |
| 10:90 v/v | 80 |
| | 100 |
| | 125 |

Re-Crystallization

The Form I re-crystallizations were carried out as follows to assess the effect of the starting concentration. 1.2 g and 1.5 g of Form I was weighed into 20 ml vials. 10 mL of water: ethanol 68:32 v/v was added to give 120 mg/mL and 150 mg/mL. The slurries were stirred at 70° C. with overhead mechanical stirring to dissolve. The experiments were then cooled to 5° C. over 650 minutes (0.1° C./min, 6° C./h) and held at 5° C. Ca. 0.5 mL of slurry was isolated by centrifugation using 0.22 μm nylon filters and analyzed by XRPD. The experiments were then isolated by Büchner filtration with Grade 1 filter paper and dried on the filter for ca. 1h. Prior to drying on the filter, a small portion of the 120 mg/mL experiment was dried at 40° C. under vacuum for ca. 22 h. The dried solids were analyzed by XRPD.

Example 3. Bis-Sodium Salt, Pattern 3 Analysis

The crystalline Bis-Sodium Pattern 3 material underwent 7-day stability tests at 40° C./75% RH (open vial); at ambient temperature, light and humidity (open vial) and 80° C. (sealed vial), with post-stability storage XRPD and HPLC analysis. The solubility of the bis-sodium pattern 3 salt was assessed.

Example 4. Synthesis of High Purity Compound 1A

Herein we describe manufacturing high purity Compound 1A. The described manufacturing processes are amenable to kilogram scale manufacturing of Compound 1A with ultra-high HPLC purity of >99%.

Scheme A

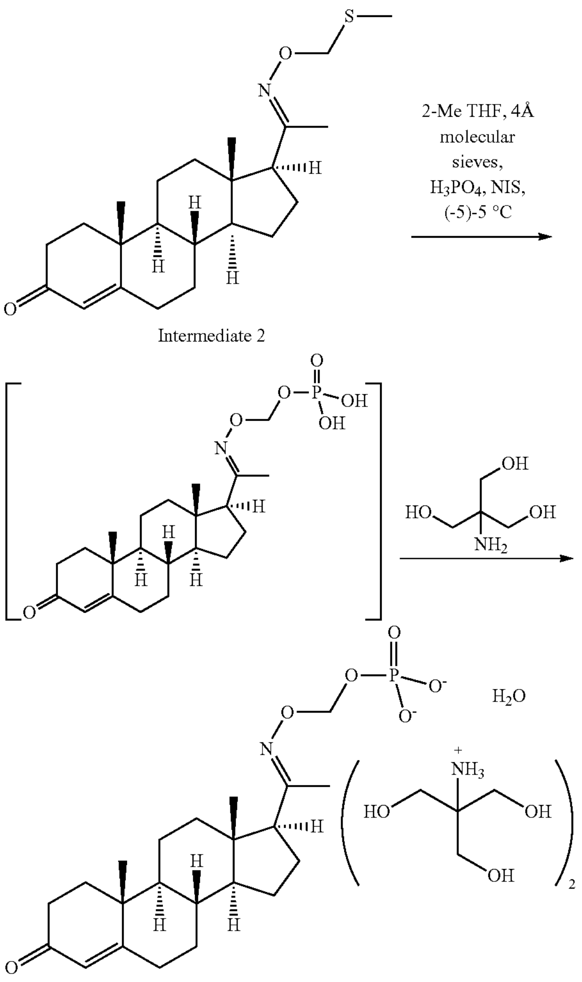

Intermediate 2

Compound 1A

The process for manufacturing of Compound 1A is depicted in Scheme A above. Intermediate 2 can be prepared on a kilogram scale according to previously described methods (Wali et al Neuropharmacology 2016 and Guthrie et al. in US 2018/94018, incorporated herein in their entireties by reference).

A solid charge of Intermediate 2 was added to a clean reactor followed by 30 vol (volumes) of 2-methyltetrahydrofuran (2-Me THF) and 6 g/g of anhydrous 4A molecular sieve beads. The mixture was chilled to −5 to 5° C. and a solid charge 9.4 eq of anhydrous crystalline phosphoric acid was added slowly, followed by addition of 1.5 eq. (equivalents) of N-iodosuccinimide. A 11-12° C. temperature increase and a dark yellow/brown suspension was observed. The reaction mixture was stirred at −5 to 5° C. for not more than 40 minutes. The reaction mixture was then vacuum filtered into a chilled, clean reactor at −5 to 5° C. and the filter cake was washed with 10 vol 2-Me THF. The combined filtrates were charged to a clean reactor. A liquid charge of 12° C. pre-cooled aqueous sodium bisulfite (25 vol, 4.4 w/v %, 4 eq.) was added between 5-15° C. This addition resulted in the formation of an organic top layer and aqueous bottom layer phase. The top organic layer was isolated and washed three times with 5 vol of water at 10-18° C. in a time period of not more than 30 minutes. To the organic layer was added a liquid charge of 1M TRIS (aqueous) to adjust the bottom aqueous layer to a pH between 7.0-8.0 at 9-13° C. After TRIS charge completion, the mixture was stirred at 5-10° C. for not less than 20 minutes. The aqueous layer was separated and transferred to a chilled, clean reactor at 0-15° C. The organic layer was washed with 2 vol of water at 5-10° C. and the combined aqueous washes were added to the reactor containing the first aqueous layer. The combined aqueous layers were filtered through a celite bed to remove turbidity from the solution and charged to a chilled, clean reactor at 0-15° C. To the filtrate was added 3 vol of methanol (MeOH) at 0-15° C. to form a clear, yellow solution. The solution was stirred at −5 to 5° C., followed by addition of Compound 1A seed crystal addition (1.0 wt %) and further stirring for 16-24 hours to form an off-white slurry. The solid Compound 1A was then collected by vacuum filtration and washed with 2 vol of cold MeOH. The Compound 1A was dried in vacuo between 60-70° C. and the solid was then recrystallized in 3:1 MeOH/water.

TABLE 19

Compound 1A Purity Profile

| | | Results (% Area) | | | |
|---|---|---|---|---|---|
| Batch Number | Scale (g) | Compound 1A | Compound A | Compound B | Compound C |
| Batch 1 | 350 | 99.1 | 0.01 | 0.23 | 0.03 |
| Batch 2 | 230 | 99.5 | 0.06 | 0.10 | 0.05 |
| Batch 3 | 203 | 98.3 | 0.07 | 0.40 | 0.03 |
| Batch 4 | 480 | 98.8 | 0.07 | 0.24 | 0.02 |
| Batch 5 | 410 | 98.5 | 0.07 | 0.30 | 0.02 |
| Batch 6 | 511 | 98.8 | 0.06 | 0.30 | 0.02 |
| Batch 7 | 641 | 98.7 | 0.06 | 0.28 | 0.02 |
| Batch 8 | 552 | 99.0 | 0.06 | 0.15 | 0.01 |
| Batch 9 | 482 | 98.2 | 0.06 | 0.15 | 0.02 |

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms may include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:

1. A crystalline form of Compound 1:

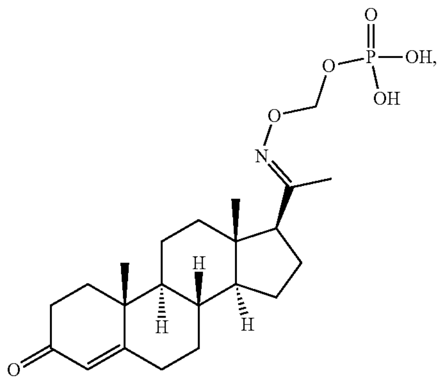

wherein the crystalline form of compound 1 is selected from the group consisting of: crystalline Form I, crystalline Form II, crystalline Form III, crystalline Form IV and crystalline Form V, or a pharmaceutically acceptable salt thereof.

2. The crystalline form of claim 1, wherein the crystalline form is a bis-tris salt, mono-tris salt, or bis-N-(hydroxyethyl) pyrrolidine salt.

3. The crystalline form of claim 2, wherein the bis-tris salt is a monohydrate.

4. The Form I crystalline form of claim 1, characterized by having X-ray powder diffraction peaks at approximately 4.31±0.2, 13.04±0.2, 13.19±0.2, 17.66±0.2, or 19.10±0.2 ° 2θ using Cu Kα radiation.

5. The Form I crystalline form of claim 1, characterized by having an X-ray powder diffraction pattern substantially similar to that set forth in FIG. 1.

6. The Form I crystalline form of claim 1, characterized by an endothermic event with onset at approximately 45.4° C. or approximately 200.6° C. as measured by DSC or by a weight loss of approximately 2.2% between about 25° C. and about 60° C., as measured by TGA.

7. The Form II crystalline form of claim 1, characterized by having X-ray powder diffraction peaks at approximately 13.51±0.2, 13.69±0.2, or 17.66±0.2 ° 2θ using Cu Ko radiation.

8. The Form II crystalline form of claim 1, characterized by having an X-ray powder diffraction pattern substantially similar to that set forth in FIG. 2.

9. The Form III crystalline form of claim 1, characterized by having X-ray powder diffraction peaks at approximately 15.06±0.2, 18.12±0.2, and 20.76±0.2 ° 2θ using Cu Kα radiation.

10. The Form III crystalline form of claim 1, characterized by having an X-ray powder diffraction pattern substantially similar to that set forth in FIG. 3.

11. The Form III crystalline form of claim 1, characterized by an endothermic event with onset at approximately 64.1° C. as measured by DSC or a weight loss of approximately 10.7% between about 25° C. and about 120° C., as measured by TGA.

12. The Form IV crystalline form of claim 1, characterized by having X-ray powder diffraction peaks at approximately 13.74±0.2, 23.16±0.2, or 25.00±0.2 ° 2θ using Cu Kα radiation.

13. The Form IV crystalline form of claim 1, characterized by having an X-ray powder diffraction pattern substantially similar to that set forth in FIG. 4.

14. The Form IV crystalline form of claim 1, characterized by an endothermic event with onset at approximately 153° C. as measured by DSC.

15. The Form V crystalline form of claim 1, characterized by having X-ray powder diffraction peaks at approximately 15.07±0.2, 15.65±0.2, and 15.88±0.2 ° 2θ using Cu Kα radiation.

16. The Form V crystalline form of claim 1, characterized by having an X-ray powder diffraction pattern substantially similar to that set forth in FIG. 5.

17. The Form V crystalline form of claim 1, characterized by an endothermic event with onset at approximately 75° C. or approximately 156° C. as measured by DSC or a weight loss of approximately 1.8% up to about 65° C., as measured by TGA.

18. A method of treating a stroke, traumatic brain injury, or symptom of a stroke or traumatic brain injury in a subject, comprising administering to the subject a crystalline form of claim 1 or a pharmaceutically acceptable salt thereof.

* * * * *